US007442782B2

(12) United States Patent (10) Patent No.: US 7,442,782 B2
Ranum et al. (45) Date of Patent: Oct. 28, 2008

(54) INTRON ASSOCIATED WITH MYOTONIC DYSTROPHY TYPE 2 AND METHODS OF USE

(75) Inventors: Laura P. W. Ranum, St. Paul, MN (US); John W. Day, Minneapolis, MN (US); Christina Liquori, Minneapolis, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 427 days.

(21) Appl. No.: 10/890,685

(22) Filed: Jul. 14, 2004

(65) Prior Publication Data

US 2005/0003426 A1 Jan. 6, 2005

Related U.S. Application Data

(62) Division of application No. 10/143,266, filed on May 10, 2002, now Pat. No. 6,902,896.

(60) Provisional application No. 60/337,831, filed on Nov. 13, 2001, provisional application No. 60/302,022, filed on Jun. 29, 2001, provisional application No. 60/290,365, filed on May 11, 2001.

(51) Int. Cl.
*C07H 21/04* (2006.01)
(52) U.S. Cl. .................................................. 536/23.1
(58) Field of Classification Search ................ 536/23.1
See application file for complete search history.

(56) References Cited

U.S. PATENT DOCUMENTS 6,812,339 B1 * 11/2004 Venter et al. ............. 536/24.31
2003/0108887 A1   6/2003 Ranum et al.

FOREIGN PATENT DOCUMENTS

WO    01/72799 A1   10/2001

OTHER PUBLICATIONS

Buck et al., Biotechniques, vol. 27, No. 3, pp. 528-536, 1999).*
Sequence Information Contained in Celera Accession No. 2HTBKUAD8C, "Conting Overlapping ZNF", pp. 1-310.
Alwazzan et al., "Myotonic Dystrophy is associated with a reduced level of RNA from the DMWD allele adjacent to the expanded repeat," *Hum. Mol. Genet.*, 1999; 8(8):1491-7.
Aminoff et al., "Automotive function in myotonic dystrophy," *Archives of Neurology*, Jan. 1985;42(1):16.
Andrews et al., "The glycoprotein Ib-IX-V complex in platelet adhesion and signaling," *Thromb Haemost*, 1999; 82(2):357-64.
Armas et al., "Primary structure and developmental expression of Bufoarenarum cellular nucleic acid-binding protein: changes in subcellular localization during early embryogenesis," *Dev. Growth Differ.*, Feb. 2001; 43(1):13-23.
Boucher et al., "A novel homeodomain-encoding gene is associated with a large CpG island interrupted by the myotonic dystrophy unstable (CTG)n repeat," *Hum. Mol. Genet.*, 1995; 4(10):1919-25.

Brook et al., "Molecular basis of myotonic dystrophy: expansion of a trinucleotide (CTG) repeat at the 3' end of a transcript encoding a protein kinase family member," *Cell*, Feb. 21, 1992; 68(4):799-808.
Buxton et al., "Detection of an unstable fragment of DNA specific to individuals with myotonic dystrophy," *Nature*, Feb. 6, 1992; 335(6360):547-8.
Davis et al., "Expansion of a CUG trinucleotide repeat in the 3' untranslated region of myotonic dystrophy protein kinase transcripts results in nuclear retention of transcripts," *Proc. Natl. Acad. Sci. USA*, Jul. 8, 1997; 94(14):7388-93.
Day et al., "Clinical and genetic characteristics of a five-generation family with a novel form of myotonic dystrophy (DM2)," *Neuromuscul. Disord*, 1999; 9(1):19-27.
Flink et al., "Organization of the gene encoding cellular nucleic acid-binding protein," *Gene*, 1995; 163(2):279-82.
Fu et al., "An unstable triplet repeat in a gene related to myotonic muscular dystrophy," *Science*, Mar. 6, 1992; 255(5049):1256-58.
Fu et al., "Decreased expression of myotonin-protein kinase messenger RNA and protein in adult form of myotonic dystrophy," *Science*, Apr. 9, 1993; 260(5105):235-8.
Groenen et al., "Expanding complexity in myotonic dystrophy," *Bioessays*, Nov. 1998; 20(11):901-12.
Harley et al., "Expansion of an unstable DNA region and phenotypic variation in myotonic dystrophy," *Nature*, Feb. 6, 1992; 335(6360):545-6.
Harper, "Myotonic Dystrophy," Second Edition, W.B. Sanders, London 1989. Title Page and Table of Contents.
Helderman-van den Enden, "Monozygotic twin brothers with the fragile X syndrome: different CGG repeats and different mental capacities," *J. Med. Genet.*, 1999; 36(3):253-7.
Kawaguchi et al., "CAG expansions in a novel gene for Machado-Joseph disease at chromosome 14q32.1," *Nat. Genet.*, 1994; 8(3):221-8.
Khajavi et al., "Mitotic drive' of expanded CTG repeats in myotonic dystrophy type 1 (DM1)," *Hum. Mol. Genet.*, 2001; 10(8):855-63.
Klesert et al., "Trinucleotide repeat expansion at the myotonic dystrophy locus reduces expression of DMAHP," *Nat. Genet.*, Aug. 1997; 16(4):402-6.
Klesert et al., "Mice deficient in Six5 develop cataracts: implications for myotonic dystrophy," *Nat. Genet.*, May 2000; 25(1):105-9.
Koob et al., "An untranslated CTG expression causes a novel form of spinocerebellar ataxia (SCA8)," *Nat. Genet.*, Apr. 1999; 21(4):379-84.

(Continued)

*Primary Examiner*—Teresa E Strzelecka
*Assistant Examiner*—Cynthia Wilder
(74) *Attorney, Agent, or Firm*—Mueting Raasch & Gebhardt, P.A.

(57) ABSTRACT

The present invention provides methods for identifying individuals not at risk for developing myotonic dystrophy type 2 (DM2), and individuals that have or at risk for developing DM2. The present invention also provides isolated polynucleotides that include a repeat tract within intron 1 of the zinc finger protein 9.

8 Claims, 19 Drawing Sheets

OTHER PUBLICATIONS

Korade-Mirnics, "Myotonic dystrophy: molecular windows on a complex etiology," *Nucleic Acids Res.*, Jun. 1998; 26(6):1363-8.

Kruglyak et al., "Parametric and nonparametric linkage analysis: a unified multipoint approach," *Am. J. Hum. Genet.*, Jun. 1996; 58(6):1347-63.

Lathrop et al., "Strategies for multilocus linkage analysis in humans," *Proc. Natl. Acad. Sci. USA*, 1984; 81(11):3443-6.

Liquori et al., "Myotonic dystrophy type 2 (DM2) Caused by a CCTG Expansion in Intron 1 of ZNF9," *Science*, 2001; 293(5531):864-7.

Liquori et al., "Science—Liquori et al. 293(5531): 864 Data Supplement—Supplemental Data," [online]. Available online Aug. 3, 2001. [retrieved on Sep. 12, 2002]. Retrieved from the Internet: <http://www.sciencemag.org/cgi/content/full/293/5531/864/DC1>.

López de Munain et al., "CTG trinucleotide repeat variability in identical twins with myotonic dystrophy," *Ann. Neurol.*, Mar. 1994; 35(3):374-5.

Lu et al., "Cardiac elav-type RNA-binding protein (ETR-3) binds to RNA CUG repeats expanded in myotonic dystrophy," *Hum. Mol. Genet.*, 1999; 8(1):53-60.

Mahadevan et al., "Myotonic dystrophy mutation: an unstable CTG repeat in the 3' untranslated region of the gene," *Science*, Mar. 6, 1992; 255(5049):1253-5.

Mankodi et al., "Myotonic dystrophy in transgenic mice expressing an expanded CUG repeat," *Science*, Sep. 8, 2000; 289(5485):1769-73.

Matsuura et al., "Large expansion of the ATTCT pentanucleotide repeat in spinocerebellar ataxia type 10," *Nat. Genet.*, Oct. 2000; 26(2):191-4.

Matsuura et al., "Polymerase chain reaction amplification of expanded ATTCT repeat in spinocerebellar ataxia type 10," *Ann. Neurol.*, Feb. 2002; 51(2):271-2.

McPherson et al., "A physical map of the human genome," *Nature*, Feb. 15, 2001; 409(6822):934-41.

Miller et al., "Recruitment of human muscleblind proteins to (CUG)(n) expansions associated with myotonic dystrophy," *EMBO J.*, 2000; 19(17):4439-48.

Moutou et al., "Transition from premutation to full mutation in fragile X syndrome is likely to be prezygotic," *Hum. Mol. Genet.*, 1997; 6(7):971-9.

National Center for Biotechnology Information, National Library of Medicine, National Institutes of Health, GenBank Locus AC022944, Accession No. AC022944, "*Homo sapiens* chromosome 3 clone RP11-814L21 map 3, Sequencing in Progress, 81 unordered pieces," [online]. Bethesda, MD [retrieved on Jun. 21, 2001]. Retrieved from the Internet: <URL: www.ncbi.nlm.nih.gov/entrez/query.fcgi?cmd=Retrieve&db=nucleotide&list_uids=7139791&dopt=GenBank>; 75 pages.

National Center for Biotechnology Information, National Library of Medicine, National Institutes of Health, GenBank Locus AC022993, Accession No. AC022993, "*Homo sapiens* chromosome 3 clone RP11-72304 map 3, Working Draft Sequence, 14 unordered pieces." [online]. Bethesda, MD [retrieved on Aug. 20, 2002]. Retrieved from the Internet: <URL: www.ncbi.nlm.gov/entrez/query.fcgi?cmd=Retrieve&db=nucleotide&list_uids=10046450&dopt=GenBank>; 53 pgs.

National Center for Biotechnology Information, National Library of Medicine, National Institutes of Health, GenBank Locus AC023598, Accession No. AC023598, "*Homo sapiens* chromosome 3 clone RP11-221E20, Working Draft Sequence, 3 unordered pieces." [online]. Bethesda, MD [retrieved on Aug. 20, 2002]. Retrieved from the Internet: <URL: www.ncbi.nlm.gov/entrez/query.fcgi?cmd=Retrieve&db=nucleotide&list_uids=21700434&dopt=GenBank>; 56 pgs.

National Center for Biotechnology Information, National Library of Medicine, National Institutes of Health, GenBank LocusAF388525, Accession No. AF388525, "*Homo sapiens* ZNF9 gene, intron 1 and CL3N58 repeat region." [online]. Bethesda, MD [retrieved on Aug. 20, 2002]. Retrieved from the Internet: <URL: www.ncbi.nlm.nih.gov/entrez/query.fcgi?cmd=Retrieve&db=nucleotide&list_uids=15193053&dopt=GenBank>; 2 pgs.

National Center for Biotechnology Information, National Library of Medicine, National Institutes of Health, GenBank LocusAF388526, Accession No. AF388526, "*Homo sapiens* ZNF9 gene, intron 1 and expanded CL3N58 repeat region." [online]. Bethesda, MD [retrieved on Aug. 20, 2002]. Retrieved from the Internet: <URL: www.ncbi.nlm.nih.gov/entrez/query.fcgi?cmd=Retrieve&db=nucleotide&list_uids=15193054&dopt=GenBank>; 2 pgs.

National Center for Biotechnology Information, National Library of Medicine, National Institutes of Health, GenBank LocusAF389886S1, Accession No. AF389886, "*Homo sapiens* zinc finger protein 9 (ZNF9) gene, exon 1." [online]. Bethesda, MD [retrieved on Aug. 20, 2002]. Retrieved from the Internet: <URL: www.ncbi.nlm.nih.gov/entrez/query.fcgi?cmd=Retrieve&db=nucleotide&list_uids=15193056&dopt=GenBank>;5 pgs.

National Center for Biotechnology Information, National Library of Medicine, National Institutes of Health, GenBank LocusAF389886S2, Accession No. AF389887, "*Homo sapiens* zinc finger protein 9 (ZNF9) gene, exons 2 through 5, and complete cds." [online]. Bethesda, MD [retrieved on Aug. 20, 2002]. Retrieved from the Internet: <URL: www.ncbi.nlm.nih.gov/entrez/query.fcgi?cmd=Retrieve&db=nucleotide&list_uids=15193057&dopt=GenBank>; 4 pgs.

National Center for Biotechnology Information, National Library of Medicine, National Institutes of Health, GenBank Locus HUMZFPSREB, Accession No. M28372, "*Homo sapiens* sterol regulatory element-binding protein (CNBP) mRNA, complete cds." [online]. Bethesda, MD [retrieved on Aug. 20, 2002]. Retrieved from the Internet: <URL: www.ncbi.nlm.nih.gov/entrez/query.fcgi?cmd=Retrieve&db=nucleotide&list_uids=643575&dopt=GenBank>; 2 pgs.

National Center for Biotechnology Information, National Library of Medicine, National Institutes of Health, GenBank LocusHSU19765, Accession No. U19765, "Human nucleic acid binding protein gene, complete cds." [online]. Bethesda, MD [retrieved on Aug. 20, 2002]. Retrieved from the Internet: <URL: www.ncbi.nlm.nih.gov/entrez/query.fcgi?cmd=Retrieve&db=nucleotide&list_uids=790570&dopt=GenBank>; 4 pgs.

Orr et al., "Expansion of an unstable trinucleotide CAG repeat in spinocerebellar ataxia type 1," *Nat. Genet.*, Jul. 1993; 4(3):221-26.

Otten et al., "Triplet repeat expansion in myotonic dystrophy alters the adjacent chromatin structure," *Proc. Natl. Acad. Sci. USA*; Jun. 6, 1995; 92(12):5465-9.

Pellizzoni et al., "Cellular nucleic acid binding protein binds a conserved region of the 5' UTR or *Xenopus laevis* ribosomal protein mRNSs," *J. Mol. Biol.*, Mar. 28, 1997; 267(2):264-75.

Pellizzoni et al., "Involvement of the *Xenopus laevis* Ro60 autoantigen in the alternative interaction of La and CNBP proteins with the 5'UTR of L4 ribosomal protein mRNA," *J. Mol. Biol.*, Aug. 28, 1998; 281(4):593-608.

Philips et al., "Disruption of splicing regulated by a CUG-binding protein in myotonic dystrophy," *Science*, May 1, 1998; 280(5364):737-41.

Pulst et al., "Moderate expansion of a normally biallelic trinucleotide repeat in spinocerebellar ataxia type 2," *Nat. Genet.*, Nov. 1996; 14(3):269-76.

Rajavashisth et al., "Identification of a zinc finger protein that binds to the sterol regulatory element," *Science*, Jul. 7, 1989; 245(4918):640-43.

Ranum, "Genetic mapping of a second myotonic dystrophy locus," *Nat. Genet.*, 1998; 19(2):196-8.

Reddy et al., "Mice lacking the myotonic dystrophy protein kinase develop a late onset progressive myopathy," *Nat. Genet.*, Jul. 1996; 13(3):325-35.

Ren et al., "Hydrolysis of GTP on rab 11 is required for the direct delivery of transferrin from the pericentriolar recycling compartment to the cell surface but not from sorting endosomes," *Proc. Natl. Acad. Sci. USA*, May 1998; 95(11):6187-92.

Ricker et al., "Proximal myotonic myopathy: a new dominant disorder with myotonia, muscle weakness, and cataracts," *Neurology*, 1994; 44(8):1448-52.

Ricker et al., "Linkage of proximal myotonic myopathy to chromosome 3q," *Neurology*, Jan. 1, 1999; 52(1):170-1.

Sambrook et al., "Molecular Cloning: A Laboratory Manual," Cold Spring Harbor Laboratory, New York; 1989; title page, publication page, table of contents; 30 pgs.

Sarkar et al., "Heterozygous loss of Six5 in mice in sufficient to cause ocular cataracts," *Nat. Genet.*, May 2000; 25(1):110-4.

Schneider et al., "Proximal myotonic myopathy: evidence for anticipation in families with linkage to chromosome 3q," *Neurology*, 2000; 55(3):383-8.

Spielman et al., "Transmission test for linkage disequilibrium: the insulin gene region and insulin-dependent diabetes mellitus (IDDM)," *Am. J. Hum. Genet.*, Mar. 1993; 52(3):506-16.

Takahashi et al., "The CUG-binding protein binds specifically to UG dinucleotide repeats in a yeast three-hybrid system," *Biochem. Biophys. Res. Commun.*, Oct. 22, 2000; 277(2):518-23.

Taneja et al, "Foci of trinucleotide repeat transcripts in nuclei of myotonic dystrophy cells and tissues," *J. Cell Biol.*, Mar. 1995; 128(6):995-1002.

Tapscott, "Deconstructing myotonic dystrophy," *Science*, Sep. 8, 2000; 289(5485):1701-2.

Tapscott, "Reconstructing Myotonic Dystrophy," *Science*, 2001; 293:816-7.

Thornton et al., "Myotonic dystrophy with no trinucleotide repeat expansion," *Ann. Neurol.*, Mar. 1994; 35(3):269-72.

Thornton et al., "Expansion of the myotonic dystrophy CTG repeat reduces expression of the flanking DMAHP gene," *Nat. Genet.*, Aug. 1997; 16(4):407-9.

Timchenko et al., "Identification of a $(CUG)_n$ triplet repeat RNA-binding protein and its expression in myotonic dystrophy," *Nucleic Acids Res.*, Nov. 1, 1996; 24(22):4407-14.

Ullrich et al., "Rab11 regulates recycling through the pericentriolar recycling endosome," *J. Cell. Biol.*, Nov. 1996; 135(4):913-24.

Venter et al., "The sequence of the human genome," *Science*, Feb. 16, 2001; 291(5507):1304-51.

Warner et al., "A general method for the detection of large CAG repeat expansions by fluorescent PCR," *J. Med. Genet.*, Dec. 1996; 33(12):1022-6.

Wong et al., "Somatic heterogeneity of the CTG repeat in myotonic dystrophy is age and size dependent," *Am. J. Hum. Genet.*, Jan. 1995; 56(1):114-22.

"Zinc Finger Protein 9; ZNF9," Online Mendelian Inheritance in Man-John Hopkins University. [retrieved on Apr. 30, 2002]. Retrieved from Internet: <URL: http://www.ncbi.nlm.nih.gov/entrez/dispomim.cgi?id=116955>.

"ZNF9: zinc finger protein 9 (a cellular retroviral nucleic acid binding protein)" [online]. *Homo sapiens* Office Gene Symbol and Name (*HGNC*), [retrieved on Apr. 30, 2002]. Retrieved from the Internet: <URL: www.ncbi.nlm.nih.gov/LocusLink/LocRpt.cgi?1=7555>.

Zhuchenko et al., "Autosomal dominant cerebellar ataxia (SCA6) associated with small polyglutamine expansions in the $\alpha_{1A}$-voltage-dependent calcium channel," *Nat. Genet.*, Jan. 1997; 15(1):62-9.

* cited by examiner

E

```
                     Exon 1: 4337-4415
Intron 1 Gap (size unknown): 14469-14473
         CL3N58 repeat region: 17702-17857
                     Exon 2: 18662-18799
                     Exon 3: 18896-18987
                     Exon 4: 19156-19356
                     Exon 5: 19865-20845 actaatgaaa tgttcattaa atgatttgtc agtgtttcaa agtttcttta
            tcatcagtta gcattcccta caccatcact ttagggagtc aatagaattt
            tataggagta ggcttcagta agtactggga ggccagtagc actgttcaag
            cacatgggct gtctgtgttt gaagcctgac ctgtcatttg ttcactttct
            gacttgagca gattacttaa actctctcga cctgttcttt catgggdata
            atacaagtac ttctaggggg tttgtgaaaa ctcataaaga ggttaaaaac
            attgcctggc atacagtaag cacccaataa gaataagaaa taatatttgt
            atagtaatta tgccagaaac tgttataaga gctgtatata tattaacaat
            tagctattac tagtattact aattcctagt tcaggattta gcttagtaaa
            ctttctgctt cagaagcaaa tacgagaggt gaaaacatca atttattctc
            ctcagtctta gttacatact ttccaagtca agtcacagag cacaatttcc
            ttgctggcag ggacaagaca tgggtttaca tgatatcacc tatcccctca
            atttaacagc atgtactatg cagttgggca tttaagcaga aattaagagt
            tggcaggtat tgctcaactg gtacccattt taggaataat gctgaatcat
            agcattttat ctggtcttct ctcaggatac ttaatgctaa ttttttgtat
            ttttagtaga gacgggattt caccttgtta gccaggatgg tctcgatctc
            ctgacctcat gacccatctg cctcggcccc ccaaagtgct gggattatag
            gcgtgatcca ccgtgcccgg acttttttt ttttttttt tttgagacag
            agtctcctc tgttgtgcag gctggagtgc agtgcccaa tctcttgctc
            ccaggtgcaa gcgattctcc tgcctcagct tccaagtag ctgggattac
            aggtgcccac caccacactc ggctaatttt tgtgttatta gtagagacaa
            gttttcacta tgttgccag gctgctctca aactcctgac ctcaggtgat
            ccacctacct cggcctccca agtgctggga agttgttttt ttttctttt
            cttttttga gactgagtct tgctccgtca cccaggctgg agtgcagtgg
            cgtgatctcg gctcactgca agctctgcct ctcaggttca aacgattctc
            ctgcctcaac ctctcgagta gcttggacta taggtccccg ccaccacgac
            cagctaattt tttgtatttt tagtagacag gatttcaccg tgttagccag
            gatggtcttg atcagctgac ctcgtgatcc gcccgcctcg gcctcccaaa
            gtgctggatt acaggcgtga gccaccgaac ccagccgaca cttaatactt
            tcttatggcc cttgttatcc tgcaagttct tcaagggcaa actctgtgtc
            ttaagtagtc acctttgtaa cccttgcaat gctgagcatg agactgaaca
            ctggaggaga ggaggggaat aaaacatctc cagggaagag gaatgtaatg
            ggagcctctt caagtcccac tggcagctta tcttttgagt gagcttttc
            ctattttcaa acatttctag taaaataggc ataccaaagg gtatatccag
            gcaatacaag ccattgtagt taaattccac catacacctt ttctggcgcc
            tcacgatcag cctggctcta ttaataatag tcgttacagg aagctgcatg
            ccaggtagaa agagccatta gctgttacca ctccactgcc aagaagtaaa
            gacattgttt ccatttcttc tacttaagtc ttttaaaacc tatagaacat
```

Fig. 7a tatgtccagt atctctatct cacactcact ttcattttct atagctgttg
aaatttttgt tttaatatta ggaatattcc attcctgggt ctataatgaa
tagcaaacat tttatacagt actatggttg gaatggtaaa caaaaataag
tcagaaaata ttaatttttg gccatatggt aatttttaact tgtcctcttg
gtgtggtgtg gacgcaccca ggttggactt catacatagc ctcttgcatt
atattgactc attgtcagag ctcacgaagt cactacctaa gtgtctgatt
gctacactat acattacttc aagatactat gaaggttaat cagattacaa
aggggaaatc ataaagctga gtaagcttct tggtaataaa actatataaa
tacaaaatac tgtttttttat tggcagataa tatatcgtgt tttagcacaa
cacataagct gctaggcatt tattcaatct gattgggaat gggttaaatt
tggttaaaaa attttacctt aggttgcttt aattaaaaaa atgtttaagg
ctgagtgcag tggctcacac ctgtaatcct agcactttgg gggcactggg
tgcagtggct cacacctgta atcctagcac tttggcctag caccgcttga
ggccaggagt tcaagcccag cctggccaac atgatgaaac cccatctcta
ctaaaaatac aaaaattagc caggcgtggt ggtgggcgcc tgcagtccca
gctactcagg aggctgaggc agaattggtc aaacatggga agcggaggtt
gcagtgagct gagacagcac tccagcttgg caacagagg gagaccctgt
ctcaaaaaat agtaataaat aaatttaaaa agttcggcca ggcgcggtgg
ctcatgcctg taatcccagt gctttgggag gacgatcacc actttgggtg
ggcggatcac ctgaggtcgg gagtttgaga ccagcctgac caacatggag
aaaccccgcc tatactaaaa atacaaaatt agccgggcgt ggtggcgcat
gcctataatc ccagctactg gggaggctga ggcaggagaa tcacttgaat
ccaggaggcg gaggttgcag tgagctgaga tcgtgccatt gcactccagc
ctgggcaacg gagtgagact ccgttctcaa aaaaaaaaa aagtttaaaa
tatcattggt ctttaaagtt atacattcat tctttgataa ttgctatgtt
gaacgcaacc tcctaactgc tttacaatga ttaagcacta atgatttgaa
cccaggttta aagtctgact ctcaacacat gtgctctgcc ttctcacgaa
catgatttca aaaatcatag ccccgggatt tgggattggt ggcttatgcc
tgtaaaccca gcgacagagc aagacctac tcttaaaaaa aaaaaaaatt
aaagaaaaaa agaaaaataa atcatagtgt tgaactggca ggtttcactg
agacgaaact tgggactctt cctttttttt tgtttcgaat aaagccattc
tagaatgaga caaaattcta aaatatttta tagttaacag tttaaattgg
gtttaatctt gacaagacta tctagggcta tatacacaaa tctcttttgg
agaaaatacc acaactaaac tgaagtctat tcctgaatat gacagaccag
gtcaaatggt tatccttgcc ctcccggggg atgtcactca taaacgtgcc
aaaagtcaca gtctaggccc cattacctta catgctcatg accttcccag
ggaggcccct cgcccttacc aggcactttc atcttgggaa gacacatcag
tcctggcgga gaaagcagca aggcctttcc ccggctcaca aaaattaata
caaatctcag aggctgcatc ccacagccgt gaccaccgtg acttggcatc
ccctttctg caaacttaaa tgttatctag aaatcgggcc tggctctgaa
agccaaggc ctggcaggag cccgagaaag gggagaaact ttctgcggcc
ccaagctaat ggcagtcact gcaccgagac ccgtccctg gcatcccttt
gctccagctg gccaagacag accaccaagg tcagccagat ttccacccag
tctggccggg cccggaccca gctgggaatg aaccgagaag caccgggacc
cggatcccgg cgtgaaaggc cgcgcgcggg gcacggcggg aaaagacgct
gcgcgcagaa acacccgccc cgcgccgcgc tctagtgggc ggccctgccg

Fig. 7b

```
cgggcggctc tgattggact gccgaacccc gcgcgctgat tggccgcgtg
ggcgaggcgg aggagagccg tgcgcagcgg cgtatgtggg gccgtgtgca
gacccgcgtg tggcgcaggc aaggaccctc aaaataaaca gcctctacct
tgcgagccgt cttccccagg cctgcgtccg agtctccgcc gctgcgggcc
cgctccgacg cggaaggtga gggctggggg aggggcccgg cgctgacgga
gccgcagtgc gggtcgggtc tgtggcggac agagagggta gggagcggcg
aggtggcgat ggcggccgca ctttggcctg cgcctctgct gcgtcaggcg
ggaagctcgg ctgctgccgc cgcctcggac ccgggtttct ggcgcaccgc
tgtcggacga cacttctgtc ctttcttcgt cctggaaagc tgggtcgccg
agcatgcggg tctttcggcg ccacggccgc acccaggcc gcaggcttag
ggcagaggag gcccgcccgt gcgcccttgg ggccgaggcc ctgacgcttc
gagggtcgcg gaatgaggga ccgagggtgg atttggcggg aactcactgg
aaggagtccg tgtggtgggg aaaggctccc ggctgcggat gaagggggga
tggggtgggt atagtcgtgc aggccatgtg ctggggtcgt gcgcctggcg
ggccatgtgc caagggtttt gggggcctta gaaaagggtt cttaggccgg
gcgcggtggc tcacgcctgt aatcccagca ctttgagagt cccaggcggg
cggatcacga ggtcaggagt tcgagaccag cctgaccaat atggtgaaag
ttggtctgta ctaaaaataa aaaattagcc gggcatggtg gcgggcgcat
gtagtcccag cagctcggga ggctggacag gagaatcgcg tgaaccccgg
aggccgaggt tgtggtgagc cgagatcgcg ccactacact ccagcatggg
caacagagag agactccgtc ttaaaaaaac aaacaaacaa acaaacaaac
aacaacaaag ggttcctgaa gaagcctttg tgtttggagt ggcgagactg
ctggaagact tgggagcttt tagagtttat actccctatc cttgatagtt
ttccgattct tgaattttta tcgtcattta aatactaagt tgcttgtgtt
acattaccat tccaaagggg ctgatgggg ctcacattcc aagagttaac
actatttaag ttgctgggat cctttaaaag cgccattacc agaaaaaaca
cgaatttgtc aaacctccaa aaccacagca gcgggcggta gtctgcatca
tttcttggat taatgaaaca gatgtaatta caaacgagac acgaaattca
actagctccc ctccatctag attttccat atcgtgagaa cctgttttag
aatggcataa tggtccacat ttgggtttag gtgttgattt tattatgggt
aaggcttgtg cttgttccca catgttaacc atatggcctc agccacaggg
cacttccaaa ggaagtgact gtttctggtc ttgggggtct tgtaaaaaga
gaacattgct cagtaatcgt ctgtgatttt agctagtgtg tttcaggcat
tattcagaag gactcaggtg agataagcca aaactgaatt tgttttttgt
ctttctcaaa gtgaaggagg tctaatgaat atccccatct tgcttttaaa
ttacattttt aaaagtagat ttttccccct ttcctattgt ttgacccaat
tttggagtga aacgtaacca gttactattt ccattcgaat ttaaattagc
aattttatgt tatttgtttg ttcaagcagt ataactggag tgtagagctt
tgagggtttc aaaaagataa gagatatagt acttatctcc tgggcttccc
cctccccct cctaaatagt tttaaatgct tctaatgagt tactctggtt
aaggataatc aaacacctgt aaactgccag gatcctaggt acatgctgtt
tttagtttgt tgagcctgat tcttgtctac aagagttctt tgtgtattgg
aatataaaag gaataattta ttacattccc aagggcagaa ttaaagactt
aagtttttcc gatttcatct cttgataagt ttttctttaa aaaataaca
gtttgtgttt ttctgaggaa ccaaaggtcc tcttttttt catattggta
acaggagagg taatgtattt cagatggtgc agtctgtaaa atattttgaa
```

Fig. 7c

```
ccaaatcagt ggaagaccag gggttttct ttttttttt ctgagacgga
gtctcactct gtcgcccaag ctggagtgca gtggcgcgat ctcggctcac
tgcgacctcc gcctcccgga ttaagcgatt ctcctgcctc agcctccgaa
gtagctggga ttacaggcgc ccgccgccac acccagctag ttttgtatt
ttagtacaga cggggtttca ccatgttggc caggctggtc tcgaactcct
gaccttgtga tccgactccc tcggcctctc aaagtgctag gaaaacaggc
aggagccacc gcgcctggcc aggttttct taaactggca tttgaacatc
tggaacaggc agggagatgt ctttttaaa gtataaatgt gttttgttac
atgatttatg acaattctac ttgtcttttt ttttttttt ttttttgag
acagagtctt tctctgtcgg ccaggctgga atgcagtggc acagtctcgg
ctcacagcag cctccatctc ccgggctcaa gcaattctcc tgcctcagcc
tcccaagtag ctgggattac agggcgtgtg ccaccacgcc cggctaattt
ttgtattttt tgtaaagacg gggtttcacc atgttggcca ggctggtctt
gatctcctga cctcaggtaa ttcacccgcc tcggcctccc aaagtgctgg
gattacaggc ctgagccacc gtgccttgcc aacaattcta cttgtctttt
aaagttcaat aaaaatatgt ggcacgtata tgggatagta ccaaactggt
gcctaaaagc agtgaaacca ccattggact aattggaatg atttgtctat
tggctgaaga tttgaccaca gagagattct gctttttttt ccttgcaggg
atgaaaaatt aaaaaaaaaa aaaagattg gttcctttt ctcttcctag
cctcctgaca gtaagtagag agccagaaga atgatgccaa ggcatcctgg
cctgctatgt ggagaacgct ctttccttac tgtctcactt aatagaactc
ctgttctggc agtgtcagat gctgcagcag caagggaatg ccattgagtg
attgcagtaa gctatgcagc attttcatgt ttaaaactac tgagataata
aagtgagaac ttgaggccac caaatttaa gttgtaatta gaaggatttt
gttaattagg aatatgagag tgctacagtg atcacctgga atggctccat
aaatacaaat gaggtgttaa ctagtgaagc aagttgccag tgtttgtgtg
tttggtgaga ctcctaagtt ctgccatgaa gttaaagaaa atattttta
agattcaaga aagctgtgtg aatgaattca aaattattat gactgtagat
cttttaaaaa gctatcagta ttagttttac tttgattttt atctaaagag
aaatacagaa tgaatactta cagcattaca attcaaatgt gcgtggcttt
tttttttctt agttactaga tatatagtag taataccttt atgtaatatt
ttgaagtaga gattgaattg gtataattcc ctaccttaaa aatattacac
aatagcattt ttgtcatata ttacgatagc attttgtgt actttaccac
ttaactttt tttcctttt cttttttt tggagacaaa gtcttgctct
gtcgcccagg cgggagtgca atggcaggat ctcagctcac tgcaacctct
gcctcctggg tttaagccat tctcctgcct cagcctcctg agtagctggg
actataggcg tgtgccacca cgcccggcta atttttgttt tttagtttt
ttttggagac ggagtctcgc tttgtcaccc acactggagt gcaaatggca
tgatctcggc tcactgcagc ctccacctcc tgggttcaag cgattctctt
gcctcatgca ccaccacgcc cagttaattt ttgtatattt agtagagatg
gggtgtcact atgttggcca ggctgccgac ctcaagtgat cttccctcct
cagcctccca aagtgctggg attacaggca tgagccactg cccctggcca
gtgtcagatg tttagtttgt cattaaaatg gagcaagaat acataactcg
tgaggttgta agattataga tatgtttact aatgactgac tcatagatat
ccagctgtta aaactcttca agaagtaatc agggcaggcg gaaatggatg
taattaacca aggtcaagca gtaagttcag gaaccaggat aaaaatacag
```

Fig. 7d

```
aattgctccc gagtaagtac tctgttttcc attattctgg ctggaatgca
ggtaatacag aaagtatatt gcttcctttc attgcttttt ttttcttctt
ttttcctttt gaggtggagt ttcgctcttg ttgcccaggc tggagtgcga
tggcatgatc tcggctcacc gcaacctctg cctcctgggt tcaagcaatt
cttgtgcgtc agcctcctga gtagctggga ttacaggcat gcaccaccat
gtccagctaa tttttgtatt tttagtagag acagggtttc accatgttgg
ctagctggtc tcgaactcct gacctcaggt gatgcatctg cctcggcctc
ccaaaatgct gggattagag gtgtgggcca ccccgcccgg cccagacctt
atcttgacta tcttagtcat ttcttctctt gcctgacatg ccctgtgctc
ctaccaccct ttaaagtggt ttgtgtcata aacatttgat acacaaaaat
ggaaacttag gacaaatatc ttgatgtctg gtggttgaaa atgtgaactg
atttggaaat caccggtgtt tctcctctta atctcttctc cattccattc
aggaaataga ctgtaaggtg ggaaacaagt ataagcagtt agcctcactc
taaacctgct atgtaataga cattggactg agttctgtct actctctgta
agcaatccaa ggtaattggc gaaagtggaa ggaatatgta ctcagaagac
caaaactttg gtttttaaat tgaatatcta ttaagcacaa ggtaacaatt
cttaccacac acatcagttt tattatttcc cttttacaaa taagacacag
atgggtagtc agatgtcttt gaggtaacac agcaagtagt taaactgggt
taagtgatta acccaggttg agtatggttc caaaatctct tacagtgtca
ggcaggctac atcagtgcag tatacgtaca tcaggtttca cgaaaaattt
tttccagaga aaacacaaac ccaaggaacc ttcagtaagt ggtgccttat
attagtggtt tttagcaaaa ggaagaaact taagtgtttt cctgctgcct
gacaaaagtg aaaaacagta ttttggtttt tattgaagtt agcatgtatg
tttgtagctt gcataaaata gtactgaaat ccaattgatt atgaattctt
ggactaacag aacctggatg acaaattaga ggttctggcc tggttgctgg
cttttttagt tgtcttgggt gtaaatttct cagccacacg tggggattgt
gttagataat ctgaaatcta attttcatgg ttttatgatt cagcagcttt
cttcctttga tattttctag tatttgcttt attatagatt ggaatcctca
aaataacatt gacaagtaga agatacttct gttagtggat taaaaaaaa
attacattgg gaatgtcctt tgagtggttg gccctaatcc ctgtcagaag
ctgaaagttg tggatcctaa attcatctgg gcagaatctc acctatgatt
tcagaaagct gagagtttca gagagtgact gtagtcagtc cttagtgagt
acaaaattga gaatacatca ttactttaaa ttaatggtgc agtaactctt
gtgactgata gcaataattt aggtgctttg ttgttagtac ttgattagat
tggattgggt cagttagttt caccaaattg ctaaagacac ctgtccccct
agaattaaaa tactgagtta cataatggct actaaaagga taactatatg
gggtgttcga tgattcaaag gtgaattact tggtctctac cttcaaggaa
tatgatacaa ggcaatatgg tactgccatt agacagatat taacaaagtg
tcttgggact taatagggag ggtagttcca ggctgggaga tgtagtcaga
ttcttttata gagttggcat ttgagttggc ccgtgaaggt tggaaaaagt
tgtgacaggt ggaaaggag caggggagac caggacagtg cagtgaaatt
ccagccagga gcagtcatag gcaatgagac agactcatgg agccatgatt
ctcagctgtc ttaccttacc ttagttttcc taaggaatat catggaattc
tgtaaagacc tttaaactaa ataatgttca tatgagatga gtgctaggat
ggggacctgc tgcctaatat aagtagtgtg agtctaaaac attgtggaaa
gtggttagtt taataatgtt attaaagaga caagtctatc acaagggacc
```

Fig. 7e

```
agttaccagt gaaactgtag accacctgat tcactgcgat agggttagcc
aaagggagga gagggcagat tgcatacata gtacctaagg ccactcaaag
acctctttta aaatcacgtg tcatgttgat gacatttgga ggctattaat
gtttttcttc ccttttaaga cttagtgttt tctttattag cattaattta
ctctagtaaa caaaattatg tgtgactaaa aatggcaaaa caggctgggc
gcagtggctc acgcctgtaa tcctaacact tgggaggcc aaggcgggtg
gatcactagg tcaggagatc gagaccatcc tggccaacat ggtgaaaccc
cgtctctact aaaatacaaa aaattacctg ggcgtggtgg tgcacgcctg
tagtcccagc tatgtgggag gctgaggcag gggaatcgct tgaacccagg
aggtgaaggt tgcagtgagc caagattggg ccaccgcact ccagcctggg
acagagcgag actccatctc aaaaacaaaa aaagatcca aattagaaga
acatggtggc atgcgcctgt agtcccagct acttgggagg ctgaggcagg
agaattactt gaacccggga ggcagaggtt gcagtgagcc gagattgcac
aactacactc cagcctgcgc aacagagcaa gactccatct caaaaaaaaa
aaagaaaga aagaagaaa gaaactggag ggaacaatgc cctaatgtat
taacaatcat cacatatgag gtgtgaaaat gtgagtggtt ttttctgat
tttctgtatt ttataacttt tttttgtttg agatggagtc ctgctctgct
gcccaggctg gagcgcagtg ggacgatctc ggctcactgc aacctctgcc
tcccaggttc aagtgattct cctgcctcag cctcctgagt agctgggatt
acaggtgcct gccatatgcc cagctaattt ttttgtatt tttagtagag
acagggtttc accatgttgg ccaggctggt ctcgaactcc tgaccttgtg
attctcccgc ctcaggctcc caaagtgctg ggattacagg catgagccac
tgcgcctggc tataactcct ctgtagtaaa aaatatattc cttcataatt
aatggcacaa tatttaaact ctgaattatt tttaagggat ggtagtggcc
tatgcaaaac tagctgtgga ataatgaatt ttaaaataag cagcatttaa
taaaaataga actatatttt ttttaaaata gaaaagccaa ctagaaggag
atataacaaa atgctaataa tggtgaaaat actggcatca ttcttctctg
cctctcatac ttttttcctat gaagtgttga ctacctttct aaaacacaaa
atcaaaaccg actaaaactc cagactaaca gtttcaaatt atattcagga
ggtttggctg aaagaaggag gaaaggtggg tgtgccctat ttggattcac
acaaaagtag ctccactttt ctcctttttt tttttgaga tggagtttcg
ctcttgctgt ccaggctgga gtgcaatggc acgatctcgg ctcaccgcaa
cctccacccc tcagattcaa gcaattctcc tgtctcagtc tcctgagtag
ctgggagtac aggcatgcac caccatgccc agctaatttt gtatgtttag
tggagacggg gtttctccat gttggtcaag ctggtctcta actccctacc
tcaggtgatc cgcccacctc agcctcccaa agtgctggga ttacaggcat
gagccacagt gctgggcctc acttttctcc attttacat ttagggtttg
gcccaagatt gtatttgttc tttggttatc atttgttcaa ctaataagta
actgaaacat gacctgattc aatgaacttc agagcctgcc ccaatcgttc
tgggaaactt caaatagggaa aactccttgt ccagactgac agattagcac
ctgccaaagg cagaatcctg caccagccaa tcctgggcac actttccagc
cccaattgta tggcatgggc ctatgattct atcccagttc ttaagaattc
tcagttaaaa tctgggaaca ataattccta cactataagg ctgttatgca
actaagaaaa aaagtaaga gcagttagca tatagcatat ctactcttat
gattattacc aatgaaaggc taaaactgtc acaaacttac ttacgttctt
tttcaaacag ctctctaaca ccaggcaaat cttttgctgc tccaaagtac
```

Fig. 7f

```
ttgtaacctc ggtttcctgg gacttctttt ccttcatgat ccagcatttt
agggccaact ttcttattgg gaagaaaaaa agagaaaatg gatctgttag
ttagttagtt agttattatt tatttattta tttgaggcgg agtctcgctc
tgttgcccat ttatttattt gaggtggagt ctcgctctgt tgcccaggct
ggagtgcagt agcacaatct cactgcaacc tccacctcct gggttcaagt
gattctcctg cctcagcctc ctgagtagct gggattacag gtgcgtgcca
ccacgcctgg ctaattttg tatttttagt agagacgggg tttcaccatg
ttggtcagga tggtcttgaa ctcctgacct catgatccac ccacctcgac
ctcccaaagt gctgggatta caggcgtgag ccaccgcgcc cggcattgtg
ggttttttt ttaatgctgt tgttttttgt ttgtgtgttt gttttcttt
tataataacc ctcaggccat tctatcatag gtctgctgaa gtttgctggg
ggtctggtcc agatcccagt tgccttgttt ttttcccata cctggactta
tcaccagtga agcctttaaa acagcaaaga tagtagcaag ctccttcctg
tggaagttcc atcccggggc ggttctgacc tgttgccaac ccacatgcat
caggaggttg ctggagaccc ccattgggag ggcttaccca gtcaggagga
acagaatcag tgacttaccc aaagaagcag tctgactgct ttttggtaga
gcagttgtgc tgcactctgg gagacccttc cttgtccaga cagcctgtat
tctccacagt ctgcatgctg gagcagctga atcaacagga ccacagagat
ggtggcagcc cttcccccag gaactccatc ccagggagag atcagagttt
tatctgtaga accctggctg gagtggctga agccctgca aggagatcct
gcccagtgag gaggaatgga tcgggatccc acgaacgggc tgatgaacta
ctgtccatcg ataggcgcnn nnnatagatt tcatgatgaa gttgacgcta
gtggtaacaa gttatataga acatgatcgt cctcatatgg cggagtttag
tgagcattgt gttccttttg tgagagtaaa gcttttatt aatgatagag
tgttatttg gtgaggtttt ttagggtgtg gcgagtgtgc gtatagccat
gtcttgaaaa tggggatgg gattagtatg atcagaaggg agttggggag
gaatcactgg tttgtaaatt gaggggaag ggcctatcta atgcaggaaa
caaggtggcc atgcgggagc tgatcagcag gccaaaattg tggggtgaat
ggagttaatt catagcaggg tttaaagagc ttatgtgggg acagatgaag
atttatcatg gtctagaatc atttcggagc tttgtttgcg tgtcaggccc
cgtgatatgt gcaagagcgc catcagtacg cgtcatggga gcatactgtt
ttcgggatgg gtttcgagcg aagatgtgag cagatactgc tgtcaatggt
gaagccttga ttagaggcac catatgcagt tcttcatgat gctttacatc
cataaaagcc tcggcagcgc ccagcaagag aattcagtgg tgctattcct
tttgaggtgg ggagtggagt atctctcgat cagcgcgtgt ttaccatgcc
ccagtcttag ttatcttcat gttcaaggtt ccggggcaa agtgattctc
ctacctcatc ctctagagta gttatgacta cagagcatgt tatcaccacg
accgggtaat gaaagtatta tagtagattg ggggtttaca ccatgttgga
caggatggta ttaatttcct gacctcatga tccgcctgcc tcccaaagtg
ctgagattac aggcgtgagc caccacgcct gccctaattt tgtgtttta
gtagagatgg agtttcactg tgttggtcag gctgatgtcc aactcctgac
ctcaggtgat cctcctgcct tggcgtccca aagtgctggg attacaggtg
tgagccactg tgcccatcct tgttttgtat tttctaaaag agatgtatct
tgtttaaata ttaaattata agatattcag gccttgcaaa ttgtctggat
tacactgtaa aagtaatcat ttatgtgcaa ataattcctt gagatcaata
gttaaatgag ctcaagctga tctgactaaa ttggagaaga tacaaaatga
```

Fig. 7g

```
agatggggag gaagtggtgc cataagcagc ctttttcttt tgaccatttt
atatgccttt tttttttttt ttttgagatg gagtttcact cttgtaaccc
acgttggagt gcaattgctt ggcttgcaac aacctccacc tcccgggttc
aagagattat cctgcctccg cctcctgagt agctgggatt ataggcatga
gccaccaagc ctggctaatt ttgcattttt agtagagacg gggtttctcc
ttcttggtga ggctggtctc gaactcccaa cctcaggtga accatcctcg
tcggcctccc aaagtgctgg gattacaggt gtgagccacc gtgccctgcc
cgccattcgt tttttttttt tttttttttt tttaattct gactcttctg
tggtggaaac cagcaaatac ttcacataat ttaggatgct aatactagta
cagttaaaag aatgattaca aagcagatac tatttcaaat tctgtaaaaa
tctgtttta atatccttca ctggctgttt gttctgacta gaaatgtttt
gtatatctga aagcaccagt aactcatagc catataattt ttttggtaat
atgttcatag gcaagtggca agagttagta gaaagatttc tctaagaatt
tatcctaaat cagattacac agagttgggg taagtgagta ttgtgttatt
ttcttttgta tatttgacaa tgggaacttt ttgaaactca acttcagtgt
aattttaagt cactaaattt gtccacaagt taatgattaa acagttactg
aaagtggaga accttgccat ttttcggact gcgttttggg tctttggcac
tgtggttagg ttagctaatt cgattatcca ctcaagtttt actcagttgg
aaatatgttt ttctagatga tggtgcctgt gcttaggttt gagaggatat
ttaaaatacg actttgtgtg ccattgtttg acagtggaat taagggtaaa
aatatttaga tatggaagtg tgaaaatgta gttgcattgt tttcattatg
ttctattcca tttcattcta ttttaagaat agcctcaatt tattttaga
ttgttacata agtacaaaat ccatttgctt tagtgggagt tttatttta
ttttaaaatg ataaccaatt aaaggagttt attatgaaat tctaagtagc
attgtttaaa atgtaaaatt acattacaga aacatttgga aaggggagaa
taaagaaaa caaaacacaa atgttgccag tgctgtaggt gctattatta
gcgctttggt gtaactcatg gtcgttttcc tactattttt attatacagt
catctcttgg tatctgtgaa gtggttccac aaactccctc aaataccaaa
atcctcctat gctcaagttc ccaatataaa atagtgtagt acttgcatta
caacctttgc acatcttccc atatacttta aaatcatctt tagattactt
ataataccta acacaatgta aatgctgaat aagtagttgt taacattgta
ttgtttaggg aataatggca agaaaagtct gcatgttcaa tacagatgca
acttttccac tgaatatttt tattccaagg ttggttgaag ccatggatgc
agaacccatg gatatagagg gcctactgta cttgtaccat ctagagataa
gatttgtatc ttgcatttgt tttaacatat ctgttctaag gaatatctca
gtcaccaggc aagtgctgca gtataactag gtactacgtc aggtgctaag
gttaagagag tatttccctt cactgactcc tcactccgag aatccatttt
acagcttcat tggtttgggt tattccaatt ttttgatgtg agtaaataaa
tgacttctat ttgcccaaaa taaagcttat ataggcctta taaccatgca
aatgtgtcca ttaagttgga cttggaatga gtgaatgagt attactgcca
gtgtgtgtgt gtgtgtgtgt gtgtgtgtgt gtgtgtgtct gtctgtctgt
ctgtctgtct gtctgtctgt ctgtctgcct gcctgcctgc ctgcctgcct
gcctgcctgg ctgcctgtct gcctgtctgc ctgcctgcct gcctgcctgc
ctgcctgtct gtctcacttt gtccctagg ctggagtgca gtggtatgat
ctcggctcac tgcaacctcc accccccggg ttcaagcgat tcttctgcct
cagcctcctg agtagctggg attacaggcg catgccgcca tgcccggctg
```

Fig. 7h

```
tttttttgtat ttttagtaga gacggggttt cgccatgttg gccagactgg
tctcaaactc ctgacctcag atggtccacc cgcttcagcc tcccaaagtg
ctaggattac aggcatgagc caccgtgccc agccactacc aattatttct
cttaatggat tttcattgac cctaaccctg taaattccat cacttttatc
aaggtgtata ttataataag tctataatac ccaatcatgt agttgtgtga
ttattttatt tttttgagac agagtctcaa tgttgcccag gctggagtac
agtggcacca tctcagctca ctgtaagctc cgcctcctgg gttcacacca
ttctcctgcc tcagcctccc aagtagctgg gattacaggc gcctgccact
tcaccgggct aattttttgt attttcgta gagacggggt ttcaccatgt
tagccaagat ggtctcgatc tcatgatcca cccacctcgg cctcccaaag
tgatgggatt actggcgtga gccaccatgc ccagctattt ttttaaccaa
tatattagct agcttttttc cccagaataa ttttccaaaa atacatttaa
tagagaataa aagttaaaag aactttcagt ggtttaatgc tgttactttt
aatatttcaa agatctgact gcagccatga gcagcaatga gtgcttcaag
tgtggacgat ctggccactg ggcccgggaa tgtcctactg gtggaggccg
tggtcgtgga atgagaagcc gtggcagagg tggttttacc tcggatagag
gtatttgtc gaatagaaaa atttgaagta cttcagtatt tgttagtatc
aagactggtc tgactagccg aattctttgt ttttgctcaa acaggtttc
cagtttgttt cctcgtctct tccagacatt tgttatcgct gtggtgagtc
tggtcatctt gccaaggatt gtgatcttca ggaggatggt aagtatttaa
cacttccttt tcataccct ctagagcttg gagaggtgag cacatgcaac
tgtgtatagc atttccacct ttgaggtttt gtattgtata atttaaaacg
taacactttg taaaggtttt atagtcttgg cctgtttctt ttccttattg
ttgaagcctg ctataactgc ggtagaggtg gccacattgc caaggactgc
aaggagccca agagagagcg agagcaatgc tgctacaact gtggcaaacc
aggccatctg gctcgtgact gcgaccatgc agatgagcag aaatgctatt
cttgtggaga attcggacac attcaaaaag actgcaccaa agtgaagtgc
tataggtaag gtgtcagaat gttgttagaa gaaaactcat tgcagagatt
cttccagaga tgaattagct ataaatggaa gggccttagt aaattcagtg
aaacttagct gtgaccagat aagaccaatt ttcagcatat gtaactggca
gtctatctgt atataattct gtattctgcc ctgatatcct gtggcttatg
gtacctgggc agttttcaca actggacttt tttaatatat aaaagtaaga
gtgttataat ttgaacttc cagagacttc atagaaagct ctgtaatata
cataaatctt ttatcatgta accagaaatc tttgcctgtt tgtgacatgt
aagtgtataa tttgataaat gttgttgtgt acatatctgt gaaaccttag
gggttaattg catgaaaaca aagatcaggc gttttgttct gcatggtgac
tgttgctttg gtagacagtt ttttctgag gcccattgtg aaaacttta
atttcttttt taggtgtggt gaaactggtc atgtagccat caactgcagc
aagacaagtg aagtcaactg ttaccgctgt ggcgagtcag ggcaccttgc
acgggaatgc acaattgagg ctacagccta attatttcc tttgtcgccc
ctcctttttc tgattgatgg ttgtattatt ttctctgaat cctcttcact
ggccaaaggt tggcagatag aggcaactcc caggccagtg agctttactt
gccgtgtaaa aggaggaaag gggtggaaaa aaaccgactt tctgcattta
actacaaaaa agtttatgt ttagtttggt agaggtgtta tgtataatgc
tttgttaaag aacccccttt ccgtgccact ggtgaatagg gattgatgaa
tgggaagagt tgagtcagac cagtaagccc gtcctgggtt ccttgaacat
```

Fig. 7i

```
gttcccatgt aggaggtaaa accaattctg gaagtgtcta tgaacttcca
taaataactt taattttagt ataatgatgg tcttggattg tctgacctca
gtagctatta aataacatca agtaacatct gtatcaggcc ctacatagaa
catacagttg agtgggagta aacaaaaaga taaacatgcg tgttaatggc
tgttcgagag aaatcggaat aaaagcctaa acaggaacaa cttcatcaca
gtgttgatgt tggacacata gatggtgatg gcaaaggttt agaacacatt
attttcaaag actaaatcta aacccagag taaacatcaa tgctcagagt
tagcataatt tggagctatt caggaattgc agagaaatgc attttcacag
aaatcaagat gttattttg tatactatat cacttagaca actgtgtttc
atttgctgta atcagttttt aaaagtcaga tggaagagc aactgaagtc
ctagaaaata gaaatgtaat tttaaactat tccaataaag ctggaggagg
aagggagtt tgactaaagt tctttttgtt tgtttcaaat tttcattaat
gtatatagtg caaaatacca tattaaagag gggaatgtgg aggactgaaa
gctgacagtt tggactttc ttttgtact taagtcatgt cttcaataat
gaaaattgct gttaaaagga tgtatgggat ttagatactt ttgcaaagct
atagaaaatt cactttgtaa tctgttataa taatgcccttt gagttctgtg
ttcagtctga acaggttttt tggtggtggt ggttttgttt tgttttggag
acggagtctc actcttgtcg cccaggctgg agtgcaggct ggctcactg
caacctccac ctcccgggtt caagcaattc tcctgcctca gcctcctgag
tagctgggat tacaggcacc cgccaccacc ccccgctaat tttttgtatt
tttatttta ttttatttt ttatttttt ttgagacaga gtgtcgctct
gttgcccagg ctggagtgta gtggtgcgat ctcggctcac tgcaagctcc
gcctcctggg ttcgcgccat tctcctgcct cagcctcctg agtagctggg
gctacaggta cccgccaccg cgcccagcta attttttttt tttgtatttt
tagtaaagac ggggtttcac ggtgttagcc aggatggtct caatctcctg
acctcgtgat ccgcccgcct tggcctccca aagtgctggg atcacaggcg
tgagccaccg cgcccggcct attttttgta tttttagtag agactgggtt
tcatcatgtt ggtcgggctg gtctccaact cctgacctca ggtgatccac
ctgccccgcc ccccaaagtg ctagtgttac aggtgcgagc caccgtgtcc
ggccgattct gaacagtttt aataccattg ctatttttgt gtttttcctg
ggcctttttt ctttttttt tttttttg agacagtctc gctctgttgc
ccaggctaga gtgcaatggt gcaatctcag ctcactggaa ccttcacccc
ccaccccac accctgttca agtaattctc ctgcctcagc ctcccaaata
gctgggatta caggtgtccg ccaccacacc cagctaattt ttgttatttt
tagtagagat ggggtttcac tgtgttggtc aggctggtct ccaactgttg
ccctcaggtg agccactgtg ccccacctttt tcctgggttt cataaggatc
tgaagtggtg gattccttgt ttttgctagt atctcattta gagttgagat
ggaccttaaa actcatctgt tttaactcac tttttaatag atgagttaaa
cttaatttac ttaaggatgt acagttagag cctggaactt caaccattat
tcactcccca tgccctgttt ccccccactt cgaaattaaa tgcggttagc
atcatatagt tcattttccc cctccatgct gctgtgtgat tcttgacttt
gggtatgagt ttttcatcct tcatgcaggg ttctgtcagt tcatggtata
```

Fig. 7j

A
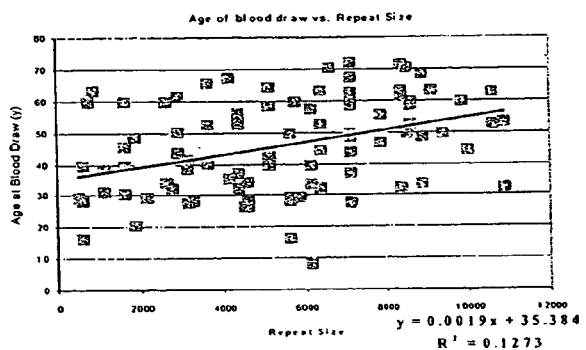
B
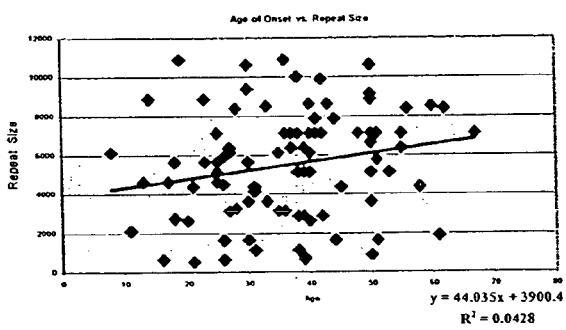
C
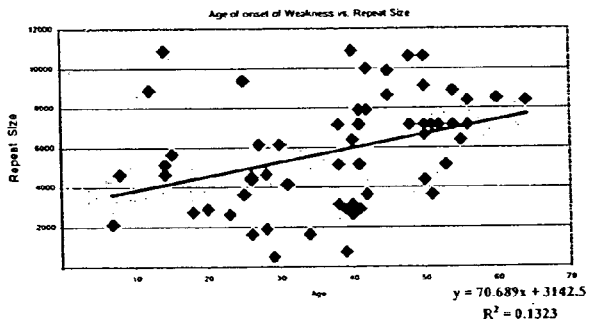
D
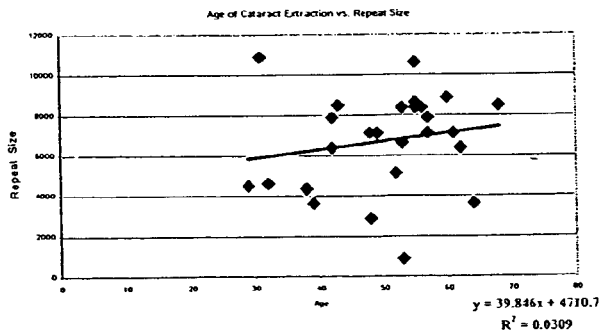
Fig. 8

SEQUENCE LISTING

```
<160> NUMBER OF SEQ ID NOS: 39

<210> SEQ ID NO 1
<211> LENGTH: 22400
<212> TYPE: DNA
<213> ORGANISM: homo sapiens
<220> FEATURE:
<221> NAME/KEY: misc_feature
<222> LOCATION: (14469)..(14473)
<223> OTHER INFORMATION: any nucleotide

<400> SEQUENCE: 1
actaatgaaa tgttcattaa atgatttgtc agtgtttcaa agtttctttta tcatcagtta     60 gcattcccta caccatcact ttagggagtc aatagaattt tataggagta ggcttcagta    120
agtactggga ggccagtagc actgttcaag cacatgggct gtctgtgttt gaagcctgac    180
ctgtcatttg ttcactttct gacttgagca gattacttaa actctctcga cctgtttctt    240
catggggata atacaagtac ttctaggggg tttgtgaaaa ctcataaaga ggttaaaaac    300
attgcctggc atacagtaag cacccaataa gaataagaaa taatatttgt atagtaatta    360
tgccagaaac tgttataaga gctgtatata tattaacaat tagctattac tagtattact    420
aattcctagt tcaggattta gcttagtaaa ctttctgctt cagaagcaaa tacgagaggt    480
gaaaacatca atttattctc ctcagtctta gttacatact ttccaagtca agtcacagag    540
cacaatttcc ttgctggcag ggacaagaca tgggtttaca tgatatcacc tatcccctca    600
atttaacagc atgtactatg cagttgggca tttaagcaga aattaagagt tggcaggtat    660
tgctcaactg gtacccattt taggaataat gctgaatcat agcattttat ctggtcttct    720
ctcaggatac ttaatgctaa tttttttgtat ttttagtaga gacgggattt caccttgtta    780
gccaggatgg tctcgatctc ctgacctcat gacccatctg cctcggcccc ccaaagtgct    840
```

```
gggattatag gcgtgatcca ccgtgcccgg acttttttttt tttttttttt tttgagacag    900
agtctccctc tgttgtgcag gctggagtgc agtggcccaa tctcttgctc ccaggtgcaa    960
gcgattctcc tgcctcagct tcccaagtag ctgggattac aggtgcccac caccacactc   1020
ggctaatttt tgtgttatta gtagagacaa gttttcacta tgttgcccag gctgctctca   1080
aactcctgac ctcaggtgat ccacctacct cggcctccca agtgctggga agttgttttt   1140
tttttctttt cttttttga gactgagtct tgctccgtca cccaggctgg agtgcagtgg    1200
cgtgatctcg gctcactgca agctctgcct ctcaggttca acgattctc ctgcctcaac    1260 ctctcgagta gcttggacta taggtccccg ccaccacgac cagctaattt tttgtatttt   1320
tagtagacag gatttcaccg tgttagccag gatggtcttg atcagctgac ctcgtgatcc   1380
gcccgcctcg gcctcccaaa gtgctggatt acaggcgtga ccaccgaacc cagccgaca    1440 cttaatactt tcttatggcc cttgttatcc tgcaagttct tcaagggcaa actctgtgtc   1500
ttaagtagtc acctttgtaa cccttgcaat gctgagcatg agactgaaca ctggaggaga   1560 ggagggaat aaaacatctc cagggaagag gaatgtaatg ggagcctctt caagtcccac    1620
tggcagctta tcttttgagt gagcttttc ctatttcaa acatttctag taaaataggc     1680
ataccaaagg gtatatccag gcaatacaag ccattgtagt taaattccac catacacctt   1740
ttctggcgcc tcacgatcag cctggctcta ttaataatag tcgttacagg aagctgcatg   1800
ccaggtagaa agagccatta gctgttacca ctccactgcc aagaagtaaa gacattgttt   1860
ccatttcttc tacttaagtc tttttaaaacc tatagaacat tatgtccagt atctctatct   1920
cacactcact ttcatttct atagctgttg aaatttttgt tttaatatta ggaatattcc    1980
attcctgggt ctataatgaa tagcaaacat tttatacagt actatggttg gaatggtaaa   2040
caaaaataag tcagaaaata ttaatttttg gccatatggt aattttaact tgtcctcttg   2100
gtgtggtgtg gacgcaccca ggttggactt catacatagc ctcttgcatt atattgactc   2160
attgtcagag ctcacgaagt cactacctaa gtgtctgatt gctacactat acattacttc   2220
aagatactat gaaggttaat cagattacaa aggggaaatc ataaagctga gtaagcttct   2280
tggtaataaa actatataaa tacaaaatac tgttttttat tggcagataa tatatcgtgt   2340
tttagcacaa cacataagct gctaggcatt tattcaatct gattgggaat gggttaaatt   2400
tggttaaaaa attttacctt aggttgcttt aattaaaaaa atgtttaagg ctgagtgcag   2460
tggctcacac ctgtaatcct agcactttgg gggcactggg tgcagtggct cacacctgta   2520
atcctagcac tttggcctag caccgcttga ggccaggagt tcaagcccag cctggccaac   2580
atgatgaaac cccatctcta ctaaaaatac aaaaattagc caggcgtggt ggtgggcgcc   2640
tgcagtccca gctactcagg aggctgaggc agaattggtc aaacatggga agcggaggtt   2700
gcagtgagct gagacagcac tccagcttgg gcaacagagg gagaccctgt ctcaaaaaat   2760
agtaataaat aaatttaaaa agttcggcca ggcgcggtgg ctcatgcctg taatcccagt   2820
gctttgggag gacgatcacc actttgggtg gcggatcac ctgaggtcgg agtttgaga    2880 ccagcctgac caacatggag aaaccccgcc tatactaaaa atacaaaatt agccgggcgt   2940
ggtggcgcat gcctataatc ccagctactg ggaggctga ggcaggagaa tcacttgaat    3000
ccaggaggcg gaggttgcag tgagctgaga tcgtgccatt gcactccagc ctgggcaacg   3060
gagtgagact ccgttctcaa aaaaaaaaa aagtttaaaa tatcattggt ctttaaagtt    3120
atacattcat tctttgataa ttgctatgtt gaacgcaacc tcctaactgc tttacaatga   3180
ttaagcacta atgatttgaa cccaggttta aagtctgact ctcaacacat gtgctctgcc   3240
```

```
ttctcacgaa catgatttca aaaatcatag ccccgggatt tgggattggt ggcttatgcc   3300
tgtaaaccca gcgacagagc aagaccctac tcttaaaaaa aaaaaaaatt aaagaaaaaa   3360
agaaaaataa atcatagtgt tgaactggca ggtttcactg agacgaaact tgggactctt   3420
ccttttttt tgtttcgaat aaagccattc tagaatgaga caaaattcta aatatttta   3480
tagttaacag tttaaattgg gtttaatctt gacaagacta tctagggcta tatacacaaa   3540
tctcttttgg agaaaatacc acaactaaac tgaagtctat tcctgaatat gacagaccag   3600
gtcaaatggt tatccttgcc ctcccggggg atgtcactca taaacgtgcc aaaagtcaca   3660
gtctaggccc cattacctta catgctcatg accttcccag ggaggcccct cgcccttacc   3720
aggcactttc atcttgggaa gacacatcag tcctggcgga gaaagcagca aggccttttcc  3780
ccggctcaca aaaattaata caaatctcag aggctgcatc ccacagccgt gaccaccgtg   3840
acttggcatc cccttttctg caaacttaaa tgttatctag aaatcgggcc tggctctgaa   3900
agccaagggc ctggcaggag cccgagaaag gggagaaact ttctgcggcc ccaagctaat   3960
ggcagtcact gcaccgagac ccgtcccctg catcccttt gctccagctg gccaagacag   4020
accaccaagg tcagccagat ttccaccag tctggccggg cccggaccca gctgggaatg   4080
aaccgagaag caccgggacc cggatcccgg cgtgaaaggc cgcgcgcggg gcacggcggg   4140
aaaagacgct gcgcgcagaa acacccgccc cgcgccgcgc tctagtgggc ggccctgccg   4200
cgggcggctc tgattggact gccgaacccc gcgcgctgat tggccgcgtg ggcgaggcgg   4260
aggagagccg tgcgcagcgg cgtatgtggg gccgtgtgca gacccgcgtg tggcgcaggc   4320
aaggaccctc aaaataaaca gcctctacct tgcgagccgt cttccccagg cctgcgtccg   4380
agtctccgcc gctgcgggcc cgctccgacg cggaaggtga gggctggggg aggggcccgg   4440
cgctgacgga gccgcagtgc gggtcgggtc tgtggcggac agagagggta gggagcggcg   4500
aggtggcgat ggcggccgca cttggcctg cgcctctgct gcgtcaggcg ggaagctcgg   4560
ctgctgccgc cgcctcggac ccgggtttct ggcgcaccgc tgtcggacga cacttctgtc   4620
cttctcttcgt cctggaaagc tgggtcgccg agcatgcggg tctttcggcg ccacggccgc   4680
accccaggcc gcaggcttag ggcagaggag gcccgcccgt gcgcccttgg ggccgaggcc   4740
ctgacgcttc gagggtcgcg gaatgaggga ccgaggtgg atttggcggg aactcactgg   4800
aaggagtccg tgtggtgggg aaaggctccc ggctgcggat gaagggggga tggggtgggt   4860
atagtcgtgc aggccatgtg ctgggtcgt gcgcctggcg ggccatgtgc caagggtttt   4920
ggggggcctta gaaaagggtt cttaggccgg gcgcggtggc tcacgcctgt aatcccagca   4980
ctttgagagt cccaggcggg cggatcacga ggtcaggagt tcgagaccag cctgaccaat   5040
atggtgaaag ttggtctgta ctaaaaataa aaaattagcc gggcatggtg gcgggcgcat   5100
gtagtcccag cagctcggga ggctggacag gagaatcgcg tgaacccgg aggccgaggt   5160
tgtggtgagc cgagatcgcg ccactacact ccagcatggg caacagagag agactccgtc   5220
ttaaaaaaac aaacaaacaa acaaacaaac aacaacaaag ggttcctgaa gaagcctttg   5280
tgtttggagt ggcgagactg ctggaagact tgggagcttt tagagtttat actccctatc   5340
cttgatagtt ttccgattct tgaattttta tcgtcattta aatactaagt tgcttgtgtt   5400
acattaccat tccaaaaggg gctgatgggg ctcacattcc aagagttaac actatttaag   5460
ttgctgggat ccttttaaaag cgccattacc agaaaaaaca cgaatttgtc aaacctccaa   5520
aaccacagca gcgggcggta gtctgcatca tttcttggat taatgaaaca gatgtaatta   5580
```

-continued

```
caaacgagac acgaaattca actagctccc ctccatctag attttttccat atcgtgagaa    5640 cctgttttag aatggcataa tggtccacat ttgggtttag gtgttgattt tattatgggt    5700
aaggcttgtg cttgttccca catgttaacc atatggcctc agccacaggg cacttccaaa    5760
ggaagtgact gtttctggtc ttgggggtct tgtaaaaaga gaacattgct cagtaatcgt    5820
ctgtgatttt agctagtgtg tttcaggcat tattcagaag gactcaggtg agataagcca    5880
aaactgaatt tgttttttgt ctttctcaaa gtgaaggagg tctaatgaat atccccatct    5940
tgcttttaaa ttacattttt aaaagtagat ttttccccct ttcctattgt ttgacccaat    6000
tttggagtga aacgtaacca gttactattt ccattcgaat ttaaattagc aattttatgt    6060
tatttgtttg ttcaagcagt ataactggag tgtagagctt tgagggtttc aaaaagataa    6120
gagatatagt acttatctcc tgggcttccc cctcccccct cctaaatagt tttaaatgct    6180
tctaatgagt tactctggtt aaggataatc aaacacctgt aaactgccag gatcctaggt    6240
acatgctgtt tttagtttgt tgagcctgat tcttgtctac aagagttctt tgtgtattgg    6300
aatataaaag gaataattta ttacattccc aagggcagaa ttaaagactt aagttttttcc    6360 gatttcatct cttgataagt ttttctttaa aaaaataaca gtttgtgttt ttctgaggaa    6420
ccaaaggtcc tcttttttttt catattggta acaggagagg taatgtattt cagatggtgc    6480
agtctgtaaa atattttgaa ccaaatcagt ggaagaccag gggttttttct ttttttttttt    6540 ctgagacgga gtctcactct gtcgcccaag ctggagtgca gtggcgcgat ctcggctcac    6600
tgcgacctcc gcctcccgga ttaagcgatt ctcctgcctc agcctccgaa gtagctggga    6660
ttacaggcgc ccgccgccac acccagctag ttttttgtatt ttagtacaga cggggtttca    6720
ccatgttggc caggctggtc tcgaactcct gaccttgtga tccgactccc tcggcctctc    6780
aaagtgctag gaaaacaggc aggagccacc gcgcctggcc aggtttttct taaactggca    6840
tttgaacatc tggaacaggc agggagatgt ctttttttaaa gtataaatgt gttttgttac    6900
atgatttatg acaattctac ttgtcttttt tttttttttt ttttttttgag acagagtctt    6960 tctctgtcgg ccaggctgga atgcagtggc acagtctcgg ctcacagcag cctccatctc    7020
ccgggctcaa gcaattctcc tgcctcagcc tcccaagtag ctgggattac agggcgtgtg    7080
ccaccacgcc cggctaattt ttgtattttt tgtaaagacg gggtttcacc atgttggcca    7140
ggctggtctt gatctcctga cctcaggtaa ttcacccgcc tcggcctccc aaagtgctgg    7200
gattacaggc ctgagccacc gtgccttgcc aacaattcta cttgtctttt aaagttcaat    7260
aaaaatatgt ggcacgtata tgggatagta ccaaactggt gcctaaaagc agtgaaacca    7320
ccattggact aattgaaatg atttgtctat tggctgaaga tttgaccaca gagagattct    7380 gcttttttttt ccttgcaggg atgaaaaatt aaaaaaaaaa aaaagattg gttcctttttt    7440 ctcttcctag cctcctgaca gtaagtagag agccagaaga atgatgccaa ggcatcctgg    7500
cctgctatgt ggagaacgct ctttccttac tgtctcactt aatagaactc ctgttctggc    7560
agtgtcagat gctgcagcag caagggaatg ccattgagtg attgcagtaa gctatgcagc    7620
attttcatgt ttaaaactac tgagataata agtgagaac ttgaggccac caaattttaa    7680
gttgtaatta gaaggatttt gttaattagg aatatgagag tgctacagtg atcacctgga    7740
atggctccat aaatacaaat gaggtgttaa ctagtgaagc aagttgccag tgtttgtgtg    7800
tttggtgaga ctcctaagtt ctgccatgaa gttaagaaaa atatttttta agattcaaga    7860
aagctgtgtg aatgaattca aaattattat gactgtagat cttttaaaaa gctatcagta    7920
ttagttttac tttgattttt atctaaagag aaatacagaa tgaatactta cagcattaca    7980
```

```
attcaaatgt gcgtggcttt ttttttttctt agttactaga tatatagtag taataccttt    8040
atgtaatatt ttgaagtaga gattgaattg gtataattcc ctaccttaaa aatattacac    8100
aatagcattt ttgtcatata ttacgatagc attttttgtgt actttaccac ttaactttt    8160 ttttcctttt cttttttttt tggagacaaa gtcttgctct gtcgcccagg cgggagtgca    8220
atggcaggat ctcagctcac tgcaacctct gcctcctggg tttaagccat tctcctgcct    8280
cagcctcctg agtagctggg actataggcg tgtgccacca cgcccggcta attttttgttt    8340 ttttagtttt ttttgagac ggagtctcgc tttgtcaccc acactggagt gcaaatggca    8400
tgatctcggc tcactgcagc ctccacctcc tgggttcaag cgattctctt gcctcatgca    8460
ccaccacgcc cagttaattt ttgtatattt agtagagatg gggtgtcact atgttggcca    8520
ggctgccgac ctcaagtgat cttccctcct cagcctccca aagtgctggg attacaggca    8580
tgagccactg cccctggcca gtgtcagatg tttagtttgt cattaaaatg gagcaagaat    8640
acataactcg tgaggttgta agattataga tatgtttact aatgactgac tcatagatat    8700
ccagctgtta aaactcttca agaagtaatc agggcaggcg gaaatggatg taattaacca    8760
aggtcaagca gtaagttcag gaaccaggat aaaaatacag aattgctccc gagtaagtac    8820
tctgttttcc attattctgg ctggaatgca ggtaatacag aaagtatatt gcttcctttc    8880
attgcttttt ttttcttctt tttttccttt gaggtggagt ttcgctcttg ttgcccaggc    8940
tggagtgcga tggcatgatc tcggctcacc gcaacctctg cctcctgggt tcaagcaatt    9000
cttgtgcgtc agcctcctga gtagctggga ttacaggcat gcaccaccat gtccagctaa    9060
tttttgtatt tttagtagag acagggtttc accatgttgg ctagctggtc tcgaactcct    9120
gacctcaggt gatgcatctg cctcggcctc ccaaaatgct gggattagag gtgtgggcca    9180
ccccgcccgg cccagacctt atcttgacta tcttagtcat ttcttctctt gcctgacatg    9240
ccctgtgctc ctaccaccct ttaaagtggt ttgtgtcata acatttgat acacaaaaat    9300 ggaaacttag gacaaatatc ttgatgtctg gtggttgaaa atgtgaactg atttggaaat    9360
caccggtgtt tctcctctta atctcttctc cattccattc aggaaataga ctgtaaggtg    9420
ggaaacaagt ataagcagtt agcctcactc taaacctgct atgtaataga cattggactg    9480
agttctgtct actctctgta agcaatccaa ggtaattggc gaaagtggaa ggaatatgta    9540
ctcagaagac caaaactttg gttttttaaat tgaatatcta ttaagcacaa ggtaacaatt    9600
cttaccacac acatcagttt tattatttcc cttttacaaa taagacacag atgggtagtc    9660
agatgtcttt gaggtaacac agcaagtagt taaactgggt taagtgatta acccaggttg    9720
agtatggttc caaaatctct tacagtgtca ggcaggctac atcagtgcag tatacgtaca    9780
tcaggtttca cgaaaaattt ttttccagaga aaacacaaac ccaaggaacc ttcagtaagt    9840
ggtgccttat attagtggtt tttagcaaaa ggaagaaact taagtgtttt cctgctgcct    9900
gacaaaagtg aaaaacagta ttttggtttt tattgaagtt agcatgtatg tttgtagctt    9960
gcataaaata gtactgaaat ccaattgatt atgaattctt ggactaacag aacctggatg   10020
acaaattaga ggttctggcc tggttgctgg ctttttttagt tgtcttgggt gtaaatttct   10080
cagccacacg tggggattgt gttagataat ctgaaatcta atttttcatgg ttttatgatt   10140 cagcagcttt cttcctttga tattttctag tatttgcttt attatagatt ggaatcctca   10200
aaataacatt gacaagtaga agatacttct gttagtggat ttaaaaaaaa attacattgg   10260
gaatgtcctt tgagtggttg gccctaatcc ctgtcagaag ctgaaagttg tggatcctaa   10320
```

```
attcatctgg gcagaatctc acctatgatt tcagaaagct gagagtttca gagagtgact    10380
gtagtcagtc cttagtgagt acaaaattga gaatacatca ttactttaaa ttaatggtgc    10440
agtaactctt gtgactgata gcaataattt aggtgctttg ttgttagtac ttgattagat    10500
tggattgggt cagttagttt caccaaattg ctaaagacac ctgtcccect agaattaaaa    10560
tactgagtta cataatggct actaaaagga taactatatg gggtgttcga tgattcaaag    10620
gtgaattact tggtctctac cttcaaggaa tatgatacaa ggcaatatgg tactgccatt    10680
agacagatat taacaaagtg tcttgggact taatagggag ggtagttcca ggctgggaga    10740
tgtagtcaga ttcttttata gagttggcat ttgagttggc ccgtgaaggt tggaaaaagt    10800
tgtgacaggt ggaaaaggag caggggagac caggacagtg cagtgaaatt ccagccagga    10860
gcagtcatag gcaatgagac agactcatgg agccatgatt ctcagctgtc ttaccttacc    10920
ttagttttcc taaggaatat catggaattc tgtaaagacc tttaaactaa ataatgttca    10980
tatgagatga gtgctaggat ggggacctgc tgcctaatat aagtagtgtg agtctaaaac    11040
attgtggaaa gtggttagtt taataatgtt attaaagaga caagtctatc acaagggacc    11100
agttaccagt gaaactgtag accacctgat tcactgcgat agggttagcc aaagggagga    11160
gagggcagat tgcatacata gtacctaagg ccactcaaag acctctttta aaatcacgtg    11220
tcatgttgat gacatttgga ggctattaat gttttcttc ccttttaaga cttagtgttt    11280
tctttattag cattaattta ctctagtaaa caaaattatg tgtgactaaa aatggcaaaa    11340
caggctgggc gcagtggctc acgcctgtaa tcctaacact tgggaggcc aaggcgggtg    11400
gatcactagg tcaggagatc gagaccatcc tggccaacat ggtgaaaccc cgtctctact    11460
aaaatacaaa aaattacctg gcgtggtgg tgcacgcctg tagtcccagc tatgtgggag    11520
gctgaggcag gggaatcgct tgaacccagg aggtgaaggt tgcagtgagc caagattggg    11580
ccaccgcact ccagcctggg acagagcgag actccatctc aaaaacaaaa aaagatcca    11640
aattagaaga acatggtggc atgcgcctgt agtcccagct acttgggagg ctgaggcagg    11700
agaattactt gaacccggga ggcagaggtt gcagtgagcc gagattgcac aactacactc    11760
cagcctgcgc aacagagcaa gactccatct caaaaaaaaa aaagaaaga aagaaagaaa    11820
gaaactggag ggaacaatgc cctaatgtat taacaatcat cacatatgag gtgtgaaaat    11880
gtgagtggtt ttttctgat tttctgtatt ttataacttt ttttgtttg agatggagtc    11940
ctgctctgct gcccaggctg gagcgcagtg gacgatctc ggctcactgc aacctctgcc    12000
tcccaggttc aagtgattct cctgcctcag cctcctgagt agctgggatt acaggtgcct    12060
gccatatgcc cagctaattt tttttgtatt tttagtagag acagggtttc accatgttgg    12120
ccaggctggt ctcgaactcc tgaccttgtg attctcccgc ctcaggctcc caagtgctg    12180
ggattacagg catgagccac tgcgcctggc tataactcct ctgtagtaaa aaatatattc    12240
cttcataatt aatggcacaa tatttaaact ctgaattatt tttaagggat ggtagtggcc    12300
tatgcaaaac tagctgtgga ataatgaatt ttaaaataag cagcatttaa taaaaatga    12360
actatatttt ttttaaaata gaaaagccaa ctagaaggga atataacaaa atgctaataa    12420
tggtgaaaat actggcatca ttcttctctg cctctcatac ttttccatat gaagtgttga    12480
ctacctttct aaaacacaaa atcaaaaccg actaaaactc cagactaaca gtttcaaatt    12540
atattcagga ggtttggctg aaagaaggag gaaaggtggg tgtgccctat ttggattcac    12600
acaaaagtag ctccactttt ctccttttt ttttttgaga tggagtttcg ctcttgctgt    12660
ccaggctgga gtgcaatggc acgatctcgg ctcaccgcaa cctccacccc tcagattcaa    12720
```

```
gcaattctcc tgtctcagtc tcctgagtag ctgggagtac aggcatgcac caccatgccc   12780 agctaattt  gtatgtttag tggagacggg gtttctccat gttggtcaag ctggtctcta   12840
actccctacc tcaggtgatc cgcccacctc agcctcccaa agtgctggga ttacaggcat   12900
gagccacagt gctgggcctc acttttctcc atttttacat ttagggtttg cccaagatt   12960 gtatttgttc tttggttatc atttgttcaa ctaataagta actgaaacat gacctgattc   13020
aatgaacttc agagcctgcc ccaatcgttc tgggaaactt caaataggga aactccttgt   13080
ccagactgac agattagcac ctgccaaagg cagaatcctg caccagccaa tcctgggcac   13140
actttccagc cccaattgta tggcatgggc ctatgattct atcccagttc ttaagaattc   13200
tcagttaaaa tctgggaaca ataattccta cactataagg ctgttatgca actaagaaaa   13260
aaaagtaaga gcagttagca tatagcatat ctactcttat gattattacc aatgaaaggc   13320
taaaactgtc acaaacttac ttcgttctt  tttcaaacag ctctctaaca ccaggcaaat   13380
cttttgctgc tccaaagtac ttgtaacctc ggtttcctgg gacttctttt ccttcatgat   13440
ccagcatttt agggccaact ttcttattgg gaagaaaaaa agagaaaatg gatctgttag   13500
ttagttagtt agttattatt tatttattta tttgaggcgg agtctcgctc tgttgcccat   13560
ttatttattt gaggtggagt ctcgctctgt tgcccaggct ggagtgcagt agcacaatct   13620
cactgcaacc tccacctcct gggttcaagt gattctcctg cctcagcctc ctgagtagct   13680
gggattacag gtgcgtgcca ccacgcctgg ctaatttttg tattttagt  agagacgggg   13740 tttcaccatg ttggtcagga tggtcttgaa ctcctgacct catgatccac ccacctcgac   13800
ctcccaaagt gctgggatta caggcgtgag ccaccgcgcc cggcattgtg gtttttttt    13860 ttaatgctgt tgttttttgt ttgtgtgttt gtttttcttt tataataacc ctcaggccat   13920
tctatcatag gtctgctgaa gtttgctggg ggtctggtcc agatcccagt tgccttgttt   13980
ttttcccata cctggactta tcaccagtga agcctttaaa acagcaaaga tagtagcaag   14040
ctccttcctg tggaagttcc atcccggggc ggttctgacc tgttgccaac ccacatgcat   14100
caggaggttg ctggagaccc ccattgggag ggcttaccca gtcaggagga acagaatcag   14160
tgacttaccc aaagaagcag tctgactgct ttttggtaga gcagttgtgc tgcactctgg   14220
gagacccttc cttgtccaga cagcctgtat tctccacagt ctgcatgctg gagcagctga   14280
atcaacagga ccacagagat ggtggcagcc ttcccccag  gaactccatc ccagggagag   14340
atcagagttt tatctgtaga accctggctg gagtggctga agcccctgca aggagatcct   14400
gcccagtgag gaggaatgga tcgggatccc acgaacgggc tgatgaacta ctgtccatcg   14460
atagggcgnn nnnatagatt tcatgatgaa gttgacgcta gtggtaacaa gttatataga   14520
acatgatcgt cctcatatgg cggagtttag tgagcattgt gttccttttg tgagagtaaa   14580 gcttttatt  aatgatagag tgttattttg gtgaggtttt ttagggtgtg gcgagtgtgc   14640
gtatagccat gtcttgaaaa tgggggatgg gattagtatg atcagaaggg agttggggag   14700
gaatcactgg tttgtaaatt gaggggggaag ggcctatcta atgcaggaaa caaggtggcc   14760
atgcgggagc tgatcagcag gccaaaattg tggggtgaat ggagttaatt catagcaggg   14820
tttaaagagc ttatgtgggg acagatgaag atttatcatg gtctagaatc atttcggagc   14880
tttgtttgcg tgtcaggccc cgtgatatgt gcaagagcgc catcagtacg cgtcatggga   14940
gcatactgtt ttcgggatgg gtttcgagcg aagatgtgag cagatactgc tgtcaatggt   15000
gaagccttga ttagaggcac catatgcagt tcttcatgat gctttacatc cataaaagcc   15060
```

```
tcggcagcgc ccagcaagag aattcagtgg tgctattcct tttgaggtgg ggagtggagt   15120
atctctcgat cagcgcgtgt ttaccatgcc ccagtcttag ttatcttcat gttcaaggtt   15180 ccggggggcaa agtgattctc ctacctcatc ctctagagta gttatgacta cagagcatgt   15240
tatcaccacg accgggtaat gaaagtatta tagtagattg ggggtttaca ccatgttgga   15300
caggatggta ttaatttcct gacctcatga tccgcctgcc tcccaaagtg ctgagattac   15360
aggcgtgagc caccacgcct gccctaattt tgtgttttta gtagagatgg agtttcactg   15420
tgttggtcag gctgatgtcc aactcctgac ctcaggtgat cctcctgcct tggcgtccca   15480
aagtgctggg attacaggtg tgagccactg tgcccatcct tgttttgtat tttctaaaag   15540
agatgtatct tgtttaaata ttaaattata agatattcag ccttgcaaa ttgtctggat    15600 tacactgtaa aagtaatcat ttatgtgcaa ataattcctt gagatcaata gttaaatgag   15660
ctcaagctga tctgactaaa ttggagaaga tacaaaatga agatggggag gaagtggtgc   15720
cataagcagc cttttttctt tgaccatttt atatgccttt tttttttttt ttttgagatg   15780
gagtttcact cttgtaaccc acgttggagt gcaattgctt ggcttgcaac aacctccacc   15840
tcccgggttc aagagattat cctgcctccg cctcctgagt agctgggatt ataggcatga   15900
gccaccaagc ctggctaatt ttgcattttt agtagagacg gggtttctcc ttcttggtga   15960
ggctggtctc gaactcccaa cctcaggtga accatcctcg tcggcctccc aaagtgctgg   16020
gattacaggt gtgagccacc gtgccctgcc cgccattcgt tttttttttt tttttttttt   16080
ttttaattct gactcttctg tggtggaaac cagcaaatac ttcacataat ttaggatgct   16140
aatactagta cagttaaaag aatgattaca aagcagatac tatttcaaat tctgtaaaaa   16200
tctgttttta atatccttca ctggctgttt gttctgacta gaaatgtttt gtatatctga   16260
aagcaccagt aactcatagc catataattt ttttggtaat atgttcatag gcaagtggca   16320
agagttagta gaaagatttc tctaagaatt tatcctaaat cagattacac agagttgggg   16380
taagtgagta ttgtgttatt ttcttttgta tatttgacaa tgggaacttt ttgaaactca   16440
acttcagtgt aattttaagt cactaaattt gtccacaagt taatgattaa acagttactg   16500
aaagtggaga accttgccat ttttcggact gcgttttggg tctttggcac tgtggttagg   16560
ttagctaatt cgattatcca ctcaagtttt actcagttgg aaatatgttt ttctagatga   16620
tggtgcctgt gcttaggttt gagaggatat ttaaaatacg actttgtgtg ccattgtttg   16680
acagtggaat taagggtaaa aatatttaga tatggaagtg tgaaaatgta gttgcattgt   16740
tttcattatg ttctattcca tttcattcta ttttaagaat agcctcaatt tattttttaga   16800 ttgttacata agtacaaaat ccatttgctt tagtgggagt tttattttta ttttaaaatg   16860
ataaccaatt aaaggagttt attatgaaat tctaagtagc attgtttaaa atgtaaaatt   16920
acattacaga aacatttgga aaggggagaa taaagaaaaa caaaacacaa atgttgccag   16980
tgctgtaggt gctattatta gcgctttggt gtaactcatg gtcgttttcc tactattttt   17040
attatacagt catctcttgg tatctgtgaa gtggttccac aaactccctc aaataccaaa   17100
atcctcctat gctcaagttc ccaatataaa atagtgtagt acttgcatta caacctttgc   17160
acatcttccc atatacttta aaatcatctt tagattactt ataataccta acacaatgta   17220
aatgctgaat aagtagttgt taacattgta ttgtttaggg aataatggca agaaaagtct   17280
gcatgttcaa tacagatgca acttttccac tgaatatttt tattccaagg ttggttgaag   17340
ccatggatgc agaacccatg gatatagagg gcctactgta cttgtaccat ctagagataa   17400
gatttgtatc ttgcatttgt tttaacatat ctgttctaag gaatatctca gtcaccaggc   17460
```

```
aagtgctgca gtataactag gtactacgtc aggtgctaag gttaagagag tattttcctt    17520
cactgactcc tcactccgag aatccatttt acagcttcat tggtttgggt tattccaatt    17580
ttttgatgtg agtaaataaa tgacttctat ttgcccaaaa taaagcttat ataggcctta    17640
taaccatgca aatgtgtcca ttaagttgga cttggaatga gtgaatgagt attactgcca    17700
gtgtgtgtgt gtgtgtgtgt gtgtgtgtgt gtgtgtctct gtctgtctgt ctgtctgtct    17760
gtctgtctgt ctgtctgcct gcctgcctgc ctgcctgcct gcctgcctgg ctgcctgtct    17820
gcctgtctgc ctgcctgcct gcctgcctgc ctgcctgtct gtctcacttt gtcccctagg    17880
ctggagtgca gtggtatgat ctcggctcac tgcaacctcc accccccggg ttcaagcgat    17940
tcttctgcct cagcctcctg agtagctggg attacaggcg catgccgcca tgcccggctg    18000
ttttttgtat ttttagtaga cggggtttt cgccatgttg ccagactgg tctcaaactc       18060 ctgacctcag atggtccacc cgcttcagcc tcccaaagtg ctaggattac aggcatgagc    18120
caccgtgccc agccactacc aattatttct cttaatggat tttcattgac cctaaccctg    18180
taaattccat cacttttatc aaggtgtata ttataataag tctataatac ccaatcatgt    18240
agttgtgtga ttatttttatt tttttgagac agagtctcaa tgttgcccag gctggagtac    18300
agtggcacca tctcagctca ctgtaagctc cgcctcctgg gttcacacca ttctcctgcc    18360
tcagcctccc aagtagctgg gattacaggc gcctgccact tcaccgggct aattttttgt    18420 attttcgta gagacggggt ttcaccatgt tagccaagat ggtctcgatc tcatgatcca     18480
cccacctcgg cctcccaaag tgatgggatt actggcgtga ccaccatgc ccagctattt      18540 ttttaaccaa tatattagct agcttttttc cccagaataa ttttccaaaa atacatttaa    18600
tagagaataa aagttaaaag aactttcagt ggtttaatgc tgttacttttt aatatttcaa    18660 agatctgact gcagccatga gcagcaatga gtgcttcaag tgtggacgat ctggccactg    18720
ggcccgggaa tgtcctactg gtggaggccg tggtcgtgga atgagaagcc gtggcagagg    18780
tggttttacc tcggatagag gtattttgtc gaatagaaaa atttgaagta cttcagtatt    18840
tgttagtatc aagactggtc tgactagccg aattctttgt ttttgctcaa acaggtttc     18900 cagtttgttt cctcgtctct tccagacatt tgttatcgct gtggtgagtc tggtcatctt    18960
gccaaggatt gtgatcttca ggaggatggt aagtatttaa cacttccttt tcatacccct    19020
ctagagcttg gagaggtgag cacatgcaac tgtgtatagc atttccacct ttgaggtttt    19080
gtattgtata atttaaaacg taacactttg taaaggtttt atagtcttgg cctgtttctt    19140
ttccttattg ttgaagcctg ctataactgc ggtagaggtg gccacattgc caaggactgc    19200
aaggagccca agagagagcg agagcaatgc tgctacaact gtggcaaacc aggccatctg    19260
gctcgtgact gcgaccatgc agatgagcag aaatgctatt cttgtggaga attcggacac    19320
attcaaaaag actgcaccaa agtgaagtgc tataggtaag gtgtcagaat gttgttagaa    19380
gaaaactcat tgcagagatt cttccagaga tgaattagct ataaatggaa gggccttagt    19440
aaattcagtg aaacttagct gtgaccagat aagaccaatt ttcagcatat gtaactggca    19500
gtctatctgt atataattct gtattctgcc ctgatatcct gtggcttatg gtacctgggc    19560
agttttcaca actggacttt tttaatatat aaaagtaaga gtgttataat ttgaacttc     19620 cagagacttc atagaaagct ctgtaatata cataaatctt ttatcatgta accagaaatc    19680
tttgcctgtt tgtgacatgt aagtgtataa tttgataaat gttgttgtgt acatatctgt    19740
gaaaccttag gggttaattg catgaaaaca aagatcaggc gttttgttct gcatggtgac    19800
```

```
tgttgctttg gtagacagtt tttttctgag gcccattgtg aaaactttta atttcttttt   19860
taggtgtggt gaaactggtc atgtagccat caactgcagc aagacaagtg aagtcaactg   19920
ttaccgctgt ggcgagtcag ggcaccttgc acgggaatgc acaattgagg ctacagccta   19980 attatttttcc tttgtcgccc ctccttttc tgattgatgg ttgtattatt ttctctgaat   20040
cctcttcact ggccaaaggt tggcagatag aggcaactcc caggccagtg agctttactt   20100
gccgtgtaaa aggaggaaag gggtggaaaa aaaccgactt tctgcattta actacaaaaa   20160
aagtttatgt ttagtttggt agaggtgtta tgtataatgc tttgttaaag aacccccttt   20220
ccgtgccact ggtgaatagg gattgatgaa tgggaagagt tgagtcagac cagtaagccc   20280
gtcctgggtt ccttgaacat gttcccatgt aggaggtaaa accaattctg aagtgtcta   20340 tgaacttcca taaataactt taattttagt ataatgatgg tcttggattg tctgacctca   20400
gtagctatta aataacatca agtaacatct gtatcaggcc ctacatagaa catacagttg   20460
agtgggagta aacaaaaaga taaacatgcg tgttaatggc tgttcgagag aaatcggaat   20520
aaaagcctaa acaggaacaa cttcatcaca gtgttgatgt tggacacata gatggtgatg   20580
gcaaaggttt agaacacatt attttcaaag actaaatcta aacccagag taaacatcaa   20640 tgctcagagt tagcataatt tggagctatt caggaattgc agagaaatgc attttcacag   20700
aaatcaagat gttatttttg tatactatat cacttagaca actgtgtttc atttgctgta   20760 atcagtttt aaaagtcaga tggaaagagc aactgaagtc ctagaaaata gaatgtaat   20820 tttaaactat tccaataaag ctggaggagg aaggggagtt tgactaaagt tcttttttgtt   20880 tgtttcaaat tttcattaat gtatatagtg caaaatacca tattaaagag gggaatgtgg   20940
aggactgaaa gctgacagtt tggacttttc tttttgtact taagtcatgt cttcaataat   21000
gaaaattgct gttaaaagga tgtatgggat ttagatactt ttgcaaagct atagaaaatt   21060
cactttgtaa tctgttataa taatgccctt gagttctgtg ttcagtctga acaggttttt   21120
tggtggtggt ggtttttgttt tgtttggag acggagtctc actcttgtcg cccaggctgg   21180
agtgcaggct tggctcactg caacctccac ctcccgggtt caagcaattc tcctgcctca   21240
gcctcctgag tagctgggat tacaggcacc cgccaccacc ccccgctaat ttttгтгтатт   21300 tttatttta ttttatttt ttattttttt ttgagacaga gtgtcgctct gttgcccagg   21360
ctggagtgta gtggtgcgat ctcggctcac tgcaagctcc gcctcctggg ttcgcgccat   21420
tctcctgcct cagcctcctg agtagctggg gctacaggta cccgccaccg cgcccagcta   21480 attттгтттт tttgtatttt tagtaaagac ggggtttcac ggtgttagcc aggatggtct   21540
caatctcctg acctcgtgat ccgcccgcct tggcctccca aagtgctggg atcacaggcg   21600
tgagccaccg cgcccggcct атттттгта ттттгтагтаг agactgggtt tcatcatgtt   21660
ggtcgggctg gtctccaact cctgacctca ggtgatccac ctgccccgcc ccaaagtg   21720 ctagtgttac aggtgcgagc caccgtgtcc ggccgattct gaacagtttt aataccattg   21780 ctaттттгт gtttttcctg ggccттттгт ctttttttt ttttttttg agacagtctc   21840 gctctgttgc ccaggctaga gtgcaatggt gcaatctcag ctcactgaa ccttcacccc   21900 ccacccccac accctgttca agtaattctc ctgcctcagc tcccaaata gctgggatta   21960 caggtgtccg ccaccacacc cagctaattt ttgttattt tagtagagat ggggtttcac   22020
tgtgttggtc aggctggtct ccaactgttg ccctcaggtg agccactgtg ccctttttt   22080 tcctgggttt cataaggatc tgaagtggtg gattccттгт тттгстадт atctcattта   22140 gagттgagат ggaccttaaa actcatctgt tttaactcac тттгtаатаг atgagttaaa   22200
```

```
cttaatttac ttaaggatgt acagttagag cctggaactt caaccattat tcactcccca    22260
tgccctgttt cccccactt cgaaattaaa tgcggttagc atcatatagt tcattttccc    22320
cctccatgct gctgtgtgat tcttgacttt gggtatgagt ttttcatcct tcatgcaggg    22380
ttctgtcagt tcatggtata                                                22400

<210> SEQ ID NO 2
<211> LENGTH: 26
<212> TYPE: DNA
<213> ORGANISM: homo sapiens

<400> SEQUENCE: 2
tgtctgcctg gctgcctgtc tgcctg                                         26

<210> SEQ ID NO 3
<211> LENGTH: 26
<212> TYPE: DNA
<213> ORGANISM: homo sapiens

<400> SEQUENCE: 3
tgtctgcctg tctgcctgtc tgcctg                                         26

<210> SEQ ID NO 4
<211> LENGTH: 18
<212> TYPE: DNA
<213> ORGANISM: homo sapiens

<400> SEQUENCE: 4
tgtctgcctg tctgcctg                                                  18

<210> SEQ ID NO 5
<211> LENGTH: 10
<212> TYPE: DNA
<213> ORGANISM: homo sapiens

<400> SEQUENCE: 5
tgtctgcctg                                                           10

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
gtgtgtgtgc atttgtgtgc                                                20

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
gaggttgcag tgagctgaat c                                              21

<210> SEQ ID NO 8
<211> LENGTH: 20
<212> TYPE: DNA
<213> ORGANISM: Artificial Sequence
<220> FEATURE:
```

<223> OTHER INFORMATION: primer

<400> SEQUENCE: 8
agctgaccct tgtcttccag                                    20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
caaacaaacc cagtcctcgt                                    20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
gcctagggga caaagtgaga                                    20

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
ggccttataa ccatgcaaat g                                  21

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
gctggcacct tttacaggaa                                    20

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
atttgccaca tcttcccatc                                    20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
gtgtgtaagg gggagactgg                                    20

```
<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
aagcccaagt ggcattctta                                               20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
tcattcccag acgtcctttc                                               20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
aatcgcttga acctggaaga                                               20

<210> SEQ ID NO 18
<211> LENGTH: 19
<212> TYPE: DNA
<213> ORGANISM: Artificial Sequence
<220> FEATURE:
<223> OTHER INFORMATION: primer

<400> SEQUENCE: 18
ctgccggtgg gttttaagt                                                19

<210> SEQ ID NO 19
<211> LENGTH: 20
<212> TYPE: DNA
<213> ORGANISM: Artificial Sequence
<220> FEATURE:
<223> OTHER INFORMATION: primer

<400> SEQUENCE: 19
tgcaagacgg tttgaagaga                                               20

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
agacactcaa ccgctgacct                                               20

<210> SEQ ID NO 21
<211> LENGTH: 20
<212> TYPE: DNA
<213> ORGANISM: Artificial Sequence
<220> FEATURE:
<223> OTHER INFORMATION: primer
```

<400> SEQUENCE: 21
gatctggaag tggagccaac                                              20

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
gagaaccttg ccattttcg                                               20

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
cacctacagc actggcaaca                                              20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
tgagccggaa tcataccagt                                              20

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
cctgaccttg tgatccgact                                              20

<210> SEQ ID NO 26
<211> LENGTH: 26
<212> TYPE: DNA
<213> ORGANISM: Artificial Sequence
<220> FEATURE:
<223> OTHER INFORMATION: primer

<400> SEQUENCE: 26
tgctttatta tagattggaa tcctca                                       26

<210> SEQ ID NO 27
<211> LENGTH: 21
<212> TYPE: DNA
<213> ORGANISM: Artificial Sequence
<220> FEATURE:
<223> OTHER INFORMATION: primer

<400> SEQUENCE: 27
aagacacctg tccccctaga a                                            21

<210> SEQ ID NO 28
<211> LENGTH: 20

```
<212> TYPE: DNA
<213> ORGANISM: Artificial Sequence
<220> FEATURE:
<223> OTHER INFORMATION: primer

<400> SEQUENCE: 28
gggtgacaga gcaagactcc                                              20

<210> SEQ ID NO 29
<211> LENGTH: 27
<212> TYPE: DNA
<213> ORGANISM: Artificial Sequence
<220> FEATURE:
<223> OTHER INFORMATION: primer

<400> SEQUENCE: 29
ttttaaacaa tgctacttag aatttca                                      27

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
gccgaattct tgtttttgc                                               20

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
ttgctgcagt tgatggctac                                              20

<210> SEQ ID NO 32
<211> LENGTH: 22
<212> TYPE: DNA
<213> ORGANISM: Artificial Sequence
<220> FEATURE:
<223> OTHER INFORMATION: primer

<400> SEQUENCE: 32
tgaatttact aaggcccttc ca                                           22

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
gtgctcacct ctccaagctc                                              20

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
```

```
gtagccatca actgcagcaa                                                     20

<210> SEQ ID NO 35
<211> LENGTH: 44
<212> TYPE: DNA
<213> ORGANISM: Artificial Sequence
<220> FEATURE:
<223> OTHER INFORMATION: primer

<400> SEQUENCE: 35
taatacgact cactataggg aggacgggct tactggtctg actc            44

<210> SEQ ID NO 36
<211> LENGTH: 41
<212> TYPE: DNA
<213> ORGANISM: Artificial Sequence
<220> FEATURE:
<223> OTHER INFORMATION: primer

<400> SEQUENCE: 36
tacgcatccg agtttgagac gcaggcaggc aggcaggcag g               41

<210> SEQ ID NO 37
<211> LENGTH: 21
<212> TYPE: DNA
<213> ORGANISM: Artificial Sequence
<220> FEATURE:
<223> OTHER INFORMATION: primer

<400> SEQUENCE: 37
tacgcatccg agtttgagac g                                     21

<210> SEQ ID NO 38
<211> LENGTH: 22
<212> TYPE: DNA
<213> ORGANISM: Artificial Sequence
<220> FEATURE:
<223> OTHER INFORMATION: probe

<400> SEQUENCE: 38
ttggacttgg aatgagtgaa tg                                    22

<210> SEQ ID NO 39
<211> LENGTH: 30
<212> TYPE: DNA
<213> ORGANISM: Artificial Sequence
<220> FEATURE:
<223> OTHER INFORMATION: primer

<400> SEQUENCE: 39
gccgcagtgc gggtcgggtc tgtggcggac                            30
```

INTRON ASSOCIATED WITH MYOTONIC DYSTROPHY TYPE 2 AND METHODS OF USE

CONTINUING APPLICATION DATA

This application is a divisional application of application Ser. No. 10/143,266, Confirmation No. 2285, filed on May 10, 2002, which claims the benefit of U.S. Provisional Application Ser. No. 60/290,365, filed May 11, 2001, U.S. Provisional Application Ser. No. 60/302,022, filed Jun. 29, 2001, and U.S. Provisional Application Ser. No. 60/337,831, filed Nov. 13, 2001, all of which are incorporated by reference herein.

GOVERNMENT FUNDING

The present invention was made with government support under Grant Number NS35870, awarded by the National Institutes of Health. The Government has certain rights in this invention.

BACKGROUND

DM is a dominantly-inherited, multisystemic disease with a consistent constellation of seemingly unrelated and rare clinical features including: myotonia, muscular dystrophy, cardiac conduction defects, posterior iridescent cataracts, and endocrine disorders (Harper, *Myotonic Dystrophy*, W. B. Saunders, London, ed. 2, 1989)). DM was first described nearly 100 years ago, but the existence of more than one genetic cause was only recognized after genetic testing became available for myotonic dystrophy type 1 (DM1) (Thornton et al., *Ann. Neurology*, 35, 269 (1994), Ricker et al., *Neurology*, 44, 1448 (1994)).

DM1 is caused by an expanded CTG repeat on chromosome 19 that is both in the 3' untranslated region of the dystrophia myolonica-protein kinase (DMPK) gene, and in the promoter region of the immediately adjacent homeodomain gene SIX5 (Groenen and Wieringa, *Bioessays*, 20, 901 (1998), Tapscott, *Science*, 289, 1701 (2000)). How the CTG expansion in a noncoding region of a gene causes the complex DM phenotype remains unclear. Suggested mechanisms include: (i) haploinsufficiency of the DMPK protein; (ii) altered expression of neighboring genes, including SIX5; and (iii) pathogenic effects of the CUG expansion in RNA which accumulates as nuclear foci and disrupts cellular function. Several mouse models have developed different aspects of DM1: a model expressing mRNA with CUG repeats manifests myotonia and the myopathic features of DM1; a DMPK knockout has cardiac abnormalities; and SIX5 knockouts have cataracts. Taken together, these data have been interpreted to suggest that each theory may contribute to DM1 pathogenesis and that DM1 may be a regional gene disorder.

To better define the pathophysiological cause of DM, we have studied families with many of the clinical features of DM but without the DM1 CTG expansion. After genetic testing became available for DM1, families with DM2 and Proximal Myotonic Myopathy (PROMM) were identified and linkage analysis excluded involvement of the DM1 locus, as well as excluding the muscle chloride and sodium channel genes. Proximal Myotonic Dystrophy (PDM) and Myotonic Dystrophy type 2 (DM2) were subsequently described, broadening the recognized phenotype of non-DM1 forms of dominantly inherited multisystemic myotonic disorders. In 1998 the DM2 locus was mapped to 3q21, and it was demonstrated that the genetic cause of PROMM map to the same locus in many families.

Defining a second human mutation that causes the multisystemic effects of DM, and identifying what is common to these diseases at the molecular level, provides an independent means of determining the pathogenic pathway of DM and allow methods for diagnosing this disease to be developed.

SUMMARY OF THE INVENTION

The present invention represents an advance in the art of detecting whether a human individual is at risk for myotonic dystrophy type 2 (DM2). The inventors have discovered that DM2 is caused by a CCTG expansion in intron 1 of the nucleotides encoding zinc finger protein 9 (ZNF9). This expansion is located in a region of the genome for which the nucleotide sequence was not completely ordered prior to the present invention. The correct sequence of this region has been determined and is disclosed herein. Accordingly, the present invention provides isolated polynucleotides. The polynucleotides include a nucleotide sequence of about nucleotides 1-14468 of SEQ ID NO:1, about nucleotides 14474-22400 of SEQ ID NO:1, about nucleotides 17501-17701 of SEQ ID NO:1, about nucleotides 17501-17701 of SEQ ID NO:1 and a repeat tract, about nucleotides 17858-18058 of SEQ ID NO:1, a repeat tract and about nucleotides 17858-18058 of SEQ ID NO:1, or the complements thereof. The present invention also provides isolated polynucleotides that include at least about 15 consecutive nucleotides from nucleotides 16701-17701 of SEQ ID NO:1, at least about 15 consecutive nucleotides from nucleotides 17858-18862 of SEQ ID NO:1, or the complements thereof.

The present invention provides a method for detecting a polynucleotide that includes a repeat tract within an intron 1 of a zinc finger protein 9 (ZNF9) genomic sequence. The method includes amplifying nucleotides of an intron 1 region of a ZNF9 genomic sequence to form amplified polynucleotides, wherein the amplified polynucleotides includes repeat tracts, and detecting the amplified polynucleotides. Alternatively, the method includes digesting genomic DNA with a restriction endonuclease to obtain polynucleotides, probing the polynucleotides under hybridizing conditions with a detectably labeled probe which hybridizes to a polynucleotide containing a repeat tract within an intron 1 of a ZNF9 genomic sequence, and detecting the probe which has hybridized to the polynucleotides.

The present invention further provides a method for identifying an individual not at risk for developing myotonic dystrophy type 2 (DM2). The method includes analyzing intron 1 regions of ZNF9 genomic sequences of an individual for two not at risk alleles that include repeat tracts of no greater than 176 nucleotides. For instance, the method may include amplifying nucleotides of intron 1 regions of ZNF9 genomic sequences of an individual to form amplified polynucleotides, wherein the amplified polynucleotides include repeat tracts, comparing the size of the amplified polynucleotides, and analyzing the amplified polynucleotides for two not at risk alleles. The act of amplifying may include performing a polymerase chain reaction (PCR) with a primer pair that includes a first primer and a second primer, wherein the first primer and the second primer flank the repeat tracts located within the intron 1 regions. The first primer includes at least about 15 nucleotides selected from nucleotides 14469-17701 of SEQ ID NO:1, and the second primer includes at least about 15 nucleotides selected from nucleotides 17858-18661 of SEQ ID NO:1. Alternatively, the method may include amplifying nucleotides of intron 1 regions within ZNF9 genomic sequences of an individual to form amplified polynucleotides, wherein the amplified polynucleotides include repeat tracts, and analyzing the repeat tracts of the amplified polynucleotides for two not at risk alleles including repeat tracts of no greater than 176 nucleotides.

Also provided by the present invention is a method for identifying an individual that has DM2 or is at risk for developing DM2. The method includes analyzing an intron 1 region of a ZNF9 genomic sequence of an individual for one at risk allele including a repeat tract including at least about 75 CCTG repeats. In another aspect, the method includes digesting genomic DNA of an individual with a restriction endonuclease to obtain polynucleotides, probing the polynucleotides under hybridizing conditions with a detectably labeled probe that hybridizes to a polynucleotide containing a repeat tract within an intron 1 of a ZNF9 genomic sequence, detecting the probe that has hybridized to the polynucleotide, and analyzing the intron 1 region of the hybridized polynucleotide for one at risk allele including a repeat tract including at least about 75 CCTG repeats. In yet another aspect, the method includes amplifying nucleotides of an intron 1 region of a ZNF9 genomic sequence of an individual to form amplified polynucleotides, wherein the amplified polynucleotides include a repeat tract, and analyzing the repeat tracts of the amplified polynucleotides for one at risk allele including a repeat tract including at least about 75 CCTG repeats.

The present invention also provides kits. In one aspect of the invention, the kit is for identifying whether an individual is not at risk for developing DM2. The kit includes a first primer having at least about 15 consecutive nucleotides selected from nucleotides 14469-17701 of SEQ ID NO:1, and the second primer having at least about 15 consecutive nucleotides selected from nucleotides 17858-18661 of SEQ ID NO:1. An individual who is not at risk has two not at risk alleles of ZNF9 genomic sequences including repeat tracts of no greater than 176 nucleotides.

In another aspect, the kit is for identifying whether an individual is at risk for developing DM2. The kit includes a probe having at least about 200 nucleotides, wherein the probe hybridizes to SEQ ID NO:1 or the complement thereof. An individual who is at risk has one at risk allele of a ZNF9 genomic sequence including a repeat tract including at least about 75 CCTG repeats. Alternatively, the kit includes a first primer having at least about 15 nucleotides selected from nucleotides 14469-17701 of SEQ ID NO:1 or nucleotides 17858-18661 of SEQ ID NO:1, and a second primer having a nucleotide sequence selected from the group consisting of $(CCTG)_n$ and $(CAGG)_n$, where n is at least 4. An individual who is at risk has one at risk allele of a ZNF9 genomic sequence including a repeat tract including at least about 75 CCTG repeats.

In yet another aspect, the kit is for identifying whether an individual has DM2. The kit includes a probe having at least about 200 nucleotides, wherein the probe hybridizes to SEQ ID NO:1 or the complement thereof. An individual who is at risk has one at risk allele of a ZNF9 genomic sequence including a repeat tract including at least about 75 CCTG repeats, and displays a symptom of DM2. Alternatively, the kit includes a first primer including at least about 15 nucleotides selected from nucleotides 14469-17701 of SEQ ID NO:1 or nucleotides 17858-18661 of SEQ ID NO:1, and a second primer including a nucleotide sequence selected from the group consisting of $(CCTG)_n$ and $(CAGG)_n$, where n is at least 4. An individual who is at risk has one at risk allele of a ZNF9 genomic sequence including a repeat tract including at least about 75 CCTG repeats.

Unless otherwise specified, "a," "an," "the," and "at least one" are used interchangeably and mean one or more than one.

BRIEF DESCRIPTION OF THE FIGURES

FIG. 7. Nucleotide sequence of a human zinc finger protein 9 (ZNF9) genomic sequence (SEQ ID NO:1). N, nucleotide A, C, T, or G.

FIG. 8. Correlation of Repeat Length with Clinical Severity.

DETAILED DESCRIPTION OF PREFERRED EMBODIMENTS OF THE INVENTION

Compositions

The present invention provides isolated polynucleotides that include a portion of an intron 1 region of a zinc finger protein 9 (ZNF9) genomic sequence. As used herein, the term "polynucleotide" refers to a polymeric form of nucleotides of any length, either ribonucleotides or deoxynucleotides, and includes both double- and single-stranded DNA and RNA. A polynucleotide may include nucleotide sequences having different functions, including, for instance, genomic sequences, and other sequences such as regulatory sequences and/or introns. A polynucleotide can be obtained directly from a natural source, or can be prepared with the aid of recombinant, enzymatic, or chemical techniques. A polynucleotide can be linear or circular in topology. A polynucleotide can be, for example, a portion of a vector, such as an expression or cloning vector, or a fragment. An "isolated" polypeptide or polynucleotide means a polypeptide or polynucleotide that has been either removed from its natural environment, produced using recombinant techniques, or chemically or enzymatically synthesized. Preferably, a polypeptide or polynucleotide of this invention is purified, i.e., essentially free from any other polypeptide or polynucleotide and associated cellular products or other impurities. As used herein, a "genomic sequence" includes a polynucleotide that encodes an unprocessed preRNA (i.e., an RNA molecule that includes both exons and introns), and the preRNA. When placed under the control of appropriate regulatory sequences, a genomic sequence produces an mRNA. The boundaries of a genomic sequence are generally determined by a transcription initiation site at its 5' end and a transcription terminator at its 3' end. A genomic sequence typically includes introns and exons. A regulatory sequence is a polynucleotide that regulates expression of a genomic sequence to which it is operably linked. A non-limiting example of a regulatory sequence includes promoters. "Operably linked" refers to a juxtaposition wherein the components so described are in a relationship permitting them to function in their intended manner. A regulatory sequence is "operably linked" to a genomic sequence when it is joined in such a way that expression of the genomic sequence is achieved under conditions compatible with the regulatory sequence.

Figure 4:
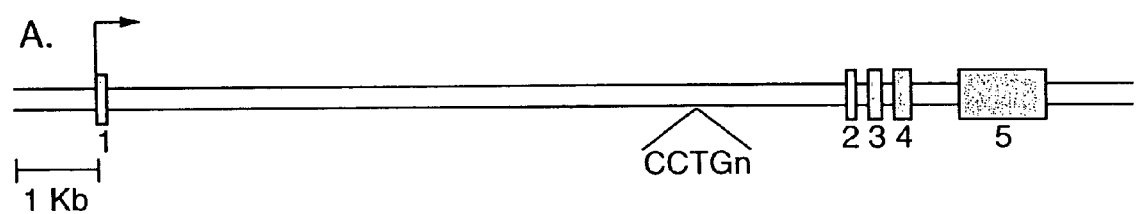
FIG. 4. Genomic organization of the ZNF9 gene. The position of the DM2 expansion in intron 1 is shown. The gene spans 16.5 kb of genomic sequence with an mRNA of 1.5 kb.

The ZNF9 genomic sequence maps to chromosome 3, position 3q21, in the human genome. The sequence tagged sites (STS) associated with the ZNF9 genomic sequence include N22238 and stG51107. The polypeptide encoded by the ZNF9 genomic sequence contains 7 zinc finger domains and functions as an RNA-binding polypeptide by binding the sterol regulatory element (see Rajavashisth et al. *Science*, 245, 640-643). As used herein, a "polypeptide" refers to a polymer of amino acids linked by peptide bonds and does not refer to a specific length of a polymer of amino acids. The ZNF9 genomic sequence contains 5 exons and 4 introns (see FIG. 4).

The sequence of a ZNF9 genomic sequence obtained from one individual is disclosed in FIG. 7. In this sequence, exon 1 corresponds to nucleotides 4337-4415, exon 2 corresponds to nucleotides 18662-18799, exon 3 corresponds to nucleotides 78896-18987, exon 4 corresponds to nucleotides 19156-19356, and exon 5 corresponds to nucleotides 19865-20845. Intron 1, which corresponds to nucleotides 4416-18661, includes a gap of unknown size. This gap is depicted in SEQ ID NO:1 between nucleotides 14469-14473. An intron 1 of a ZNF9 genomic sequence includes a TG/TCTG/CCTG repeat tract, which is also referred to herein as a "repeat tract." The characteristics of repeat tracts are described in greater detail below. In SEQ ID NO:1, the repeat tract corresponds to nucleotides 17702-17858. In the ZNF9 genomic sequence, the transcription initiation site is nucleotide 4337, the first nucleotide of exon 1, and the transcription termination site is nucleotide 20845.

An intron 1 of a ZNF9 genomic sequence typically includes at least about 14247 nucleotides. The sequences of an intron 1 immediately adjacent to exon 1 (i.e., the 5' end of intron 1) are preferably nucleotides 4416-4426 of SEQ ID NO:1, more preferably nucleotides 4416-4466 of SEQ ID NO:1, most preferably nucleotides 4416-4516 of SEQ ID NO:1. The sequences of an intron 1 immediately adjacent to exon 2 (i.e., the 3' end of intron 1) are preferably nucleotides 18641-18661 of SEQ ID NO:1, more preferably nucleotides 18611-18661 of SEQ ID NO:1, most preferably nucleotides 18561-18661 of SEQ ID NO:1. Intron I of a ZNF9 genomic sequence also includes several nucleotide sequences that are highly conserved by intron 1 regions present in different alleles of ZNF9, and preferably are not present elsewhere in the human genome. For instance, an intron 1 of a ZNF9 genomic sequence contains one, preferably two, more preferably 3, most preferably, 4 of the following: GCCGCAGT-GCGGGTCGGGTCTGTGGCGGAC (SEQ ID NO:39), the nucleotide sequence generated by using the primers GAGAACCTTGCCATTTTCG (SEQ ID NO:22) and CAC-CTACAGCACTGGCAACA (SEQ ID NO:23) to amplify an intron 1 of ZNF9, preferably SEQ ID NO:1, GCCTAGGG-GACAAAGTGAGA (SEQ ID NO:10), GGCCTTATAAC-CATGCAAATG (SEQ ID NO:1), or the complements thereof.

Examples of the polynucleotides of the present invention include polynucleotides located upstream (i.e., 5') or downstream (i.e., 3') of the repeat tract. Polynucleotides of the present invention located upstream of the repeat tract preferably include, in increasing order of preference, about nucleotides 17501-17701 of SEQ ID NO:1, about nucleotides 17101-17701 of SEQ ID NO:1, about nucleotides 16701-17701 of SEQ ID NO:1, most preferably, about nucleotides 15701-17701 of SEQ ID NO:1, or the complements thereof.

Polynucleotides of the present invention located downstream of the repeat tract preferably include, in increasing order of preference, about nucleotides 17858-18058 of SEQ ID NO:1, about nucleotides 17858-18458 of SEQ ID NO:1, about nucleotides 17858-18858 of SEQ ID NO:1, most preferably, about nucleotides 17858-19858 of SEQ ID NO:1, or the complements thereof.

Optionally and preferably, the polynucleotides of the invention that include a portion of SEQ ID NO:1 further include a repeat tract, or the complements thereof. More preferably, the polynucleotides of the invention include the repeat tract and polynucleotides located upstream and downstream of the repeat tract. The upstream nucleotide of such polynucleotides can begin at, in increasing order of preference, about nucleotide 17501, about nucleotide 17101, about nucleotide 16701, most preferably, about nucleotide 15701 of SEQ ID NO:1. The downstream nucleotide of such polynucleotides can end at, in increasing order of preference, about nucleotide 18058, about nucleotide 18458, about nucleotide 18858, most preferably, about nucleotide 19858 of SEQ ID NO:1.

The present invention also includes shorter polynucleotides, also referred to herein as primers and probes. A polynucleotide of this aspect of the invention has a nucleotide sequence that is complementary to a nucleotide sequence of a ZNF9 genomic sequence, or the complement thereof. Preferably, such a polynucleotide includes a nucleotide sequence of the intron 1 that flanks the repeat tract, exon 2, or the complements thereof, and optionally, further includes nucleotides of the repeat tract and the complements thereof. In some embodiments, a polynucleotide of this aspect of the invention includes consecutive nucleotides selected from about nucleotides 15701-16700 of SEQ ID NO:1, about nucleotides 16701-17100 of SEQ ID NO:1, about nucleotides 17101-17500 of SEQ ID NO:1, about nucleotides 17501-17701 of SEQ ID NO:1, about nucleotides 17858-18058 of SEQ ID NO:1, about nucleotides 18059-18458 of SEQ ID NO:1, about nucleotides 18459-18858 of SEQ ID NO:1, about nucleotides 18859-19858 of SEQ ID NO:1, SEQ ID NO:2, SEQ ID NO:3, SEQ ID NO:4, SEQ ID NO:5, or the complements thereof. A polynucleotide of this aspect of the invention includes, in increasing order of preference, at least about 15 consecutive nucleotides, at least about 20 consecutive nucleotides, at least about 25 consecutive nucleotides, at least about 200 nucleotides, at least about 350 nucleotides, most preferably, at least about 500 nucleotides.

Methods

The identification of a genomic sequence that is associated with a disease allows for unproved diagnosis of the disease. The present invention discloses that an expansion in the intron 1 of a ZNF9 genomic sequence is associated with the disease myotonic dystrophy type 2 (DM2). The expansion occurs in a TG/TCTG/CCTG (SEQ ID NO:40) repeat tract, also referred to herein as a "repeat tract." A repeat tract begins with at least about 14 consecutive TG nucleotides (i.e., the TG dinucleotide repeated 14 times), followed by at least about 3 consecutive TCTG nucleotides, followed by at least about 4 consecutive CCTG nucleotides. A "normal" repeat tract, also referred to herein as a "not at risk" repeat tract, includes no greater than about 176 nucleotides, more preferably no greater than 164, most preferably, no greater than 154 nucleotides, where the total number of nucleotides is determined by counting from the first nucleotide of the first TG to the last nucleotide of the last CCTG. When greater than 4 consecutive CCTG nucleotides are present in a repeat tract, preferably a normal repeat tract, intervening GCTG and/or TCTG nucleotides may also be present. Examples of normal repeat tracts are depicted at SEQ ID NO:2, SEQ ID NO:3, and SEQ ID NO:4 (see FIG. 2B) and at nucleotides 17702-17857 of SEQ ID NO:1. A ZNF9 genomic sequence containing a normal repeat tract is referred to herein as a "normal allele." As used herein, an "allele" of ZNF9 refers to one of several alternative forms of the nucleotide sequence that occupies the location of the ZNF9 genomic sequence on chromosome 3, position 3q21. An individual with two "normal" or "not at risk" alleles of ZNF9 will not display symptoms of DM2 during his or her lifetime, and is considered to be "not at risk."

An "at risk" repeat tract of a ZNF9 genomic sequence also includes consecutive TG nucleotides, preferably about 16, followed by consecutive TCTG nucleotides, preferably about 9, followed by consecutive CCTG nucleotides. The number of consecutive CCTG nucleotides, also referred to herein as "a CCTG repeat," is at least about 75 (i.e., the four nucleotides CCTG repeated at least about 75 times), more preferably at least about 100, most preferably, at least about 500. Typically, a CCTG repeat of an at risk allele is uninterrupted in that there are no other nucleotides present in the CCTG repeat. An example of an at risk repeat tract is depicted at SEQ ID NO:5 (see FIG. 2B). As used herein, "at risk" describes an individual having an allele of the ZNF9 genomic sequence that is associated with DM2. Herein, this includes an individual who may be manifesting at least one symptom of DM2, as well as an individual who may develop at least one symptom of DM2 in the future. An allele of the ZNF9 genomic sequence that is associated with DM2 is referred to herein as an "at risk allele." This mutation is dominant, thus an individual with an at risk allele of ZNF9 may display at least one symptom of DM2 during his or her lifetime. Typically, individuals have either two normal alleles or one normal allele and one at risk allele.

The present invention includes methods for detecting a polynucleotide including a repeat tract within an intron 1 of a ZNF9 genomic sequence, methods for identifying an individual not at risk for developing DM2, and methods for identifying an individual that has or is at risk for developing DM2. The methods of the present invention can involve known methods for detecting a specific polynucleotide, including detection of DNA or RNA, preferably, DNA. For instance, polymerase chain reaction (PCR) techniques can be used with primers that amplify all or a portion of a repeat tract. Alternatively, Southern blotting hybridization techniques using labeled probes can be used. The source of polynucleotides is a biological sample that includes genomic DNA and/or unprocessed RNA, preferably genomic DNA. As used herein, a "biological sample" refers to a sample of material (solid or fluid) obtained from an individual, including but not limited to, for example, blood, plasma, serum, or tissue. An individual can be a rat, mouse, human, chimpanzee, or gorilla, preferably human. Typically, the number of nucleotides in a repeat tract, including the number of CCTG repeats in a repeat tract, can be inferred by the approximate molecular weight of the detected polynucleotide containing the repeat tract. Other techniques, including nucleic acid sequencing, can also be used for determining the number of nucleotides in a repeat tract.

The present invention provides methods for detecting a polynucleotide including at least a portion of a repeat tract within an intron 1 of a ZNF9 genomic sequence. Preferably, the polynucleotide includes an entire repeat tract within an intron 1 of a ZNF9 genomic sequence. In one aspect, the method includes amplifying nucleotides within an intron 1 region of a ZNF9 genomic sequence of an individual to form amplified polynucleotides that include a repeat tract, and detecting the amplified polynucleotides. Preferably, nucleotides are amplified by PCR. In PCR, a molar excess of a primer pair is added to a biological sample that includes polynucleotides, preferably genomic DNA. The primers are extended to form complementary primer extension products which act as template for synthesizing the desired amplified polynucleotides. As used herein, the term "primer pair" means two oligonucleotides designed to flank a region of a polynucleotide to be amplified. One primer is complementary to nucleotides present on the sense strand at one end of a polynucleotide to be amplified and another primer is complementary to nucleotides present on the antisense strand at the other end of the polynucleotide to be amplified. The polynucleotide to be amplified can be referred to as the template polynucleotide. The nucleotides of a polynucleotide to which a primer is complementary is referred to as a target sequence. A primer can have at least about 15 nucleotides, preferably, at least about 20 nucleotides, most preferably, at least about 25 nucleotides. Typically, a primer has at least about 95% sequence identity, preferably at least about 97% sequence identity, most preferably, about 100% sequence identity with the target sequence to which the primer hybridizes. The conditions for amplifying a polynucleotide by PCR vary depending on the nucleotide sequence of primers used, and methods for determining such conditions are routine in the art.

The methods that include amplifying nucleotides within an intron 1 region of a ZNF9 genomic sequence may be used to identify an individual not at risk for developing DM2. In this aspect, the primer pair includes primers that flank a repeat tract. The first primer includes at least about 15 consecutive nucleotides selected from about nucleotides 17501-17701 of SEQ ID NO:1, about nucleotides 17101-17701 of SEQ ID NO:1, about nucleotides 16701-17701 of SEQ ID NO:1, most preferably, about nucleotides 15701-17701 of SEQ ID NO:1. The second primer includes at least about 15 consecutive nucleotides selected from the complement of about nucleotides 17858-18058 of SEQ ID NO:1, about nucleotides 17858-18458 of SEQ ID NO:1, about nucleotides 17858-18858 of SEQ ID NO:1, most preferably, about nucleotides 17858-19858 of SEQ ID NO:1. In a preferred embodiment of this aspect of the invention, one primer includes the nucleotide sequence GGCCTTATAACCATGCAAATG (SEQ ID NO:11) and the second primer includes the nucleotide sequence GCCTAGGGGACAAAGTGAGA (SEQ ID NO:10).

After amplification, the sizes of the amplified polynucleotides may be determined, for instance by gel electrophoresis, and compared. The amplified polynucleotides can be visualized by staining (e.g., with ethidium bromide) or labeling with a suitable label known to those skilled in the art, including radioactive and nonradioactive labels. Typical radioactive labels include $^{33}$P. Nonradioactive labels include, for example, ligands such as biotin or digoxigenin as well as enzymes such as phosphatase or peroxidases, or the various chemiluminescers such as luciferin, or fluorescent compounds like fluorescein and its derivatives.

Due to the size of the expansion of CCTG repeats in an at risk allele, this method of amplifying nucleotides within an intron 1 region of a ZNF9 genomic sequence typically does not result in detectable amplified polynucleotides from an at risk allele. Thus, when the comparison of the sizes of the amplified polynucleotides indicates the presence of two polynucleotides, both copies of the individual's repeat tracts were amplified and the individual is considered to be not at risk (see, for instance, FIG. 6B, lane 1). When only one amplified polynucleotide is present after amplification as described above, it is not possible to conclude that the individual is not at risk (see, for instance, FIG. 6B, lanes 2 and 3).

Instead of comparing the sizes of the amplified polynucleotides after amplification, the size of the repeat tracts of the amplified polynucleotides may be determined by, for instance, inferring the size of the repeat tract based on the observed molecular weight of the amplified polynucleotides, or by determining the nucleotide sequence of the repeat tract. The presence of repeat tracts having no greater than 176 nucleotides, and no repeat tract having at least about 75 CCTG repeats, indicates the individual is not at risk. The presence of a repeat tract having at least about 75 CCTG repeats indicates the individual is at risk.

Alternatively, the methods that include amplifying nucleotides within an intron 1 region of a ZNF9 genomic sequence may be used to identify an individual that has or is at risk for developing DM2. In this aspect, the primer pair includes a first primer having a target sequence that does not include the repeat tract. The first primer includes at least about 15 consecutive nucleotides located either upstream or downstream of a repeat tract. When selected from nucleotides upstream of a repeat tract, the nucleotides are, in increasing order of preference, about nucleotides 17501-17701 of SEQ ID NO:1, about nucleotides 17101-17701 of SEQ ID NO:1, about nucleotides 16701-17701 of SEQ ID NO:1, most preferably, about nucleotides 15701-17701 of SEQ ID NO:1. When selected from nucleotides downstream of a repeat tract, the nucleotides are, in increasing order of preference, the complement of about nucleotides 17858-18058 of SEQ ID NO:1, about nucleotides 17858-18458 of SEQ ID NO:1, about nucleotides 17858-18858 of SEQ ID NO:1, most preferably, about nucleotides 17858-19858 of SEQ ID NO:1. The second primer of the primer pair includes either $(CCTG)_n$ or $(CAGG)_n$, where n is at least 4, preferably, at least 5. The second primer binds randomly at multiple sites within a repeat tract, which results in amplified polynucleotides that vary in size but are larger than the amplified polynucleotides that contain a normal allele. Thus, after determining the sizes of the amplified polynucleotides, the presence of one amplified polynucleotide and a population of amplified polynucleotides having a range of sizes that are greater than the one amplified polynucleotide indicates the individual has an at risk allele, and is considered to be at risk (see FIG. 6D and Example 2).

Optionally and preferably, the second primer of this aspect of the invention is modified to increase the efficiency of the amplification. The modification includes adding an additional nucleotide sequence present at the 5' end of the second primer. Such a nucleotide sequence is referred to herein as a "hanging tail" sequence. A hanging tail sequence includes at least about 20 nucleotides, more preferably at least about 22 nucleotides, and negligible complementarity to any nucleotide sequences in the human genome. Whether a hanging tail has negligible complementarity to any nucleotide sequences in the human genome can be determined by hybridizing the hanging tail sequence with the human genome under the hybridization conditions described herein. A hanging tail has negligible complementarity to any nucleotide sequences in the human genome when it does not hybridize to the human genome. When the second primer of this aspect of the invention is modified in this way, the amplification also includes a third primer having a nucleotide sequence such that it is complementary to the hanging tail nucleotide sequence when incorporated into an amplified polynucleotide. In a preferred embodiment of this aspect of the invention, the first primer is CL3N58-D R (5'-GGCCTTATAACCATGCAAATG (SEQ ID NO:11)), the second primer is JJP4CAGG (5'-TACG-CATCCGAGTTTGAGACGCAGGCAGGCAG- GCAGGCAGG (SEQ ID NO:36)), and the third primer is JJP3(5'-TACGCATCCGAGTTTGAGACG (SEQ ID NO:37)).

In another aspect of the methods for detecting a polynucleotide including a repeat tract within an intron 1 of a ZNF9 genomic sequence, polynucleotide probes are used that hybridize to a polynucleotide. As used herein, "hybridizes," "hybridizing," and "hybridization" means that a probe forms a noncovalent interaction with a target polynucleotide under standard conditions. Standard hybridizing conditions are those conditions that allow a probe to hybridize to a target polynucleotide. Such conditions are readily determined for a probe and the target polynucleotide using techniques well known to the art, for example see Sambrook et al. *Molecular Cloning: A Laboratory Manual;* Cold Spring Harbor Laboratory: New York (1989). Preferred probes useful in the present invention hybridize to a target polynucleotide by using prehybridization in a hybridization buffer, preferably RAPID-HYB buffer (Amersham, Piscataway, N.J.), at 60° for 1 hour, and hybridization overnight at 60° C. Preferably, at least $4\times10^7$ counts per minute (cpm) total of the labeled probe is used in the hybridization. When the probe used is at least about 200 nucleotides, the wash conditions used are: 2 washes for 5 minutes each at room temperature in a solution containing 2×SSC (one liter of 20×SSC contains 175.3 grams NaCl and 88.2 grams sodium citrate, pH 7.0) and 0.05% sodium dodecyl sulfate (SDS), followed by 2 to 3 washes for 30 minutes each at 52° in a solution containing 0.15×SSC and 0. 1% SDS. Other hybridization conditions for use when the probe is at least about 200 nucleotides use the same prehybridization and hybridization conditions as described above, but the wash conditions used are: 2 washes for 5 minutes each at room temperature in a solution containing 2×SSC and 0.05% SDS, followed by 1 wash for 15 minutes at 50° C. in a solution containing 0.15×SSC and 0.1% SDS, followed by 1 wash for 10 minutes at 50° C. in a solution containing 0.15× SSC and 0.1% SDS. When the probe used is about 20 to about 22 nucleotides, the same prehybridization and hybridization conditions described above are used, but the wash conditions used are: two 15 minute washes at 45° C. in 2×SSC and 0.1% SDS. The nucleotide sequence of a target DNA molecule is generally a sequence complementary to the probe. The hybridizing probe may contain 1 to 10 nonhybridizing nucleotides, preferably no greater than 5, more preferably no greater than 2 nonhybridizing nucleotides, that do not interfere with forming the noncovalent interaction. The nonhybridizing nucleotides of a probe may be located at an end or within the hybridizing probe. Thus, a probe does not have to be complementary to all the nucleotides of the target DNA sequence as long as there is hybridization under standard hybridization conditions. In increasing order of preference, a probe has at least about 20 nucleotides, at least about 200 nucleotides, at least about 350 nucleotides, most preferably at least about 500 nucleotides. Preferred polynucleotides useful in this aspect of the invention include TTGGACTTGGAATGAGTGAATG (SEQ ID NO:38), and nucleotides 16507-16992 of SEQ ID NO:1.

In one embodiment of this aspect of the invention, the methods include identifying an individual that has or is at risk for developing DM2. The method includes digesting genomic DNA of an individual with a restriction endonuclease to obtain polynucleotides, and probing the polynucleotides under hybridizing conditions with a detectably labeled probe. The digestion of genomic DNA with endonucleases is routine in the art, and numerous endonucleases are known. Preferred restriction endonuclease enzymes include EcoRI and BsoBI. Typically, the polynucleotides resulting from digestion are fractionated, for instance by gel electrophoresis, denatured to yield single stranded polynucleotides, and then exposed to the probe under hybridizing conditions. The probe that has hybridized to the polynucleotide is then detected, and the size of the hybridized polynucleotide may then be determined. The repeat tract may then be characterized, preferably by determining the number of CCTG repeats in the repeat tract. Typically, the number of nucleotides in a repeat tract, including the number of CCTG repeats in a repeat tract, can be inferred by the approximate molecular weight of the detected polynucleotide containing the repeat tract. The presence of one repeat tract having at least about 75 CCTG repeats indicates the individual is at risk.

In another embodiment of this aspect of the invention, polynucleotides may be used for in situ hybridization of tissue samples, preferably muscle tissue or fibroblasts, more preferably muscle tissue. Preferably, the muscle tissue is skeletal muscle. This method routine and known in the art (see, for instance, Taneja et al., *J. Cell. Biol.,* 128, 995-1002 (2002)). Preferred polynucleotides useful in this aspect of the invention include $(CAGG)_n$, where n is at least 4, preferably, at least 5. Preferably, such a polynucleotide includes a fluorescent label. The cells of an individual having an at risk allele will include numerous nuclei containing the fluorescent labeled polynucleotide, while the cells of an individual not having an at risk allele will not include nuclei containing the fluorescent labeled polynucleotide.

The present invention also provides a kit for identifying whether an individual as at risk or not at risk for developing DM2. The kit includes the primers and/or probes discussed above in a suitable packaging material in an amount sufficient for at least one assay. Optionally, other reagents such as buffers and solutions needed to practice the invention are also included. Instructions for use of the packaged polypeptide or primer pair are also typically included.

As used herein, the phrase "packaging material" refers to one or more physical structures used to house the contents of the kit. The packaging material is constructed by well known methods, preferably to provide a sterile, contaminant-free environment. The packaging material has a label which indicates that the polynucleotides can be used for identifying whether an individual as at risk or not at risk for developing DM2. In addition, the packaging material contains instructions indicating how the materials within the kit are employed. As used herein, the term "package" refers to a solid matrix or material such as glass, plastic, paper, foil, and the like, capable of holding within fixed limits the primers and/or probes. Thus, for example, a package can be a glass vial used to contain milligram quantities of a primer pair. "Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

The present invention is illustrated by the following examples. It is to be understood that the particular examples, materials, amounts, and procedures are to be interpreted broadly in accordance with the scope and spirit of the invention as set forth herein.

EXAMPLES

Example 1

Identification of the Molecular Basis for Myotonic Dystrophy Type 2

The myotonic dystrophy type 2 locus (also referred to as proximal myotonic myopathy (PROMM) locus) was previously mapped to chromosome 3q21 (Ranum et al., *Nature Genet.*, 19, 196 (1998), Day et al., *Neuromuscul. Disord.*, 9, 19 (1999)). Positional cloning was used to identify the DM2 mutation. We identified, obtained informed consent, performed neurological exams, and collected blood samples from DM2/PROMM family members. Genomic DNA was isolated from blood using the Puregene kit #D-5000 (Gentra Systems., Minneapolis, Minn.). Linkage analysis was performed using the LINKAGE package of computer programs (version 5.1) (Lathrop et al., *Proc. Natl. Acad. Sci. U.S.A.* 81, 3443 (1984)).

The DM2 region was narrowed to a 2 centiMorgan (cM) interval by analyzing 10 recombinant chromosomes (Ranum et al., *Nature Genet.*, 19, 196 (1998)). Sequence data from this region, which is partially covered by 14 BACs, was used to develop 80 short tandem repeat (STR) markers. The sequence data was from McPherson et al., (*Nature* 409, 934 (2001)), and BACs spanning the DM2 region were identified and ordered by sequence tagged site (STS) content mapping. Additional polymorphic STR markers were developed using di-, tri-, and tetranucleotide repeat sequences that mapped to the region (McPherson et al., *Nature* 409, 934-41 (2001)). PCR primers for the following markers were as follows: CL3N49 (CL3N49 F 5'-GTGTGTGTGCATTTGTGTGC (SEQ ID NO:6), CL3N49 R 5'-GAGGTTGCAGTGAGCT-GAATC (SEQ ID NO:7)); CL3N88 (CL3N88 F 5'-AGCT-GACCCTTGTCTTCCAG (SEQ ID NO:8), CL3N88 R 5'-CAAACAAACCCAGTCCTCGT (SEQ ID NO:9)); CL3N58 (CL3N58-D F 5'-GCCTAGGGGACAAAGT-GAGA (SEQ ID NO:10), CL3N58-D R 5'-GGCCT-TATAACCATGCAAATG (SEQ ID NO:11)); CL3N59 (CL3N59 F 5'-GCTGGCACCTTTTACAGGAA (SEQ ID NO:12), CL3N59 R 5'-ATTTGCCACATCTTCCCATC (SEQ ID NO:13)); CL3N83 (CL3N83 F 5'-GTGTG-TAAGGGGGAGACTGG (SEQ ID NO:14), CL3N83 R 5'-AAGCCCAAGTGGCATTCTTA (SEQ ID NO:15)); CL3N84 (CL3N84 F 5'-TCATTCCCAGACGTCCTTTC (SEQ ID NO:16), CL3N84 R 5'-AATCGCTTGAACCTG-GAAGA (SEQ ID NO:17)); CL3N99 (CL3N99 F 5'-CTGC-CGGTGGGTTTTAAGT (SEQ ID NO:18), CL3N99 R 5'-TGCAAGACGGTTTGAAGAGA (SEQ ID NO:19)); CL3N9 (CL3N9 F 5'-AGACACTCAACCGCTGACCT- (SEQ ID NO:20), CL3N9 R 5'-GATCTGGAAGTGGAGC-CAAC (SEQ ID NO:21)).

Linkage disequilibrium analysis was performed on 64 parent-offspring trios in which affected individuals had the clinical features of DM, which include myotonia, muscular dystrophy, cardiac conduction defects, posterior iridescent cataracts, and endocrine disorders (Harper, Myotonic Dystrophy, ed. 2, Saunders, London, (1989).), but not the DM1 mutation. Transmission disequilibrium testing (TDT) (Spielman et al., *Am. J. Hum. Genet.*, 52, 506 (1993)), which was performed using the GENEHUNTER program (version 1.0) (Kruglyak et al., *Am. J. Hum. Genet.*, 58, 1347 (1996)), and analysis of conserved ancestral haplotypes narrowed the DM2 locus to ~320 kilobases (kb) (FIG. 1A). Genbank accession numbers for the three BACs spanning the region of linkage disequilibrium were as follows: RP11-814L21 (AC022944); RP11-723o4 (AC022993); and RP11-221e20 (AC023598).

Expanded CL3N58 Allele Found in DM2 Patients

Figure 1:
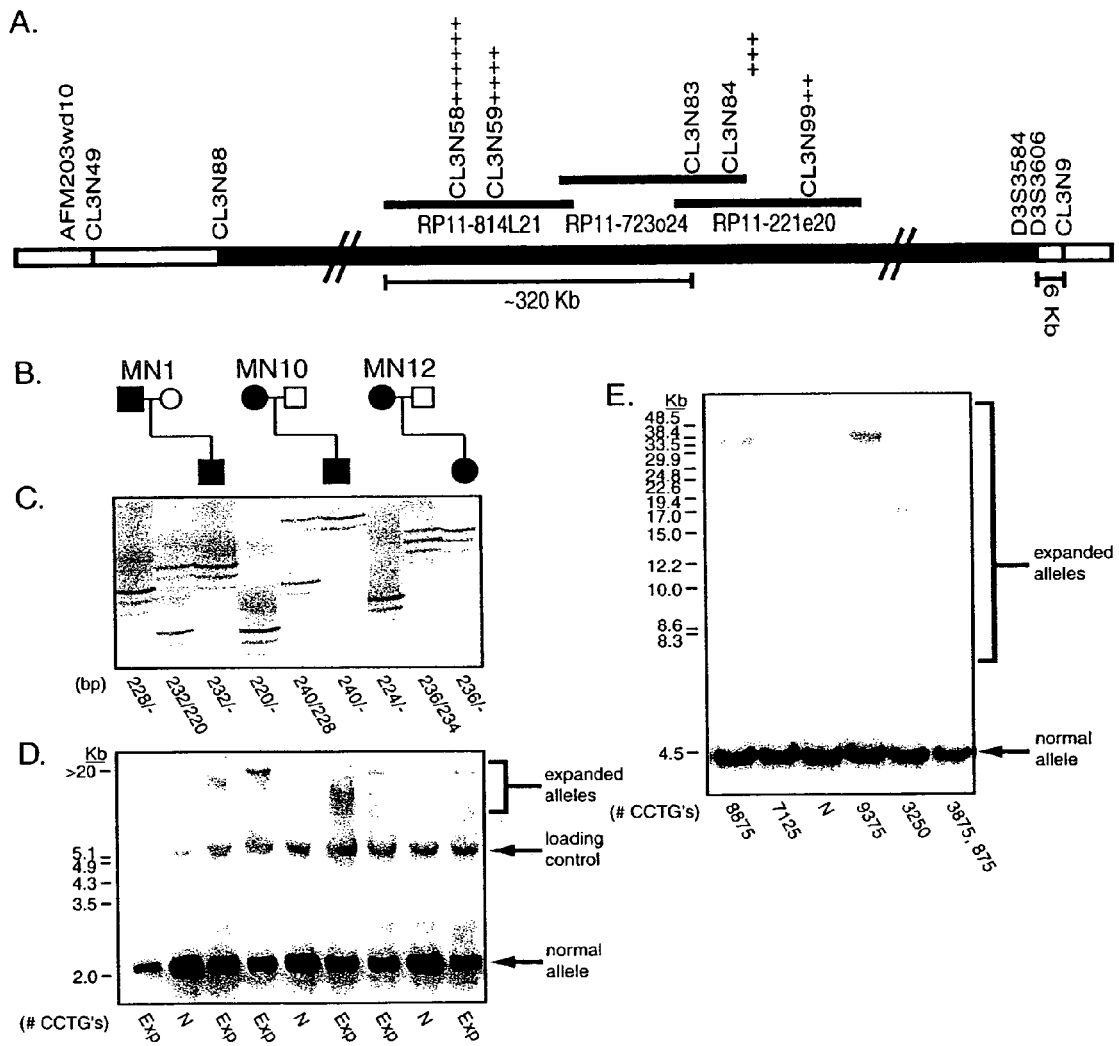
FIG. 1. Expanded CL3N58 allele found in DM2 patients. (A) DM2 critical region. Black represents the minimal DM2 critical region, white represents DM2 excluded regions, and grey represents regions in which recombination has occurred. Markers defining recombination events and establishing linkage disequilibrium are shown, along with previously published markers. The relative significance of the p-values are indicated by plusses above the marker names, with '++'≦0.01, '+++'≦0.001 '++++'≦0.0001, and '++++++'≦0.000001. Three BACs (orientation unknown) within the region of linkage disequilibrium are shown. Not drawn to scale. (B) Pedigrees of three different DM2-linked families, each represented by a nuclear family. (C) PCR analysis of CL3N58 marker. The genotype of each individual is shown, with the size of each allele given in basepairs below each lane. Unamplified alleles are represented by "–". (D) Southern-blot analysis of expansion mutations. Individuals with an expanded CCTG tract are represented by "EXP" and individuals with 2 normal alleles are represented by "N". The blot was also hybridized with an SCA8 loading control, showing that all but the first lane was evenly loaded. (E) High resolution sizing of expansions. Lane 3 contains DNA from a control sample. The number of CCTG's of each individual's expanded allele is shown, with "N" representing a normal length CCTG tract.

One of the markers in linkage disequilibrium with DM2, CL3N58 ($p \leq 0.000001$), showed an aberrant segregation pattern. All affected individuals appeared to be homozygous by PCR, and affected children appeared not to inherit an allele from their affected parent (FIG. 1, B and C). The PCR to amplify the DM2 repeat region from genomic DNA used primers CL3N58-D F (5'-GCCTAGGGGACAAAGTGAGA (SEQ ID NO:10)) and CL3N58-D R (5'-GGCCTTATAAC-CATGCAAATG (SEQ ID NO:11)) in a PCR reaction containing 200 µM dNTPs, 10 mM tris-HCl (pH 9.0), 50 mM KCl, 0.1% Triton X-100, 0.01% (w/v) gelatin, 1 mM $MgCl_2$, 0.4 µM each primer, and 0.1 U Taq. The reaction was cycled 30 times, where each cycle was 94° C. for 45 seconds, 57° C. for 45 seconds, and 72° C. for 1 minute.

Southern analysis was performed to investigate the possibility that the aberrant segregation pattern was caused by a repeat expansion or other rearrangement. BsoBI-digested genomic DNA (5 µg) was separated on an 0.8% agarose gel run for 4 hours at 110V, transferred to Hybond N+ membrane (Amersham, Piscataway, N.J.), and hybridized with a 485 base pair ZNF9 probe generated by PCR using the primers probeA F (5'-GAGAACCTTGCCATTTTCG (SEQ ID NO:22) and probeA R (5'-CACCTACAGCACTGGCAACA (SEQ ID NO:23)) and random-prime-labeled (GibcoBRL, Carlsbad, Calif.) with $^{32}$P-α-deoxyadensoine triphosphate (NEN, Boston, Mass.). To avoid partial digestions with BsoBI, we used 120 U of enzyme in a digestion volume of 120 µl. Membranes were prehybridized using RAPID-HYB buffer (Amersham, Piscataway, N.J.) at 60° for 1 hour. Hybridization was done using at least $4 \times 10^7$ counts per minute (cpm) total of the labeled probe, and incubation was overnight at 60°. The wash conditions were as follows: 2 washes for 5 minutes each at room temperature in a solution containing 2×SSC (one liter of 20×SSC contains 175.3 grams NaCl and 88.2 grams sodium citrate, pH 7.0) and 0.05% sodium dodecyl sulfate (SDS), followed by 2 to 3 washes for 30 minutes each at 52° in a solution containing 0.15×SSC and 0.1% SDS.

In addition to the expected normal allele, a variably sized expanded allele, too large to amplify by PCR, was detected by the Southern analysis and was found only in affected individuals (FIG. 1, B and D). Modified electrophoresis conditions enabled us to resolve a range of expansions between 10 and 48 kb (FIG. 1E). For more accurate sizing of the high molecular weight expansions, EcoRI-digested genomic DNA (5 µg) was separated on a 0.4% agarose gel run 24 hours at 35 V along with high molecular weight DNA markers (Gibco-BRL). BsoBI digests were more useful as a screening tool to identify individuals with DM2 expansions, as the bands were stronger and more discrete. EcoRI digests worked better for accurate sizing of large alleles, but the bands were often present as smears and were sometimes less distinct. The wash conditions were as follows: 2 washes for 5 minutes each at room temperature in a solution containing 2×SSC and 0.05% SDS, followed by 1 wash for 15 minutes at 50° in a solution containing 0.15×SSC and 0.1% SDS, followed by I wash for 10 minutes at 50° C. in a solution containing 0.15×SSC and 0.1% SDS.

To determine if this expansion was involved in the DM2 disease process, PCR and Southern analysis were performed on: (i) 51 affected individuals in six families whose disease was consistent with linkage to the DM2 locus; (ii) one affected individual from each of 20 additional families with ancestrally conserved DM2 haplotypes; and (iii) a panel of control genomic samples representing 1360 chromosomes. By PCR all 51 affected individuals in the six DM2 families appeared to be homozygous, with only one band detectable by PCR, but had and expanded allele on subsequent Southern analysis. The maximum lod scores at Θ=0.00 between the disease locus and the CL3N58 expansion for the six families were: MN1=6.9, MN6=1.5, MN10=8.2, MN12=2.8, F134=10.4, and F047=1.8. The maximum LOD scores for these families provide strong evidence that the disease and the expansion mutation are linked, and thus that the expansion mutation is responsible for DM2. Expanded alleles detected by Southern analysis were also found in affected representatives of all 20 additional families with ancestrally conserved DM2 haplotypes. PCR and Southern analysis identified no control samples with an expansion. Unrelated control DNA samples included the grandparents from the panel of 40 Centre d'Etude du Polymorphisme Humain (CEPH) families, spouses of patients diagnosed with muscular dystrophy or ataxia, and ataxia patients (n=1360 chromosomes).

Analysis of DM2-affected and Normal Alleles

Figure 2:
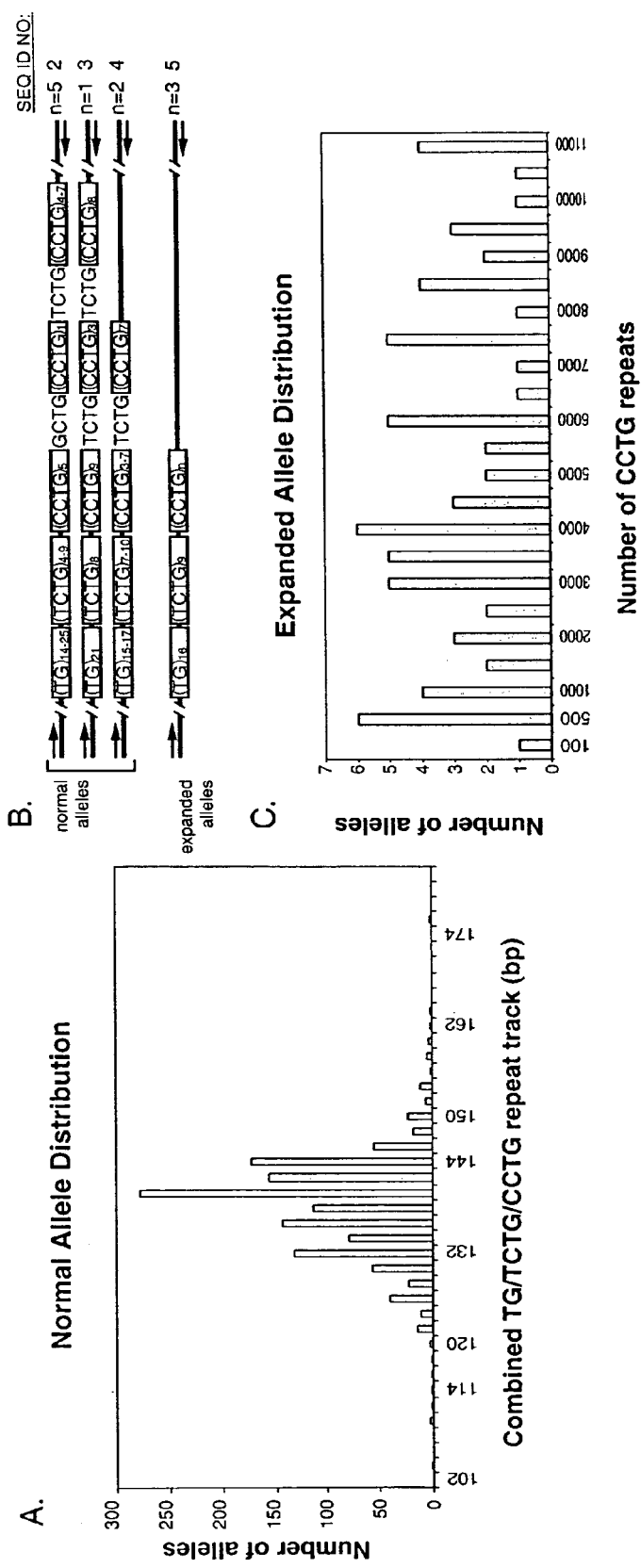
FIG. 2. Analysis of DM2 affected and normal alleles. (A) Distribution of CL3N58 alleles among controls (n=1360). Alleles represent the total basepair size of the combined TG, TCTG, and CCTG repeat tracts. (B) Schematic diagram of DM2 expansion region, showing sequence configurations of normal and expanded repeat tracts. (C) Distribution of expanded alleles among 51 affected members of six DM2 families. All expanded allele sizes were included for individuals with multiple bands and, in contrast to (B), are given in CCTG repeat units.

Sequence of the CL3N58 marker contained the complex repeat motif $(TG)_n(TCTG)_n(CCTG)_n$ (SEQ ID NO:40). In our control group, the size of the $(TG)_n(TCTG)_n(CCTG)_n$ (SEQ ID NO:40) repeat tract ranged from 104-176bp (Heterozygousity=0.89) (FIG. 2A). Eight normal alleles were amplified from genomic DNA as described above, cloned with the TOPO cloning kit (Invitrogen, Carlsbad, Calif.) and sequenced. All of these normal alleles had CCTG repeat tracts that were interrupted by both GCTG and TCTG motifs or by one or two TCTG motifs (FIG. 2B). The repeat tract in the largest normal allele (combined TG/TCTG/CCTG (SEQ ID NO:40) repeats of 176 bp) was sequenced and shown to contain 26 CCTG repeats with two interruptions. Smaller expanded alleles were amplified from genomic DNA using primers CL3N58-B F (5'-TGAGCCGGAATCATACCAGT (SEQ ID NO:24)) and CL3N58-D R in a PCR reaction (200 µM dNTPs, 50 mM Tris-HCl (pH 9.1), 14 mM (NH4)SO4, 2 mM MgCl2, 0.4 µM each primer, 0.1% Tween-20, 10% dimethyl sulfoxide, 0.75 U ProofSprinter enzyme (Hybaid-AGS, Ashford, Middlesex, UK)) cycled 35 times (94° C. for 30 s, 51° C. for 30 s, 72° C. for 1 mm). These expansions were also cloned with the TOPO cloning kit and sequenced, demonstrating that the CCTG portion of the repeat tract is expanded. In contrast to alleles from the control samples, the CCTG repeat tracts on expanded alleles were uninterrupted. Expansion sizes for very large alleles were estimated by Southern analysis assuming that, consistent with the sequenced expansions, lengthening of the CCTG repeat tract accounts for the increase in molecular weight. The range of expanded allele sizes is extremely broad, from 75 to ~11,000 CCTG repeats with a mean of ~5000 (FIG. 2C). Shorter expansions were found in individuals with multiple allele sizes in blood.

Instability of the DM2 Expansion

Figure 3:
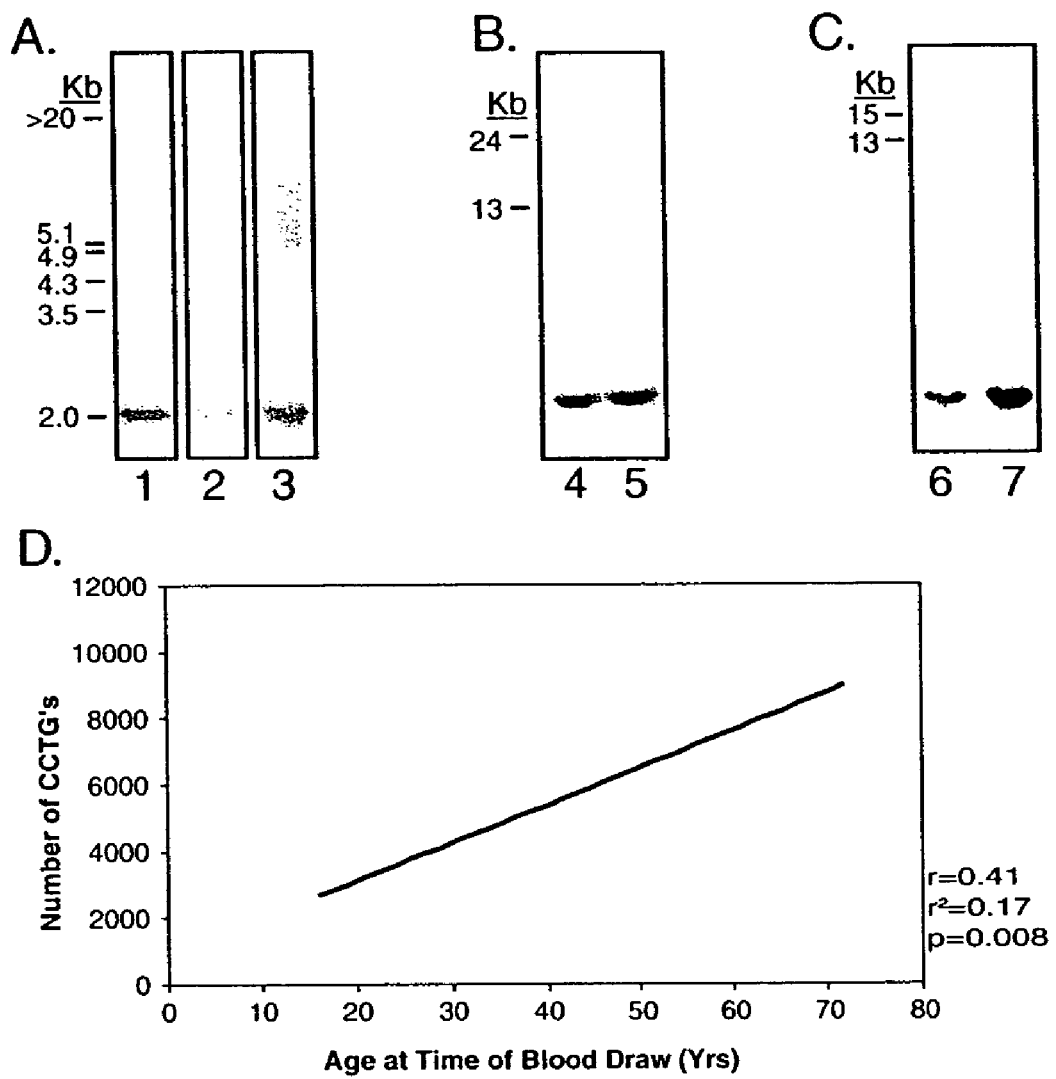
FIG. 3. Instability of the DM2 expansion. (A) Somatic heterogeneity in blood. Southern blots of BsoBI-digested genomic DNA from blood revealed multiple expanded alleles in some affected individuals, some discrete in size (lanes 1 & 2), others broad (lane 3). (B) Southern blots of EcoRI-digested genomic DNA from blood of monozygotic twins (lanes 4 and 5). (C) Expanded alleles increase in length over time. Southern blot of EcoRI-digested genomic DNA samples from blood taken from a single patient at 28 (lane 6) and 31 (lane 7) yrs of age, respectively. (D) Correlation between the size of the expanded allele in individuals with a single allele and age at the time blood sample was taken.

In approximately 25% of affected individuals two to four bands were observed in DNA isolated from blood, representing expanded alleles of various sizes (FIG. 3A, Table 1). Some bands were discrete in size, some appeared as unresolved compression bands at the top of the gel, and others showed a broad variation of molecular weight. An additional example of somatic instability included a pair of genetically confirmed (p≦0.001) monozygotic twins (31 y/o) that had dramatically different expanded alleles (13 kb and 24 kb) (FIG. 3B). Bayesian statistics were used on 6 STR markers from different chromosomes (D3S3684, SCA1 (CAG-a & CAG-b, Orr et al., Nature Genet., 4, 211-226 (1993)), SCA2 (SCA2-A & SCA2-B, Pulst et al., Nature Genet. 14, 269-276 (1996)), SCA3 (MJD52 & MJD25, Kawaguchi et al., Nature Genet. 8, 221-228 (1994)), SCA6 (S-5-F1 & S-5-R1, Zhuchenko et al., Nature Genet., 15, 62-69 (1997)), SCA8 (SCA8 F3 & SCA8 R2, Koob et al., Nature Genet., 21, 379-84 (1999))), sex, and disease status to confirm that the twins described in FIG. 3B were monozygotic (p>0.001). DNA from both parents and the twins were used to establish haplotypes. Further examples of somatic instability included the observation that the expansion size in lymphocyte DNA from an affected individual increased in size by approximately 2 kb during the 3-year interval between blood donations (FIG. 3C), and the age of affected individuals at the time they donated a blood sample directly correlated ($r=0.41$, $r^2=0.17$, $p=0.008$) with the size of the expansion (FIG. 3D). Expansion sizes in the blood of affected children are usually shorter than in their parents: the time-dependent somatic variation of repeat size complicates the interpretation of this difference (Table 1). No significant correlation between age of onset and expansion size was observed.

TABLE 1

Parent-offspring transmissions of the expanded allele in blood. Allele sizes are given in Kb. Multiple expansion sizes indicative of somatic instability are found in some individuals.

| Male Transmissions | | Female Transmissions | |
|---|---|---|---|
| Parental Alleles | Offspring Alleles | Parental Alleles | Offspring Alleles |
| 27, 20, 16 | 9 | 40 | 24 |
| 36 | 20 | 40 | 13 |
| 36 | 23 | 49 | 19 |
| 49 | 27 | 19 | 10, 6 |
| 29 | 27, 20, 6 | 40 | 11 |
| 48, 25 | 20, 5 | 40 | 16 |
| 17, 5 | 18, 9 | 42 | 20, 8 |
| 48, 25 | 38 | 20, 8 | 7 |
| 33, 12 | 49, 17, 12 | 38 | 33 |

Assembly of the ZNF9 Genomic Sequence

The DM2 expansion (CL3N58) was located in a region of the genome for which the available sequence was not completely ordered. To determine the location of the DM2 expansion, portions of the BAC RP11-814L21 were sequenced to assemble unfinished sequence contigs. Unordered sequence contigs from BAC RP11-814L21 (AC022944) were connected by sequencing from the ends of the known sequence contigs using the following primers: 77 3' (5'-CCTGACCT-TGTGATCCGACT (SEQ ID NO:25)), 66 3' (5'-TGCTTTAT-TATAGATTGGAATCCTCA (SEQ ID NO:26)), 66B 3' (5'-AAGACACCTGTCCCCCTAGAA (SEQ ID NO:27)), 39-5' (5'-GGGTGACAGAGCAAGACTCC (SEQ ID NO:28)), 52 3' (5'-TTTTAAACAATGCTACTTAGAATTTCA (SEQ ID NO:29)), 52 5' (5'-GCCGAATTCTTTGTTTTTGC (SEQ ID NO:30)), 59 5' (5'-TTGCTGCAGTTGATGGCTAC (SEQ ID NO:31)), 59B 3' (5'-TGAATTTACTAAGGCCCTTCCA (SEQ ID NO:32)), and 59C 3' (5'-GTGCTCACCTCTC-CAAGCTC (SEQ ID NO:33)). These connections were also verified by overlap with sequence from Celera (x2HTBKUAD8C) (Venter et al., Science 291, 1304-51 (2001)).

Our sequencing data and sequence from the Human Genome Project (McPherson et al., Nature 409, 934 (2001)) indicate that the expansion is located in intron 1 of the zinc finger protein 9 (ZNF9) gene (FIG. 4A), also referred to as the cellular nucleic acid-binding protein gene. GenBank accession numbers are as follows: genomic sequence of the DM2 region (AF389886, AF389887); CL3N58 sequence (AF388525); expanded CL3N58 sequence (AF388526); ZNF9 mRNA (M28372); original ZNF9 genomic sequence (U19765). The Celera accession number for the contig overlapping ZNF9 is x2HTBKUAD8C.

ZNF9 contains seven zinc finger domains and is thought to be an RNA-binding protein (Rajavashisth et al., *Science* 245, 640 (1989), Pellizzoni et al., *J. Mol. Biol.*, 267, 264 (1997)). Although the originally reported genomic sequence for ZNF9 (Pellizzoni et al., *J. Mol. Biol.*, 281, 593 (1998)) did not contain the CL3N58 marker, we have generated additional sequence, used sequence from Celera (Flink et al., *Gene* 163, 279 (1995)), and performed Southern and RT-PCR analysis to confirm the location of the expansion. To confirm the genomic organization of the ZNF9 gene, NsiI-digested genomic DNA (5 μg) was hybridized with an exon 5 probe generated by PCR using the primers ZNF9-E5 F (5'-GTAGC-CATCAACTGCAGCAA (SEQ ID NO:34)) and ZNF9-E5 R (5'-TAATACGACTCACTATAGGGAG-GACGGGCTTACTGGTCTGACTC (SEQ ID NO:35), T7 RNA polymerase promotor sequence is in italics).

Figure 5:
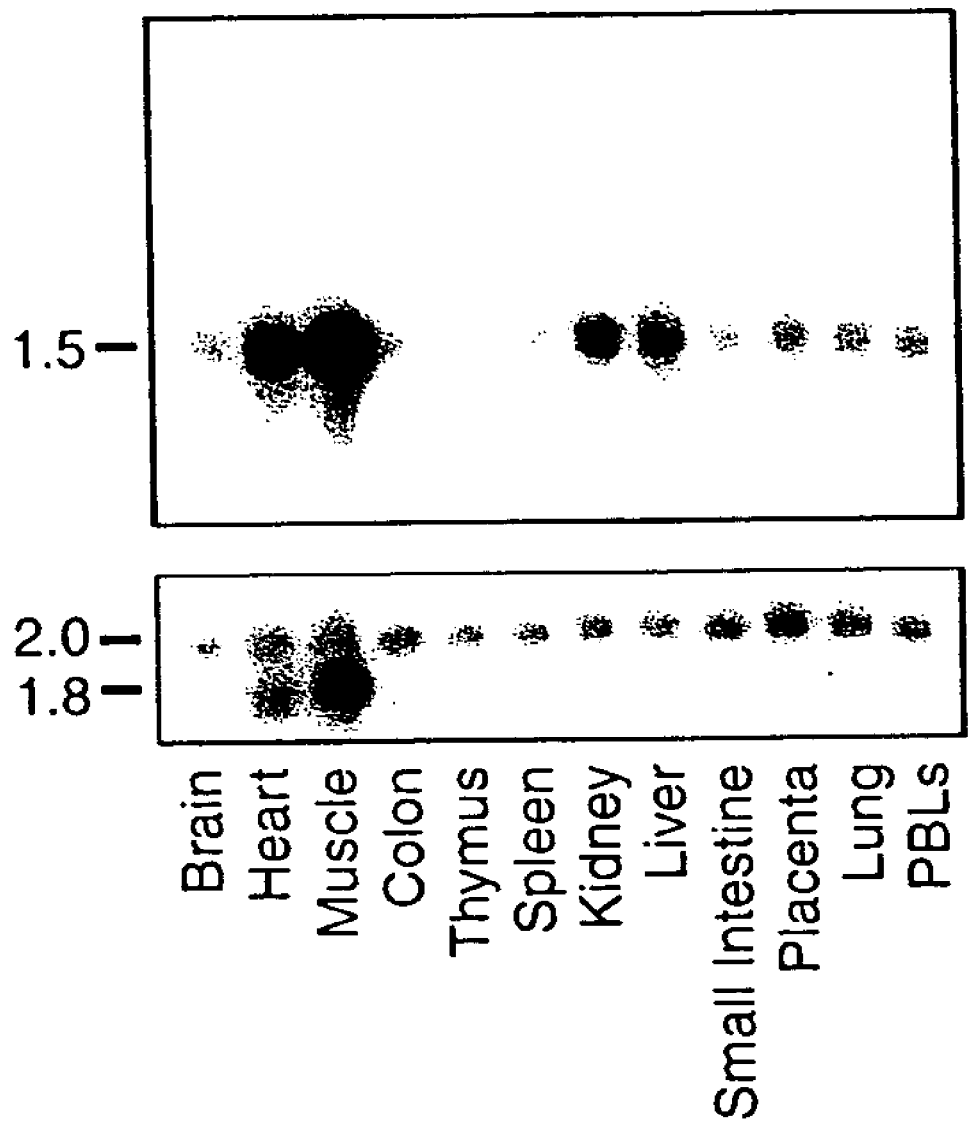
FIG. 5. Northern analysis of ZNF9 RNA expression. Upper panel, human multiple-tissue northern blot hybridized a riboprobe that included exon 5 of ZNF9; lower panel, actin used as a loading control; 1.5, 2.0, 1.8, size in kilobases.

The expression of ZNF9 RNA was evaluated in different tissues by Northern analysis. A human multiple-tissue Northern blot (Clontech, Palo Alto, Calif.) containing tissues from brain, heart, muscle, colon, thymus, spleen, kidney, liver, small intestine, placenta, lung, and peripheral blood lymphocytes (PBLs) was hybridized at 68° C. in UltraHyb hybridization buffer (Ambion, Austin, Tex.) with a 423 bp riboprobe that included exon 5 of ZNF9 (FIG. 5, upper panel). The PCR product was generated from genomic DNA with the primers ZNF9-E5 F and ZNF9-E5 R as described above and used for in vitro transcription using the Maxiscript kit (Ambion) and incorporating 32P-(alpha)-deoxycytosine triphosphate (ICN, Costa Mesa, Calif.) into the riboprobe. ZNF9 transcripts were found to be broadly expressed, and most abundant in heart and skeletal muscle, two tissues prominently affected in DM2.

In situ hybridization has been used to detect nuclear foci containing the CUG expansion in DM1 cells (Taneja et al., *J. Cell Biol.*, 128, 995 (1995)). Because DM2 is also caused by an expansion motif, we performed fluorescent in situ hybridization to determine if similar repeat-containing nuclear foci are found in DM2. Briefly, for in situ hybridization of muscle sections (Reddy et al., *Nature Genet.*, 13, 325 (1996)), we used 0.2 ng/μl 2'-O-methyl RNA oligonucleotides 5' labeled with Cy3 (IDT, Coralville, Iowa). The (CAGG)n, (CCUG)n, and (CAG)n oligonucleotides were all 20 bases in length. Fluorescence was visualized using a Zeiss Axioplan2 microscope equipped with a Spot CCD camera (Diagnostic Instruments, Sterling Heights, Mich.). Appropriate exposure times were computed using the DM2/CAGG slide, and the other probes were photographed using this exposure setting.

Fluorescently labeled antisense oligonucleotide probes to the CCUG repeat were hybridized to control, DM2, and DM1 muscle biopsy tissue. The DM2 muscle biopsy was from an affected member of the 3q-linked MN1 family (LOD=6.9), who had a CCTG expansion detected by Southern analysis. Similarly, DM1 tissue was taken from a genetically confirmed DM1 patient. Numerous intense CCUG-containing nuclear foci were observed in DM2 but not control muscle. In DM2 muscle, 1-5 foci were seen per nucleus, with no foci detected in the cytoplasm. In general, more foci were seen per nucleus in DM2 than were seen using antisense probes to the CUG expansions in DM1 muscle. The sense CCUG probes showed no nuclear foci, indicating that the probe hybridized to RNA not DNA. Our results show that the CCTG expansion is expressed but we do not yet know if the RNA foci contain the entire unprocessed ZNF9 transcript. The antisense CCUG probe showed no nuclear foci in DM1 muscle. Although the antisense probe to the CUG repeat also hybridized to foci in DM2 muscle, we believe this signal was caused by non-specific cross-hybridization to the extremely large CCUG repeat tract (11,000 repeats).

Discussion

These results demonstrate that DM2 is caused by an untranslated CCTG expansion. DM2 shows remarkable clinical similarity to DM1, although the disease course of DM2 is usually more benign. Clinical and molecular parallels between these diseases indicate that the CUG and CCUG expansions expressed at the RNA level can themselves be pathogenic and cause the multisystemic features common to DM1 and DM2. Given the similarity of the DM1 and DM2 repeat motifs and the fact that the expansions accumulate as RNA foci, RNA-binding proteins that bind to the DM1 CUG expansion may also bind to the DM2 CCUG expansion causing similar global disruptions in RNA splicing and cellular metabolism (Timchenko et al., *Nucleic Acids Res.*, 24, 4407 (1996), Lu et al., *Hum. Mol. Genet.*, 8, 53 (1999), Miller et al., *EMBO J.*, 19, 4439 (2000)). One of these proteins has been shown to have a preferential affinity for UG dinucleotides (Takahashi et al., *Biochem. Biophys. Res. Commun.*, 277, 518 (2000)), which are found in both DM1 and DM2 expansions. If these same RNA-binding proteins are involved in DM2 pathogenesis, then one could speculate the longer CCUG repeat tracts cause the milder DM2 phenotype because the affinity of these proteins for the CCUG repeat tract is not as strong. Alternatively, a different set of RNA-binding proteins may bind to the CCUG expansion.

DM2 is the fourth example of a dominant disease that is caused by a microsatellite expansion located in a transcribed but untranslated portion of its respective genes. On the molecular level, the CCTG DM2 expansion has parallels to the untranslated CTG expansions involved in both DM1 (Groenen et al., *Bioessays* 20, 901 (1998), Tapscott, *Science* 289, 1701 (2000)) and SCA8 (Koob et al., *Nature Genet.*, 21, 379 (1999)) as well as the ATTCT expansion in SCA10 (Matsuura et al., *Nature Genet.*, 26, 191 (2000)). The DM2 tetranucleotide and the SCA10 pentanucleotide expansions are generally longer than the expansions associated with the triplet repeat diseases, with the largest DM2 and SCA10 repeats estimated to be ≧11,000 and 4,500 repeats, respectively.

Repeat instability in DM2 is complicated by the compound repeat motif $(TG)_n(TCTG)_n(CCTG)_n$ (SEQ ID NO:40) and time-dependent somatic instability of the expansion. Although similar somatic instability is seen in DM1 and FMR1 (Wong et al., *Am. J. Hum. Genet.* 56, 114 (1995), Moutou et al., *Hum. Mol. Genet.* 6, 971 (1997), Helderman-van den Enden et al., *J. Med. Genet.* 36, 253 (1999), Lopez de Munain et al., *Ann. Neurol.* 35, 374 (1994)), the size differences for DM2 can be much larger, up to 9000 repeats in the blood of one affected individual. Clinical anticipation has been reported in DM2/PROMM families (Schneider et al., *Neurol.*, 55, 383 (2000)).

Example 2

Repeat Assay

In most cases the expanded alleles are too large to amplify by PCR (FIG. 5A, and Example 1 above). All affected individuals appear to be homozygous by PCR (FIG. 5A, lanes 2 and 3), and affected children often do not appear to inherit an allele from their affected parent. Because some normals can be true homozygotes that can not be distinguished from the DM2 hemizygotes, in some cases CL3N58 PCR is not a definitive test for the DM2 expansion. Southern-blot analysis can used to detect the presence of the expanded allele in affected individuals, as well as confirm the lack of any expansion in any unaffected homozygotes. However, in some cases it can be difficult to visualize the expansion with Southern-blot analysis. Note that there is not the 1:1 correlation in intensity between normal and expanded alleles (FIG. 5B, lanes 1-4), as is seen in other expansion diseases such as SCA8 (FIG. 5B, lane 8). Sometimes the expanded allele(s) can appear so much fainter than the normal allele as to be indistinguishable from background (FIG. 5B, lanes 6 and 7).

To detect the presence of DM2 expansions from individuals for whom Southern blot analysis either appears to be negative or is inconclusive, an additional assay, referred to as the Repeat assay or repeat assay (RA), was developed by modifying a version of PCR developed by Warner et al. (*J. Med. Genet.*, 33, 1022-1-26 (1996)) and Matsuura and Ashizawa (*Ann. Neurol.*, 51, 271-272 (2002)) for the detection of DM1 and SCA10 repeat expansions. This assay can reliably identify the presence or absence of DM2 expansions, although the size of any detected expansion cannot be determined.

The DM2 repeat region (TG/TCTG/CCTG) (SEQ ID NO:40) was amplified from genomic DNA using the primers CL3N58-D R (5'-GGCCTTATAACCATGCAAATG (SEQ ID NO:11), JJP4CAGG (5'-TACGCATC-CGAGTTTGAGACGCAGGCAGGCAGGCAGGCAGG (SEQ ID NO:36)), and JJP3(5'-TACGCATC-CGAGTTTGAGACG (SEQ ID NO:37)). CL3N58-D R binds to a unique sequence upstream of the TG/TCTG/CCTG (SEQ ID NO:40) repeat tract. JJP4CAGG consists of the repeat sequence with 5' hanging tail sequence that has negligible complementarity to any known human sequence. The repeat portion of JJP4CAGG will bind randomly at multiple sites within an expanded CCTG tract, giving rise to PCR products of varying sizes, visualized as a smear. JJP3 was complementary to the hanging tail sequence in JJP4CAGG when incorporated into a PCR product, and was used to increase the robustness of the PCR reaction. Optimal amplification was found using PCR reactions of 25 ul volumes with the following buffer components: (200 µM dNTPs, 50 mM Tris pH 9.1, 14 mM $(NH_4)SO_4$, 2 mM $MgCl_2$, 0.4 µM each primer, 0.1% Tween-20, 10% DMSO, 0.75 U ProofSprinter enzyme (Hybaid-AGS)). The PCR conditions consisted of an initial denaturing at 95° C. for 15 minutes, 35 PCR cycles (94° C. for 30 seconds, 51° C. for 30 seconds, 72° C. for 2 minutes), and an additional extension at 72° C. for 10 minutes. Five microliters of 6× loading dye was added to the PCR product and 25 ul were loaded onto an 1% agarose gel with 1 ul of ethidium bromide solution (10 ug/ul) per 100 mls and run for 45 mm to 1 hr at 150 V. The gels were transferred to Hybond N+ membrane (Amersham, Piscataway, N.J.) and hybridized with an internal primer CL3N58E-R (5'-TTG-GACTTGGAATGAGTGAATG (SEQ ID NO:38)) probe end-labeled with $^{33}$P-g-dATP using Rapid-Hyb buffer (Amersham, Piscataway, N.J.) according to the manufacturer's instructions. After hybridization the membrane was washed at 45° C. in 2×SSC and 0.1% SDS and exposed to X-ray film.

Example 3

DM2 in 133 Families: Clinical Features Common to DM1 Demonstrate Pathogenic Effects of CUG/CCUG RNA Expansions are Multisystemic Methods Family Identification and Clinical Studies Subjects with the clinical diagnosis of DM2 or PROMM, and without a DM1 expansion were enrolled in the research, as were all available family members at risk for the disorder, and spouses with an affected or at risk child. Findings are reported for subjects with CCTG DM2 expansions.

Studies were performed over a 10-year period of time, with additional testing included as understanding of the disease evolved. Subjects were interviewed and examined in both clinical and community settings. Electrophysiological assessment was done with portable electromyographic equipment, including Nicollet and Dantec/Medtronik electromyographic equipment. Ophthalmologic examinations in the field were performed with direct ophthalmoscopy; some individuals additionally underwent slit lamp examinations in ophthalmology clinics. Muscle biopsies were quick-frozen, sectioned and stained with hematoxylin and eosin for most results reported, identifying fiber types by ATPase staining at different pH values. Clinical results are reported as percentages of individuals tested for each specific feature.

Genetic Methods

CL3N58 PCR amplification across the DM2 CCTG repeat, and Southern analysis, was done as described Example 1. The Repeat assay was performed as described in Example 2.

Results

Patient Population

We have studied 352 subjects genetically diagnosed as having DM2 from 133 German and Minnesota families. Most families could trace an affected ancestor to Germany or Poland and all were of European descent. 332 males and 420 females at risk for the disease participated in the study, of those 147 males and 208 females were positive for the DM2 expansion. The age of the participants ranged from 8 to 85 with a mean age of 47 years.

Clinical Features of DM2 Patients

Muscle Symptoms and Signs. Similar to DM1, myotonia and muscle weakness are the most common symptoms reported in DM2 subjects of all ages (Table 2). Similarly, the characteristic pattern of muscle weakness in DM1 affecting neck flexion, thumb or finger flexion, and elbow extension is also present in DM2[(Harper et al., *Neurology*, 56, 336-340 (2001))]. Facial and ankle dorsiflexor weakness, features of DM1, were present to a lesser degree in DM2 subjects. Subjects with DM2 or PROMM frequently developed symptomatic weakness after age 50 years, when they began to complain of difficulty standing up from a squatting position. Although hip-flexion weakness is the reason most DM2/PROMM subjects seek medical attention, in DM1 it often develops after patient have sought medical assistance for other problems. Muscle pain, which is common in DM2, is also common, although less recognized in DM1. Among DM2 patients between 21-34 years of age, only 36% complained of weakness, but on examination weakness was demonstrable in 59%.

TABLE 2

CLINICAL FEATURES OF DM2 AND DM1

| | | DM2 Subjects by Age | | | |
|---|---|---|---|---|---|
| | | 21–34 y (n = 45) | 35–50 y (n = 77) | >50 y (n = 100) | DM1 |
| Skeletal Muscle Features | | | | | |
| History of Muscle Pain | | 43% | 61% | 63% | +/++ |
| Myotonia | By History | 39 | 39 | 34 | +++ |
| | On Physical Exam | 80 | 84 | 71 | +++ |
| | On EMG (210) | 87 | 94 | 92 | +++ |
| Weakness | By History | 36 | 69 | 84 | +++ |
| | Any Weakness on Exam | 59 | 85 | 99 | |
| | Facial | 18 | 9 | 13 | ++ |
| | Neck Flexion | 47 | 75 | 95 | +++ |
| | Elbow Extension | 8 | 16 | 52 | ++ |
| | Thumb/Finger Flex | 39 | 63 | 49 | +++ |
| | Hip Flexion | 36 | 58 | 88 | + |
| | Ankle Dorsiflexion | 9 | 14 | 19 | ++ |
| | Deep Knee Bend | 26 | 48 | 77 | + |
| High CK | | 88 | 91 | 93 | ++ |
| Multisystemic Features | | | | | |
| Cardiac | Arrhythmia/Palp | 7% | 27% | 27% | + |
| | Cardiomyopathy | 0 | 0 | 7 | +/− |
| Cataracts | By history or exam | 36 | 59 | 78 | ++ |
| | Hx Extraction | 13 | 18 | 55 | |
| Diabetes | By history | 4 | 17 | 36 | + |

| Additional Laboratory Findings | | | | |
|---|---|---|---|---|
| | | DM2 | | |
| | | Mean Age (Age Range) | % Affected | DM1 |
| Serology | High GGT (152) | 46 y (13–78 y) | 64% | + |
| | Low IgG (20) | 46 (28–64) | 65 | ++ |
| | Low IgM (20) | 46 (28–64) | 11 | + |
| | Low Testosterone (22) | 45 (27–64) | 29 | ++ |
| | High FSH (26) | 42 (16–64) | 65 | ++ |
| | Insulin Insensitivity (16) | 47 (28–75) | 75 | ++ |
| EKG | AV Block (44) | 47 (16–73) | 11 | ++ |
| | IV Block (44) | 47 (16–73) | 11 | + |
| Muscle Biopsy | Internal nuclei (42) | 50 (16–64) | 95 | ++ |
| | Nuclear Bag fibers (36) | 50 (16–64) | 89 | ++ |
| | Abnl fiber typing (31) | 50 (16–64) | 16 | +/− |
| | Necrotic fibers (38) | 50 (16–64) | 47 | + |
| | Fibrosis (38) | 50 (16–64) | 71 | + |

DM1 features are reported as being almost universally present (+++), common and almost universally present late in the course of the disease (++), well recognized and common late in the course of the disease (+), and recognized but not common (+/−).

Muscle Biopsies. Muscle biopsies from 42 DM2 patients were indistinguishable from DM1 biopsies on routine studies, with a high percentage of fibers having centrally located nuclei that sometimes occur in chains, angulated atrophic fibers sometimes occurring in groups, severely atrophic ("nuclear bag") fibers, hypertrophic fibers, occasional necrotic fibers, fibrosis and adipose deposition. There was no consistent abnormality of fiber type distribution, with 2 biopsies having mild type 1 predominance and 2 having mild type 2 predominance. Atrophic angulated fibers of both fiber types, as determined by ATPase staining, were evident in most biopsies. Cataracts. The posterior subcapsular iridescent cataracts are identical in DM1 and DM2 patients. Cataracts needed to be extracted in 75 individuals at ages ranging from 28-74 years. Among 10 genetically positive subjects under 21 years, cataracts were present in two, indicating that this is a prominent and early feature of the disease. In DM1, cataracts evident by ophthalmoscopy typically develop in the $3^{rd}$-$5^{th}$ decades of life, with small percentages occurring in the $2^{nd}$ decade of life.

Cardiac Features. In DM2 patients, cardiac complaints include frequent palpitations, intermittent tachycardia and episodic syncope. These symptoms, which are present in both DM1 and DM2, increase in frequency with age (Table 2). Cardiac conduction abnormalities, either atrioventricular or intraventricular blocks, were seen in 20% (9/44) of DM2 patients. Conduction abnormalities are more frequent in DM1, but patients with either disease can develop unexpected fatal arrhythmias. Cardiomyopathy, a debilitating and life-threatening condition found in 7% of DM2 patients over 50 years, is rarely reported in DM1.

Systemic Changes. A striking feature of myotonic dystrophy is the idiosyncratic involvement of nearly all organ systems. Many of the features that include the broad clinical presentation of DM1 are mirrored in DM2. Laboratory results from 150 patients showed elevated serum CK (typically less than 5× the upper limits of normal) and GGT. Additional serological testing on 20 patients showed low IgG and IgM, but normal IgA. As in DM1, evidence of primary male hypogonadism was present in the majority of males, with elevated FSH, low or low-normal testosterone levels, and several men having documented oligospermia. Blood glucose levels showed diabetes in 23% (n=79). Formal glucose tolerance testing showed insulin insensitivity (elevated basal insulin levels or prolonged insulin elevation, n=16). Age-independent hyperhydrosis reported by 20-30% of DM2 patients is also present in DM1, and early-onset male frontal balding is common in both disorders.

Age of onset. Initial DM2 symptoms were reported to have occurred from ages 8-67, with a mean age of onset of 48 y. Individuals less than 21 years of age were not routinely enrolled in the study, but analysis of reports from 12 such genetically affected individuals showed reports of muscle pain, myotonia, and hyperhydrosis, but not weakness, cardiac symptoms, diabetes or visual impairment from cataracts. A severe congenital form of DM2 has not been observed.

Genetic and Molecular Features

Figure 6:
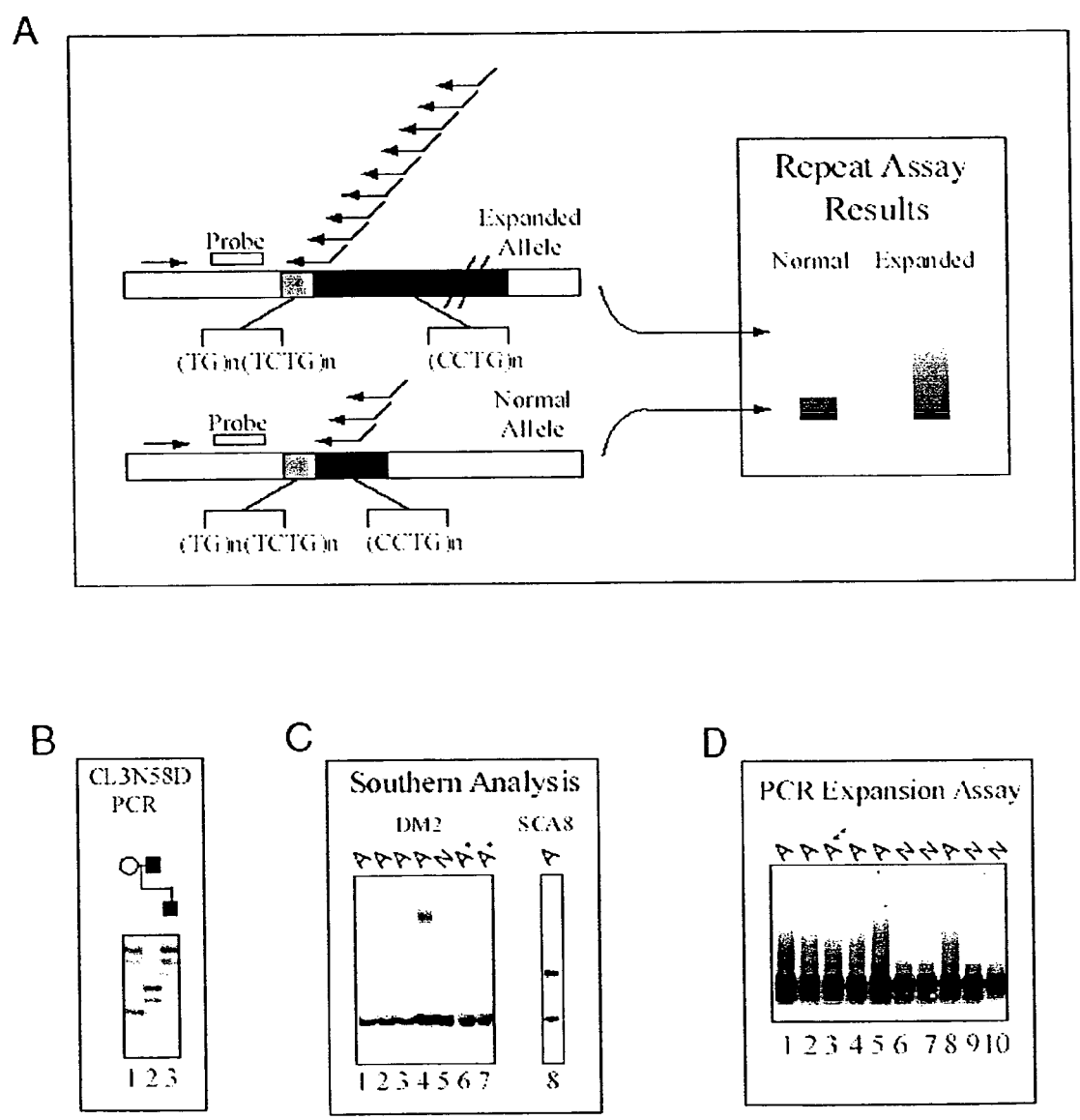
FIG. 6. (A) Schematic diagram of repeat assay PCR reaction products. (B) PCR analysis of CL3N58 marker. Lane 1, from the unaffected mother, shows two alleles. Lanes 2 and 3, from the affected father and affected son, respectively, show only one allele. There is no shared allele in lanes 2 and 3, as would be expected in normal Mendelian inheritance of PCR alleles. (C) Southern-blot analysis of expansion mutations. Lanes 1-4 show affected individuals with detectable expanded bands. Lane 5 shows an unaffected individual with only the normal-sized band. Lanes 6 and 7 show affected individuals with no detec" expansion. Lane 8 shows an affected SCA8 individual with an expanded band. (D) Repeat assay of DM2 mutations. Lanes 1-5 and 8 show affected individuals who are expansion-positive, indicated by smears above the normal allele, by the Repeat assay. Lanes 1, 2, 4, 5, and 8 show affected individuals who had expansions by Southern-blot analysis, while lane 3 shows an affected individual who had no detectable expansion by Southern-blot analysis. Lanes 6, 7, 9, and 10 show unaffected individuals who are expansion-negative, indicated by the lack of smears above the normal allele, by the Repeat assay. (E) Abbreviated pedigree of a DM2 family. Filled-in symbols represent affected individuals. Below each symbol: age of blood draw, CL3N58 PCR allele sizes (where "B" signifies evident existence of a non-amplifying blank allele), and either the size of the expansion detected by Southern ("N kb") or the result of the Repeat assay, given as Exp(+) or Exp(−), where Exp refers to expansion, for those with no expansion on southern analysis.
Figure 6:
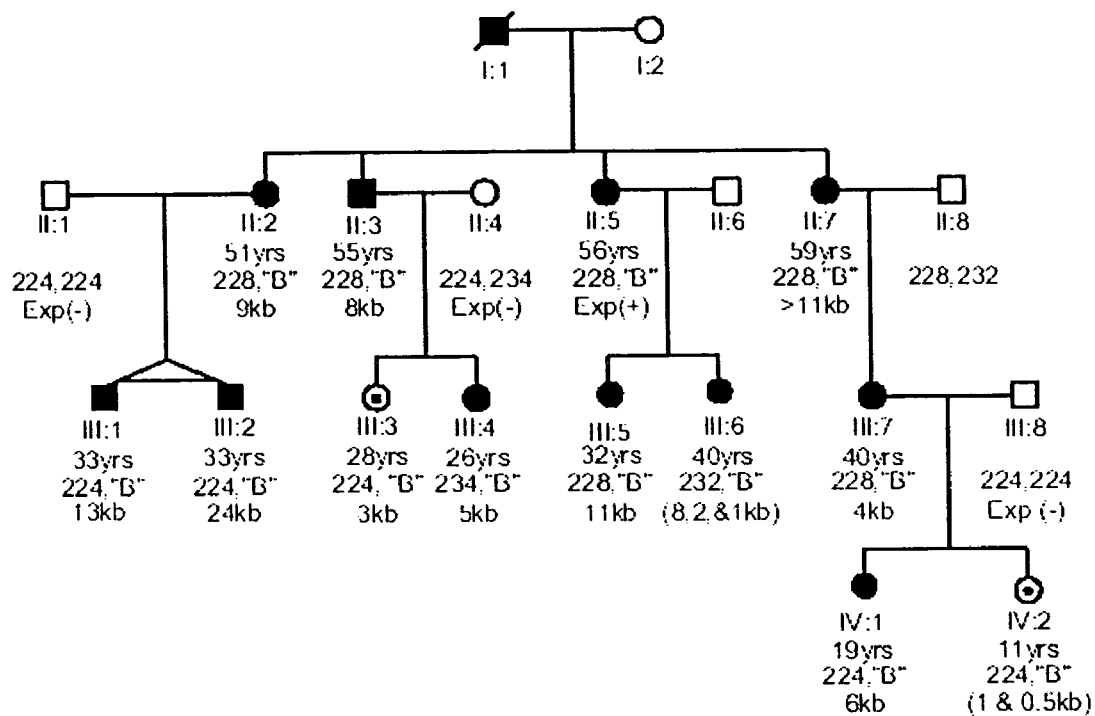

Diagnostic Methods and Instability. The unprecedented size and somatic instability of the DM2 expansion complicate molecular testing and interpretation of genetic test results (FIG. 6). The DM2 locus contains a complex repeat motif (TG)n(TCTG)n (CCTG)n (SEQ ID NO:40), with the CCTG portion expanding on affected alleles. The expanded alleles are too large to amplify by PCR, causing all affected individuals to appear homozygous (FIG. 6B, lanes 2 and 3) and thus indistinguishable from the 15% of unaffected controls who are truly homozygous. Family studies can distinguish true homozygotes from expansion carriers, (FIG. 6B lanes 1-3), because affected children often do not appear to inherit an allele from their affected parent. We refer to this apparent non-Mendelian inheritance pattern, which is caused by the failure of the expanded allele to amplify, as the presence of a "blank allele." Demonstration of a blank allele provides strong evidence that a family carries a DM2 expansion, but can also occur due to non-paternity.

In other expansion disorders, Southern analysis (FIG. 6C) can reliably confirm the presence of expansions too large to amplify by PCR. Because of the unprecedented size (>11,000 CCTG repeats) and somatic instability of the DM2 repeat, genomic Southerns fail to detect 26% of expansions in known carriers. Expanded alleles when detected can appear as single discrete bands, multiple bands, or smears (FIG. 6B). Compared to other expansion disorders, such as SCA8 (FIG. 6D, lane 8), in which the expanded and normal alleles are equally intense, detectable DM2 expansions are almost always less intense than the normal alleles. This intensity difference indicates that even when a proportion of the expanded alleles create a discrete visible band, the rest of the expanded alleles vary markedly in size resulting in a diffuse undetectable smear.

To detect the presence of DM2 expansions in individuals with inconclusive Southern blots, the repeat assay (RA) described in Example 2 was used. By using a PCR primer that hybridizes and primes from multiple sites within the elongated CCTG repeat tract, this assay reliably identified the presence or absence of DM2 expansions. To insure specificity, the PCR products were transferred to a nylon membrane and probed with an internal oligonucleotide probe. When the probe was used there were no false positives in 320 control chromosomes. In contrast there was a 5% false positive rate when the PCR products were visualized directly without use of an internal probe. As detailed in Table 3, the DM2 repeat assay is a sensitive and specific method to identify DM2 expansions, increasing the detection rate from 74% by genomic Southern analysis alone to 99% using both methods. Among all of the samples tested, 352 individuals have been identified from 133 families who were genetically confirmed by Southern and/or RA analyses.

TABLE 3

| Confirmed DM2 Cases* | Expansion Detected by Southern | Expansion Detected by Repeat Assay | Expansion Detected by either Southern or Repeat Assay |
|---|---|---|---|
| 174 | 128 74% | 166 95% | 172 99% |

*Individuals independently confirmed to have DM2 expansions by presence of "blank allele" or linkage analysis The correlation of the repeat size with various measures of disease onset for individuals with single bands on Southern analysis is shown in FIG. 8. For repeat size versus age at onset of initial symptom (n=91) there was a positive correlation r=0.28 (p=4.2×10$^{-3}$, r$^2$=0.08). For repeat size versus age at onset of weakness (n=59) a positive correlation coefficient of r=0.53 was obtained (p=8.7×10$^{-6}$, r$^2$=0.28). No significant correlation was observed between repeat size and age of cataract extraction (n=29). The positive correlations between repeat length and age of onset, as well as repeat length and onset of weakness, were surprising because in all other microsatellite expansion disorders larger expansions are associated with earlier ages of onset. To determine if these positive correlations could be explained by the increase in CCTG repeat tracts with age, multivariate analysis was performed and indicated that the effect of age on repeat length explained more than 98% of the apparent of effect of repeat length on onset of symptoms.

Figure 9:
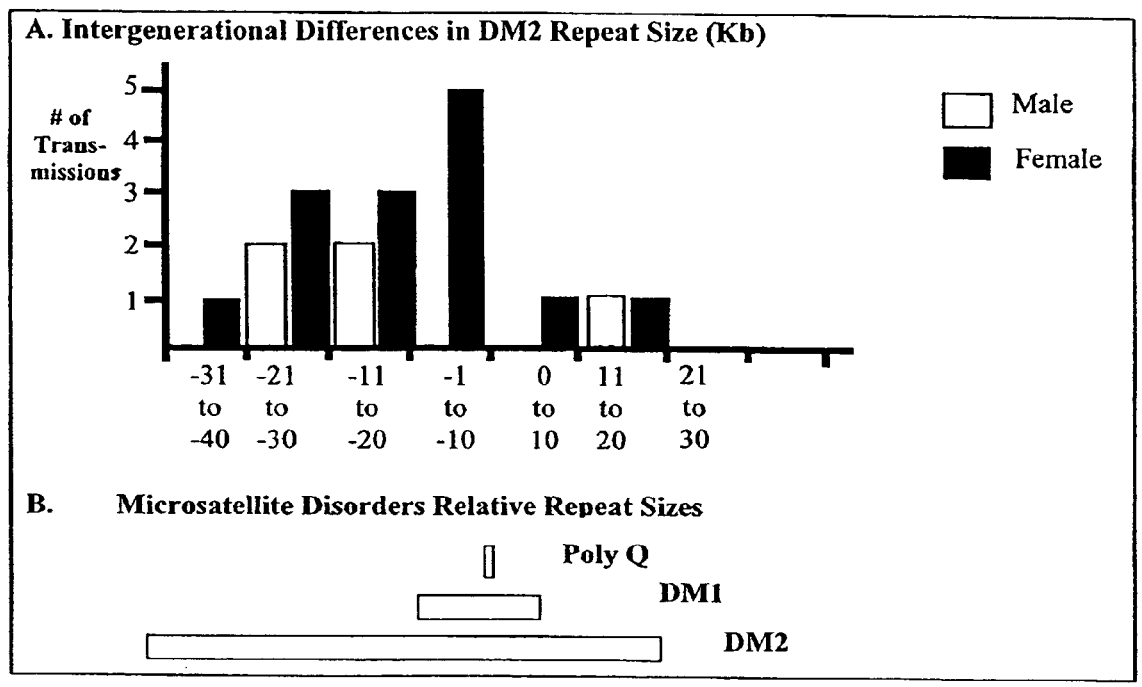
FIG. 9. Intergenerational changes in repeat length.

Although complicated by somatic instability and increases in repeat length with age, we compared repeat lengths of 19 affected parent-child pairs from a subset of individuals in which both the parent and child had single bands on Southern analysis (FIG. 9A). Surprisingly, we observed apparent reductions of repeat length in 16 of 19 transmissions, with a mean change of −13 Kb (−3250 CCTG repeats). In one instance the repeat size was 38 Kb smaller in the affected child (−9500 CCTG repeats). There were apparent size increases in 2 transmissions (+8 and +13 Kb). No differences in degree or direction of intergenerational changes were seen in male vs. female transmissions. These apparent intergenerational changes in repeat length are much greater for DM2 than for any other microsatellite disorder (FIG. 9B).

Pedigree Examples of Instability

The pedigree shown in FIG. 6E illustrates the diagnostic challenges and types of repeat instability that are typical in a DM2 family. Intergenerational repeat sizes can vary dramatically. For example individual III-7 has a smaller expansion than her affected parent, which is larger in one of her children and smaller in the other. Somatic instability is strikingly illustrated by monozygotic twins III-1 and III-2, with expansion sizes that differ in size by 11 kb (2750 CCTGs). Some family members have single discrete expansions, multiple expansions and diffuse bands. An example of the utility of the repeat assay is demonstrated by individual II-5, who was RA positive but negative by Southern analysis.

Discussion

Clinical Features

This study details the broad idiosyncratic features common to DM1 and DM2, demonstrating the multisystemic effects of CUG and CCUG RNA expansions in disease pathogenesis. DM2 closely resembles adult-onset DM1, with a long list of common features including progressive weakness, myotonia, disease specific muscle histology, cardiac arrhythmias, iridescent cataracts, male hypogonadism, early-onset balding, insulin insensitivity, and hypogammaglobulinemia. The presence of these seemingly unrelated features in both DM1 and DM2 indicates that a common pathogenic mechanism is likely responsible for both disorders.

Despite the striking similarities of DM2 and adult-onset DM1, there are differences. One clear distinction is the lack of a congenital form of DM2. Other differences of DM2 include an apparent lack of mental retardation, and less evident central hypersomnia, severe distal weakness, and marked muscle atrophy. DM1 individuals often come to medical attention because of the mental retardation or disabling distal weakness and myotonia, but DM2 patients typically first seek medical evaluation when they develop proximal lower extremity weakness. Although many DM2 features are milder than in DM1 (clinical myotonia, distal and facial weakness), some appear to be equally significant (cataracts, hypogonadism, and insulin insensitivity), and others may be more severe in DM2 (cardiomyopathy). It remains to be determined whether the generally milder phenotype of DM2, despite the presence of a much larger genetic repeat expansion, indicates that the pathophysiological effects of CCTG expansions are simply less severe than CTG expansions, or whether secondary processes augment the pathophysiological mechanisms in DM1.

We have identified 389 DM2-positive individuals from 133 families. Our ability to identify a large number of DM2 families in both Minnesota and Germany indicates that initial estimates that 98% of DM families have the DM1 expansion are too high, at least in Northern European populations. DM1 families often come to medical attention when a child is severely affected. In contrast the lack of congenital DM2 may explain its apparent underdiagnosis. DM2 patients often seek medical attention for isolated disease features, without being aware of their complex underlying disease. A genetic diagnosis of DM2 will improve patient care by facilitating better monitoring of the diverse clinical features known to be part of the disease, including early onset cataracts, diabetes, testicular failure and cardiac arrhythmias.

Genetics

Unique genetic features of the DM2 expansion include the following: i) it is the first pathogenic tetranucleotide expansion; ii) expansions are larger than reported in any other disease (more than 44 Kb in DM2 versus 12 Kb in DM1); iii) there is an unprecedented degree of somatic instability. The somatic instability is so dramatic that ~¼ of the expansions are not detectable by Southern analysis, which results in a diagnostic challenge not previously reported, even among disorders with large expansions such as DM1, SCA8, and SCA10. Although the somatic instability complicates the molecular diagnosis of DM2, combining it with the RA improves detection to >99%.

In other reported microsatellite expansion disorders larger repeat tracts are associated with earlier onset and increased disease severity. Although anticipation has been reported in DM2/PROMM families based on clinical criteria, the expected trend of longer repeats being associated with earlier ages of onset was not observed. The somatic heterogeneity, and the fact that the size of the repeat dramatically increases in size with age, complicate this analysis and may mask meaningful biological effects of repeat size on disease onset. It is also possible that expansions over the pathogenic size threshold exert similar effects regardless of how large they become, or even that smaller repeats are more pathogenic than larger repeats. In adult-onset DM1, the tightest correlations between repeat length and disease onset are for repeats less than 150 CTGs, which may indicate that correlations at larger repeat sizes for DM1 are also difficult to measure either because of increased somatic mosaicism or a ceiling effect in which repeat sizes over a certain length cause similar degrees of pathology. Determination of DM2 somatic mosaicism in tissues other than blood may help clarify the pathogenic effects of the expansion, although somatic mosaicism observed in other tissues (such as skeletal muscle) may continue to obscure length-dependent pathological effects. The intergenerational differences in repeat length in DM2, with surprisingly shorter repeat tracts seen after both maternal and paternal transmission, may also be affected by the marked range of repeat size in each affected individual and the increase in repeat length over time.

The complete disclosure of all patents, patent applications, and publications, and electronically available material (including, for instance, nucleotide sequence submissions in, e.g., GenBank, dbSTS, and RefSeq, and amino acid sequence submissions in, e.g., SwissProt, PIR, PRF, PDB, and translations from annotated coding regions in GenBank and RefSeq) cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

What is claimed is:

1. An isolated polynucleotide comprising about nucleotides 17501-17701 of SEQ ID NO:1 and an at risk repeat tract, and the full complements thereof.

2. An isolated polynucleotide comprising about nucleotides 17858-18062 of SEQ ID NO:1 and an at risk repeat tract, and the full complements thereof.

3. The isolated polynucleotide of claim 1 wherein the at risk repeat tract comprises $(TG)_x(TCTG)_y(CCTG)_z$, wherein x is an integer from 14 to 25, y is an integer from 3 to 10, and z is an integer from 75 to 11,000.

4. The isolated polynucleotide of claim 1 wherein the at risk repeat tract comprises from 75 to 11,000 CCTG repeats.

5. The isolated polynucleotide of claim 4 wherein the at risk repeat tract comprises at least 75 CCTG repeats uninterrupted by other nucleotides.

6. The isolated polynucleotide of claim 2 wherein the at risk repeat tract comprises $(TG)_x(TCTG)_y(CCTG)_z$, wherein x is an integer from 14 to 25, y is an integer from 3 to 10, and z is an integer from 75 to 11,000.

7. The isolated polynucleotide of claim 2 wherein the at risk repeat tract comprises from 75 to 11,000 CCTG repeats.

8. The isolated polynucleotide of claim 7 wherein the at risk repeat tract comprises at least 75 CCTG repeats uninterrupted by other nucleotides.

* * * * *